US012679783B2

(12) United States Patent
Frysz et al.

(10) Patent No.: US 12,679,783 B2
(45) Date of Patent: Jul. 14, 2026

(54) CERAMIC REINFORCED METAL COMPOSITE FOR HERMETIC BODIES FOR IMPLANTABLE DEVICES

(71) Applicant: Greatbatch Ltd., Clarence, NY (US)

(72) Inventors: Christine A. Frysz, Orchard Park, NY (US); Dallas J. Rensel, Sanborn, NY (US); Brian P. Hohl, Clarence, NY (US); Jonathan Calamel, Clarence, NY (US); Xiaohong (Shawn) Tang, Williamsville, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 18/784,110

(22) Filed: Jul. 25, 2024

(65) Prior Publication Data

US 2024/0383816 A1 Nov. 21, 2024

Related U.S. Application Data

(62) Division of application No. 17/942,229, filed on Sep. 12, 2022, now Pat. No. 12,344,566.

(Continued)

(51) Int. Cl.
*C04B 41/51* (2006.01)
*A61N 1/375* (2006.01)
(Continued)

(52) U.S. Cl.
CPC ........ *C04B 41/5122* (2013.01); *A61N 1/3754* (2013.01); *C04B 41/0072* (2013.01);
(Continued)

(58) Field of Classification Search
CPC ....... A61N 1/3754; B22F 1/145; B22F 1/147;

B22F 2201/013; B22F 2201/02; B22F 2998/10; B22F 2999/00; B22F 3/10; B22F 7/062; B22F 7/08; B22F 9/04; C04B 41/0072; C04B 41/4578; C04B 41/5122;

(Continued)

(56) References Cited

U.S. PATENT DOCUMENTS 6,068,589 A  5/2000 Neukermans
7,142,909 B2  11/2006 Greenberg et al.
(Continued)

FOREIGN PATENT DOCUMENTS

EP  3560552 A1  10/2019

OTHER PUBLICATIONS

Extended European Search Report; Application No. 22195094.2; Dated Jan. 20, 2023.
(Continued)

*Primary Examiner* — Shuangyi Abu Ali
(74) *Attorney, Agent, or Firm* — Michael F. Scalise

(57) ABSTRACT

A ceramic reinforced metal composite (CRMC) comprising a composition composite as an interpenetrating network of at least two interconnected composites is described. The interpenetrating networks comprise a ceramic matrix composite (CMC) and a metal matrix composite (MMC). The composition composite is particularly useful as an electrically conductive pathway extending through the insulator or ceramic body of a hermetically sealed component, for example, a feedthrough in an active implantable medical device (AIMD).

2 Claims, 37 Drawing Sheets

Related U.S. Application Data

(60) Provisional application No. 63/242,514, filed on Sep. 10, 2021.

(51) Int. Cl.
| | |
|---|---|
| *C04B 41/00* | (2006.01) |
| *C04B 41/45* | (2006.01) |
| *C04B 41/88* | (2006.01) |

(52) U.S. Cl.
CPC ...... *C04B 41/4578* (2013.01); *C04B 41/5177* (2013.01); *C04B 41/88* (2013.01)

(58) Field of Classification Search
CPC ....... C04B 41/5177; C04B 41/88; C22C 1/05; C22C 29/12; C22C 32/0031; C22C 32/0036; H01G 4/35
See application file for complete search history.

(56) References Cited

U.S. PATENT DOCUMENTS

| | | | |
|---|---|---|---|
| 7,190,051 | B2 | 3/2007 | Mech et al. |
| 7,211,103 | B2 | 5/2007 | Greenberg et al. |
| 7,291,540 | B2 | 11/2007 | Mech et al. |
| 7,480,988 | B2 | 1/2009 | Ok et al. |
| 7,618,450 | B2 | 11/2009 | Zarowski et al. |
| 7,645,262 | B2 | 1/2010 | Greenberg et al. |
| 7,709,961 | B2 | 5/2010 | Greenberg et al. |
| 7,813,796 | B2 | 10/2010 | Greenberg et al. |
| 7,835,794 | B2 | 11/2010 | Greenberg et al. |
| 7,846,285 | B2 | 12/2010 | Zhou et al. |
| 7,904,148 | B2 | 3/2011 | Greenberg et al. |
| 7,989,080 | B2 | 8/2011 | Greenberg et al. |
| 8,000,804 | B1 | 8/2011 | Wessendorf et al. |
| 8,003,513 | B2 | 8/2011 | Shah et al. |
| 8,121,697 | B2 | 2/2012 | Greenberg et al. |
| 8,163,397 | B2 | 4/2012 | Ok et al. |
| 8,165,680 | B2 | 4/2012 | Greenberg et al. |
| 8,258,635 | B2 | 9/2012 | Greenberg et al. |
| 8,285,380 | B2 | 10/2012 | Greenberg et al. |
| 8,494,635 | B2 | 7/2013 | Guebler et al. |
| 8,501,547 | B2 | 8/2013 | Greenberg et al. |
| 8,528,201 | B2 | 9/2013 | Guebler et al. |
| 8,551,271 | B2 | 10/2013 | Ok et al. |
| 8,644,937 | B2 | 2/2014 | Greenberg et al. |
| 8,653,384 | B2 | 2/2014 | Tang et al. |
| 8,670,829 | B2 | 3/2014 | Satou et al. |
| 8,742,268 | B2 | 6/2014 | Reisinger et al. |
| 8,755,887 | B2 | 6/2014 | Troetzschel et al. |
| 8,825,162 | B2 | 9/2014 | Reisinger |
| 8,841,558 | B2 | 9/2014 | Satou et al. |
| 8,872,035 | B2 | 10/2014 | Satou et al. |
| 8,886,320 | B2 | 11/2014 | Wollenberg et al. |
| 8,894,914 | B2 | 11/2014 | Pavlovic |
| 8,929,987 | B2 | 1/2015 | Troetzschel et al. |
| 8,938,309 | B2 | 1/2015 | Marzano et al. |
| 9,008,799 | B2 | 4/2015 | Stevenson et al. |
| 9,032,614 | B2 | 5/2015 | Specht |
| 9,040,819 | B2 | 5/2015 | Kempf et al. |
| 9,048,608 | B2 | 6/2015 | Pavlovic |
| 9,088,093 | B2 | 7/2015 | Reisinger et al. |
| 9,126,053 | B2 | 9/2015 | Kempf et al. |
| 9,220,169 | B2 | 12/2015 | Zhou et al. |
| 9,233,253 | B2 | 1/2016 | Stevenson et al. |
| 9,258,902 | B2 | 2/2016 | Greenberg et al. |
| 9,306,318 | B2 | 4/2016 | Reisinger |
| 9,352,150 | B2 | 5/2016 | Stevenson et al. |
| 9,403,023 | B2 | 8/2016 | Markham et al. |
| 9,407,076 | B2 | 8/2016 | Troetzschel et al. |
| 9,418,778 | B2 | 8/2016 | Makino et al. |
| 9,431,801 | B2 | 8/2016 | Markham et al. |
| 9,463,329 | B2 | 10/2016 | Frysz et al. |
| 9,478,959 | B2 | 10/2016 | Markham et al. |
| 9,480,168 | B2 | 10/2016 | Troetzschel et al. |
| 9,492,659 | B2 | 11/2016 | Brendel et al. |
| 9,504,840 | B2 | 11/2016 | Pavlovic et al. |
| 9,504,841 | B2 | 11/2016 | Markham et al. |
| 9,509,272 | B2 | 11/2016 | Reisinger |
| 9,511,220 | B2 | 12/2016 | Marzano et al. |
| 9,532,451 | B2 | 12/2016 | Greenberg et al. |
| 9,552,899 | B2 | 1/2017 | Glynn et al. |
| 9,592,377 | B2 | 3/2017 | Greenberg et al. |
| 9,592,396 | B2 | 3/2017 | Greenberg et al. |
| 9,610,451 | B2 | 4/2017 | Markham et al. |
| 9,610,452 | B2 | 4/2017 | Markham et al. |
| 9,653,893 | B2 | 5/2017 | Markham et al. |
| 9,717,150 | B2 | 7/2017 | Ok et al. |
| 9,814,891 | B2 | 11/2017 | Markham et al. |
| 9,849,296 | B2 | 12/2017 | Markham et al. |
| 9,849,297 | B2 | 12/2017 | Greenberg et al. |
| 9,855,008 | B2 | 1/2018 | Markham et al. |
| 9,889,306 | B2 | 2/2018 | Stevenson et al. |
| 9,936,590 | B2 | 4/2018 | Ok et al. |
| 9,949,376 | B2 | 4/2018 | Greenberg et al. |
| 9,993,650 | B2 | 6/2018 | Seitz et al. |
| 9,999,777 | B2 | 6/2018 | Nikolaidis et al. |
| 10,046,166 | B2 | 8/2018 | Stevenson et al. |
| 10,052,478 | B2 | 8/2018 | Greenberg et al. |
| 10,137,303 | B2 | 11/2018 | Greenberg et al. |
| 10,159,845 | B2 | 12/2018 | Greenberg et al. |
| 10,212,836 | B2 | 2/2019 | Dittmer et al. |
| 10,249,415 | B2 | 4/2019 | Seitz et al. |
| 10,272,252 | B2 | 4/2019 | Seitz et al. |
| 10,272,253 | B2 | 4/2019 | Seitz et al. |
| 10,286,219 | B2 | 5/2019 | Nikolaidis et al. |
| 10,290,400 | B2 | 5/2019 | Troetzschel et al. |
| 10,293,172 | B2 | 5/2019 | Dittmer et al. |
| 10,300,267 | B2 | 5/2019 | Shan et al. |
| 10,390,441 | B1 | 8/2019 | Ok et al. |
| 10,413,639 | B2 | 9/2019 | Dittmer et al. |
| 10,418,798 | B2 | 9/2019 | Markham et al. |
| 10,420,949 | B2 | 9/2019 | Seitz et al. |
| RE47,624 | E | 10/2019 | Tang et al. |
| 10,471,266 | B2 | 11/2019 | Morioka et al. |
| 10,500,402 | B2 | 12/2019 | Stevenson et al. |
| 10,514,044 | B2 | 12/2019 | Schibli et al. |
| 10,539,140 | B2 | 1/2020 | Keitel et al. |
| 10,559,409 | B2 | 2/2020 | Seitz et al. |
| 10,617,878 | B2 | 4/2020 | Fischer et al. |
| 10,617,879 | B2 | 4/2020 | Schibli et al. |
| 10,655,631 | B2 | 5/2020 | Schibli et al. |
| 10,679,778 | B2 | 6/2020 | Troetzschel et al. |
| 10,770,879 | B2 | 9/2020 | Markham et al. |
| 10,857,368 | B2 | 12/2020 | Seitz et al. |
| 10,881,866 | B2 | 1/2021 | Dittmer et al. |
| 10,881,867 | B2 | 1/2021 | Stevenson et al. |
| 10,918,973 | B2 | 2/2021 | Cardillo et al. |
| 10,952,332 | B2 | 3/2021 | Ok et al. |
| 11,071,858 | B2 | 7/2021 | Stevenson et al. |
| 11,110,285 | B2 | 9/2021 | Hausch et al. |
| 11,198,014 | B2 | 12/2021 | Stevenson et al. |
| 2011/0241253 | A1* | 10/2011 | Chen .................... C22C 1/0433 264/319 |
| 2018/0197661 | A1 | 7/2018 | Seitz et al. |
| 2019/0244729 | A1* | 8/2019 | Seitz .................. C04B 41/4578 |

OTHER PUBLICATIONS

Dittmer, et al., "Advanced CerMet ceramic composites for medical applications", Jul. 20, 2017, 206-211.

Kasbasi, "Developing a High Density Pt/Alumina Hermetic Feedthrough", Jun. 15, 2012.

Lu, Hong et al, Pt—Al2O3 interfacial bondings in implantable hermetic feedthroughs: Morphology and orientation, Society for Biomaterials, 2011, 817-824, Wiley Periodicals, Inc.

Rager, Jochen et al, Platinum Ceramic Composites as new Electrode Materials: Febrication, Sintering, Microstructures and Properties, Advanced Engineering Materials, Sep. 20, 2005, 81-88, vol. No. 8, Wiley InterScience.

Allen, R.V. et al, Solid state metal-ceramic bonding of platinum to

(56) References Cited

OTHER PUBLICATIONS alumina, Journal of Materials Science, Feb. 18, 1983, 2835-2843,
vol. 18, Champman and Hall Ltd., Clayton, Victoria, Australia.

* cited by examiner

100

104

102

STEP 1

STEP 2

STEP 3

(a)       =       (b)       +       (c)

Energy Loss (eV)

C0LFU602
Sintered 2000 nm

226

232

SAED Calculations for Pt 5 nm$^{-1}$ = 1.04"

| | | |
|---|---|---|
| A line = 4.28" | A spacing = 1.07" = 0.194 nm | A is (200) at 0.196 nm |
| B line = 3.53" | B spacing = 1.78" = 0.118 nm | B is (311) at 0.118 nm |
| C line = 4.69" | C spacing = 2.35" = 0.090 nm | C is (331) at 0.090 nm |

SAED Calculations for Alumina 5 nm$^{-1}$ = 1.06"
A line = 3.09"        A spacing = 0.618" = 0.343 nm        A is (012) at 0.348 nm
B line = 2.06"        B spacing = 1.03" = 0.206 nm        B is (113) at 0.208 nm
C line = 2.78"        C spacing = 1.39" = 0.153 nm        C is (221) at 0.154 nm

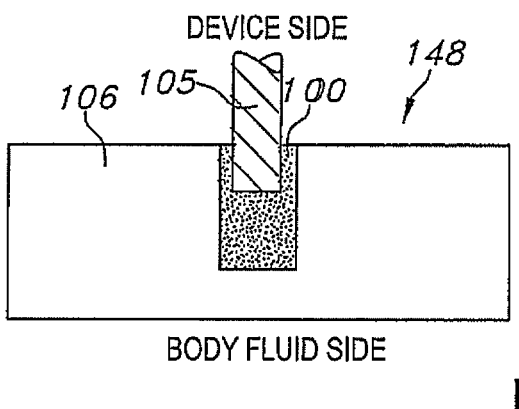
DEVICE SIDE
106   105   100   148
BODY FLUID SIDE
FIG. 55
DEVICE SIDE
106   105   100   148
BODY FLUID SIDE
FIG. 56
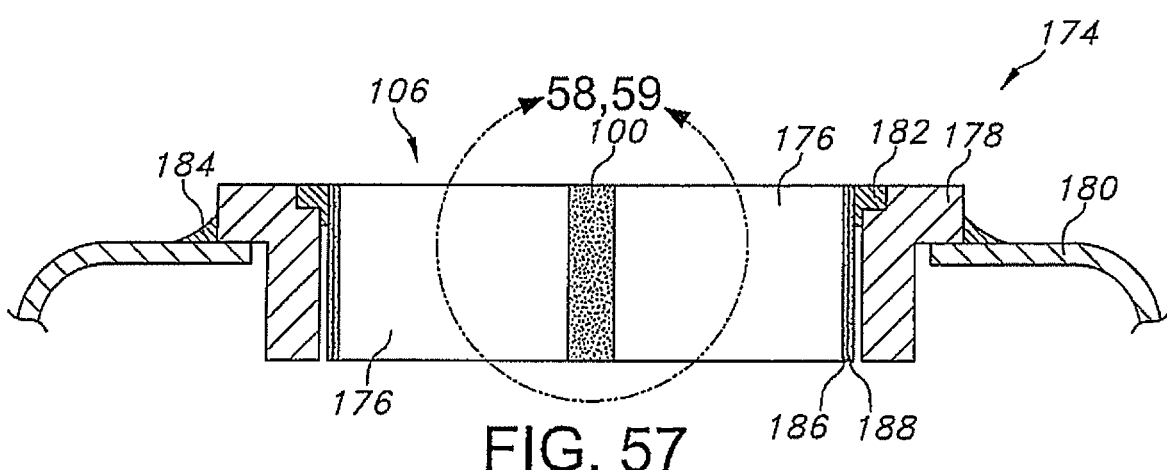
174
106   58,59   100   176   182 178   180
184
176   186  188
FIG. 57

CERAMIC REINFORCED METAL COMPOSITE FOR HERMETIC BODIES FOR IMPLANTABLE DEVICES

CROSS-REFERENCE TO RELATED APPLICATIONS

The present application is a divisional of U.S. application Ser. No. 17/942,229, filed on Sep. 12, 2022, which claims priority to U.S. provisional application Ser. No. 63/242,514, filed on Sep. 10, 2021, the content of which is incorporated fully herein.

TECHNICAL FIELD

The present invention generally relates to a hermetically sealed construct for use in an implantable medical device or system that comprises a ceramic body and a ceramic reinforced metal composite (CRMC) electrical conductor. More particularly, the present invention relates to hermetically sealed components for use in active implantable medical devices (AIMDs) having a ceramic body and a hermetically sealed electrically conductive pathway. The CRMC is a composition composite comprising an interpenetrating network of at least two interconnected composites, a ceramic matrix composite (CMC) and a metal matrix composite (MMC).

BACKGROUND

Implantable medical devices or systems typically have one or more hermetically sealed component. The hermetically sealed component typically has at least one electrical conductor used to carry a signal or conduct current through a feedthrough, an enclosure or a circuit board. As such, the electrical conductor may be supported by an insulating ceramic substrate, disposed in a via of a feedthrough, or incorporated by a device housing.

Prior art electrical conductors comprise one or more electrical conductors formed by sintering a metal powder paste or a mixed powder of metal and ceramic particles. For instance, Karbasi discloses feedthrough electrical conductors formed by co-sintering an electrically conductive paste disposed into the via of a feedthrough insulator in his 2012 thesis, "Developing a High Density Pt/Alumina Hermetic Feedthrough", the content of which is fully incorporated herein by this reference.

Dittmer et al. discloses feedthrough electrical conductors formed by co-sintering an electrically conductive metal paste to which ceramic powder was added in a paper entitled "Advanced CerMet Ceramic Composites for Medical Applications", published in the Journal of the Mechanical Behavior of Biomedical Materials 75 (2017) 206-211, the content of which is fully incorporated herein by this reference.

Prior art cermets using mixed metal and ceramic powder pastes for making electrical conductors are also disclosed in U.S. Pat. Nos. 11,110,285; 10,952,332; 10,918,973; 10,881,866; 10,770,879; 10,679,778; 10,655,631; 10,617,879; 10,617,878; 10,539,140; 10,514,044; 10,471,266; 10,418,798; 10,413,639; 10,390,441; 10,300,267; 10,293,172; 10,290,400; 10,286,219; 10,212,836; 10,159,845; 10,137,303; 10,052,478; 9,999,777; 9,949,376; 9,936,590; 9,855,008; 9,849,297; 9,849,296; 9,814,891; 9,717,150; 9,653,893; 9,610,452; 9,610,451; 9,592,396; 9,592,377; 9,552,899; 9,532,451; 9,509,272; 9,504,841; 9,504,840; 9,480,168; 9,478,959; 9,431,801; 9,418,778; 9,407,076; 9,403,023; 9,306,318; 9,258,902; 9,220,169; 9,126,053; 9,088, 093; 9,048,608; 9,040,819; 9,032,614; 9,008,779; 8,929,987; 8,894,914; 8,886,320; 8,872,035; 8,841,558; 8,644,937; 8,551,271; 8,501,547; 8,285,380; 8,825,162; 8,755,887; 8,742,268; 8,670,829; 8,528,201; 8,494,635; 8,258,635; 8,165,680; 8,163,397; 8,121,697; 8,003,513; 8,000,804; 7,989,080; 7,904,148; 7,846,285; 7,835,794; 7,813,796; 7,709,961; 7,645,262; 7,618,450; 7,480,988; 7,291,540; 7,211,103; 7,190,051; 7,142,909; and 6,068,589; the contents of which are fully incorporated herein by these references.

Hermetically sealed components made using conductive pastes having only metal or mixed metal and ceramic powders, however, tend to lack hermetical robustness. Karbasi relates that electrical conductors formed from electrically conductive platinum metal paste exhibit significant undesirable defects, such as delamination and cracks, due to mismatched sintering kinetics. Delamination and cracks generally lead to loss of hermeticity. Karbasi further reveals that even when glass is added to the metal, the electrical conductors are still weak due to either their inability to create intermediary layers for metal/ceramic bonding or an undesirable glass migration that causes porous metal/ceramic bonding.

The Dittmer et al. paper states that electrical conductors formed from electrically conductive metal pastes having added ceramic particles allow better integration of the electrical conductor into a ceramic body due to tight metal-ceramic bonding as evidenced by helium leak tests, which the authors purport is evidenced by increased composite flexural strength. However, composite flexural strength is not related to and does not indicate robust hermeticity.

The cermet prior art patent disclosures discuss hermeticity, including hermeticity after thermal shock, yet none provide fracture path analysis or any explained understanding of the hermeticity failure mechanism. More importantly, hermetic losses are still being reported. Hermetic losses have been shown to be unpredictable. Moreover, hermeticity issues are occurring even though as-manufactured feedthroughs pass hermeticity requirements. For medical implantable devices, particularly active implantable devices (AIMD), unpredictable hermetic failure is a colossal safety concern for an implant patient, as hermetic leaks can result in ingress of body fluids into the device, which can damage sensitive therapy delivery electronics therewithin. For instance, hermetic failure can cause the operation of an implanted device to be interrupted, which means the patient doesn't properly receive the intended electrical therapy. Worse yet, hermetic failure can cause the implanted device to completely shut down. Complete shutdown of an implanted device is immediately life-threatening to a pacemaker dependent patient, as the patient's heart cannot function without electrical stimulation therapy. The patient's heart actually stops beating and the patient could very well die.

Accordingly, what is needed is a robust electrical conductor that can reliably sustain hermeticity over the operational life of an implanted medical device. The ceramic reinforced metal composite (CRMC) electrical conductor of the present invention fulfills these needs and provides other related advantages.

SUMMARY OF THE INVENTION

The ceramic reinforced metal composite (CRMC) electrical conductor disclosed herein applies to all the embodiments in the literature and prior art patents disclosed above. The CRMC electrical conductors of the present invention also apply to all implantable devices and systems, such as, but are not limited to, cardiac pacemakers, cardioverter defibrillators, gastric pacemakers, brain stimulators, cochlear devices, cochlear systems, ocular devices, ocular systems, nerve stimulators, bone stimulators, sensors, drug delivery systems, monitors, recorders, bions, microchips, microelectromechanical systems (MEMS), electronic circuits, electronic circuit boards, electronic devices, electronic systems, integrated circuits (IC), bionic devices, bionic systems, bionetworks, SMART pills, optical diagnostic devices, optical diagnostic systems, optical therapy devices, optical therapy systems, digital devices and digital systems.

The embodiments of the present invention comprise a ceramic body and an electrically conductive pathway having at least one CRMC electrical conductor. The electrically conductive pathway may comprise a conductive via, a circuit trace, an electrical connection pad, a conductive pocket, a conductive hermetic seal, an electrode, a conductive track, a conductive trough, a conductive channel, or combinations thereof. The CRMC electrical conductor is mechanically and chemically bonded to the ceramic body. The ceramic body may comprise one of a substrate, a feedthrough insulator, a device housing, or combinations thereof. In an embodiment, the CRMC electrical conductor is hermetically sealed to the ceramic body.

The CRMC is a composition composite comprising an interpenetrating network of two or more interconnected composites that wind and intertwine about, through and around each other. In an embodiment, the CRMC comprises a ceramic matrix composite (CMC) and a metal matrix composite (MMC). In an embodiment, the CMC of the CRMC comprises a ceramic matrix within which metal-containing particles are embedded. The metal-containing particles may be metal or metal alloy particles, metal composite particles, metal-ceramic composite particles, or combinations thereof. In an embodiment, the MMC has a metal matrix within which ceramic particles are embedded. The ceramic particles may be of a single ceramic material, a ceramic composite, a ceramic-metal composite, a compound ceramic particle (two or more ceramic materials), or combinations thereof. In an embodiment, the MMC comprises a platinum (Pt) matrix within which an alumina ($Al_2O_3$) ceramic reinforcement is embedded. In an embodiment, the CMC comprises an $Al_2O_3$ matrix within which a Pt or Pt-containing reinforcement is embedded. In an embodiment, the CRMC comprises an electrically conductive additive. In an embodiment, the metal and the ceramic of both the CMC and the MMC are mechanically and chemically bonded. In an embodiment, the CMC supports the MMC, and the MMC provides electrical conductivity to the CRMC.

The CRMC composition composite is formed in three steps: STEP 1, making a metal-ceramic composite particle powder; STEP 2, forming a flowable medium, using the metal-ceramic composite particle powder; Step 3: co-sintering the flowable medium and a green state ceramic body.

A preferred STEP 1 includes a partial sinter process to form the composite particles. Partial sintering of a mixed powder comprising metal and ceramic particles causes the metal particles to soften and flow without sintering the ceramic particles. When the metal particles flow, the ceramic particles become adhered to the metal, which enables composite particle formation. The flowable medium is one of as an ink, a paste or a gel.

In an embodiment, the CRMC comprises a platinum (Pt) metal and an alumina ($Al_2O_3$) ceramic, and the ceramic body is an $Al_2O_3$ ceramic. In an embodiment, the coefficient of thermal expansion (CTE) of the CRMC matches the CTE of the ceramic body.

In an embodiment, the ceramic body comprises one or more hermetically sealed CRMC electrical conductors extending to a ceramic body first side and to a ceramic body second side. In an embodiment, the ceramic body comprises at least one hermetically sealed CRMC electrical conductor that extends through the thickness of the ceramic body to a device side ceramic body surface and to a body fluid side ceramic body surface. In an embodiment, the ceramic body comprises one or more CRMC electrical conductors comprising a surface diameter larger than a ceramic body via hole diameter. In an embodiment, the ceramic body comprises one or more CRMC electrical conductors formed in a blind via hole. In an embodiment, the ceramic body comprises a combination electrical conductor comprising CRMC, and a metal addition selected from the group consisting of a metal construct, a metal alloy construct, a leadwire, a terminal pin, a lead, a wire, a pin, a connector, a clip, a nail head construct, a pad, a metal protrusion, a metal alloy protrusion, a metal insert, a metal alloy insert, a metal alloy protrusion, an electrode, and combinations thereof. In an embodiment, the ceramic body comprises an electrically conductive pathway, wherein at least a portion of the electrically conductive pathway comprises CRMC. In an embodiment, the ceramic body comprises a combination electrical conductor comprising CRMC and a solid fill metal material.

In an embodiment, the ceramic body comprises a CRMC electrical conductor that extends through the ceramic body in a straight line along a longitudinal direction. In an embodiment, the ceramic body comprises a CRMC electrical conductor that extends through the ceramic body in two or more directions. In an embodiment, the ceramic body comprises an electrically conductive pathway having a CRMC electrical conductor and one of: an electronic component, a circuit board, an electrically conducting element; intermediate electrically conductive elements; electrically conducting connection elements; or combinations thereof. In an embodiment, the ceramic body comprises a CRMC electrical conductor that is electrically connected to one of: a conducting via, a circuit trace, an electrical connection pad, a conducting pocket, a conducting hermetic seal, an electrode, a conducting track, a conducting trough, a conducting channel, or combinations thereof. In an embodiment, the ceramic body comprises a CRMC electrical conductor that is electrically connected to one of: an interior electrical connection surface, an exterior electrical connection surface, or both.

BRIEF DESCRIPTION OF THE DRAWINGS

FIG. 55 is a monolithic feedthrough insulator having a CRMC solid via electrical conductor with a metal addition;

FIG. 56 is a laminated multilayer feedthrough insulator having a CRMC solid via electrical conductor with a metal addition;

FIG. 57 illustrates a cross sectional view of a hermetically sealed feedthrough having a CRMC electrical conductor;

DETAILED DESCRIPTION OF THE PREFERRED EMBODIMENTS

Figure 1:
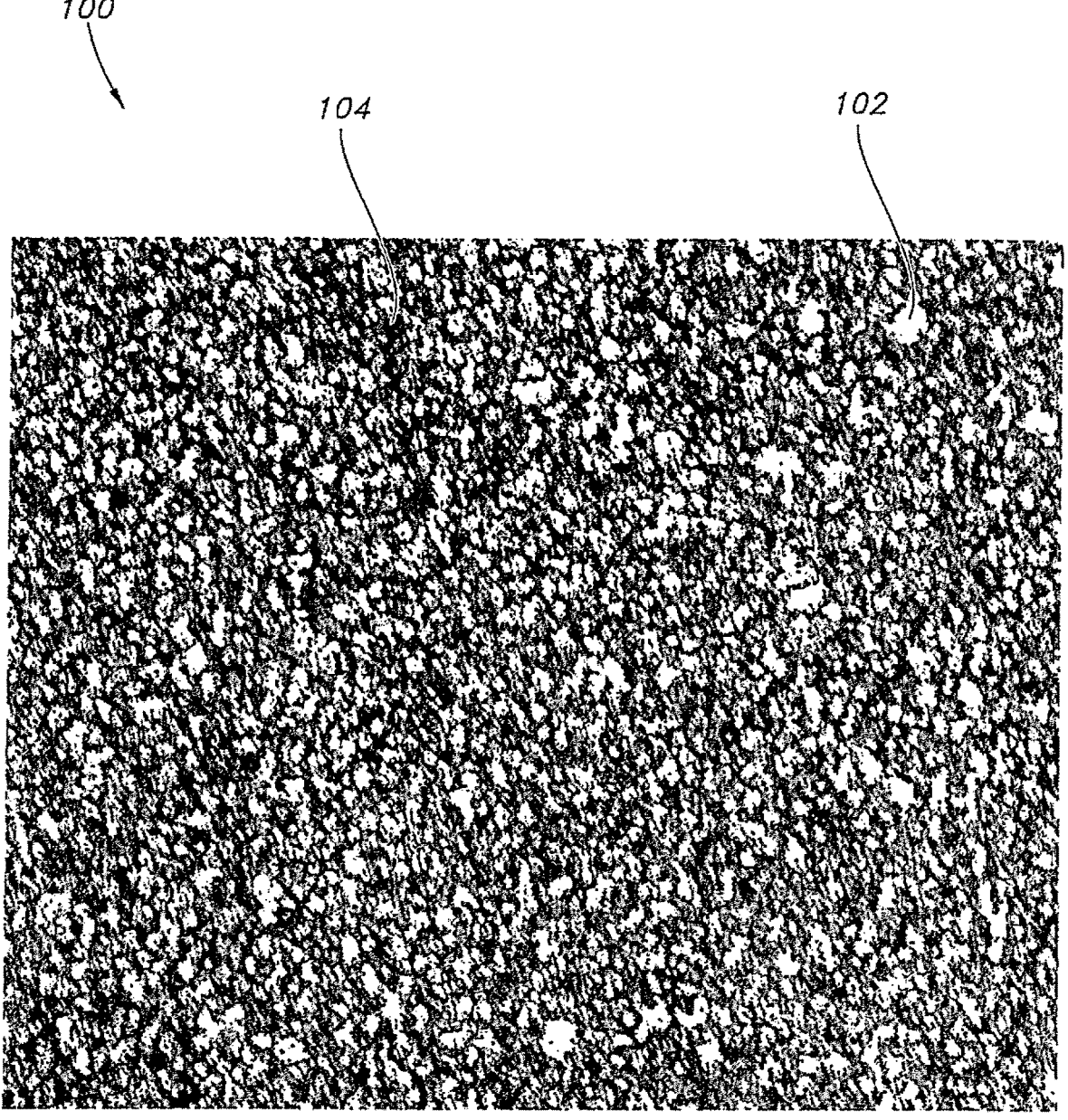
FIG. 1 is a bright field optical microscope image of a ceramic reinforced metal composite (CRMC)

The present invention discloses a multi-phase material consisting of an in-situ composition composite comprising two entwined matrix composites where the reinforcing phase of each matrix composite is produced within a respective matrix during the fabrication of a hermetically sealed ceramic body.

Definition of the Terms Used Herein

"Ceramic Reinforced Metal Composite (CRMC)"—a composition composite comprising at least a ceramic composite and a metal composite, for example, a ceramic matrix composite (CMC) and a metal matrix composite (MMC);

"Ceramic Matrix Composite (CMC)"—a composite material having a ceramic matrix within which one or more other materials are embedded;

"Metal Matrix Composite (MMC)"—a composite material having a metal matrix within which one or more other materials are embedded;

"cermet"—a composite comprising a metal and a ceramic;

"composite"—a material comprising two or more different materials that, when combined, work together to give the composite one or more unique properties not attainable by the individual materials themselves;

"composition composite"—a composite material consisting of at least two different composites, each composite being distinct without any loss of its identity, which act together to provide one or more unique composition composite properties not attainable by the individual composites themselves;

"electrically conductive pathway"—a route through which an electrical signal and/or current flows; the electrically conductive pathway includes one or more electrical conductors and/or electrical circuit components; "electrical conductor"—a conductive via, a circuit trace, an electrical connection pad, a conductive pocket, a conductive hermetic seal, an electrode, a conductive track, a conductive trough, or a conductive channel;

"in-situ composite"—a multi-phase composite having discontinuously reinforced metal and ceramic composites produced by processing techniques that create a solid composition composite in-situ, such as by a sintering and/or a firing process; the discontinuously reinforced metal and ceramic composites may comprise a ceramic-based reinforced metal and a metal-based reinforced ceramic (such as, an MMC and a CMC) respectively, which is synthesized during the sintering or firing process to form a solid metal and ceramic composition composite;

"multi-phase"—a substance having more than one distinct compound and/or element therewithin, each compound and/or element having different material properties and/or different compositions; "inclusion"—a material embedded within another material, the embedded material being different from the other material; "matrix"—a material that surrounds and contains another different material; the matrix provides a medium for binding and holding reinforcements;

"reinforcement"—a material that improves the overall properties of the matrix; the reinforcement provides tailored material properties for optimized performance of a composite;

"microstructure"—two distinct phases, which are materials that can be distinguished on the basis of structure or composition, for example, a metal and a ceramic;

"morphology"—observable structures and/or shapes, often by microscopy or scattering techniques, of different phase domains present within a mixture or a composite;

"partial sinter"—sintering a mixed powder batch comprising both metal and ceramic powders so that the metal particles of the mixed powder batch soften, flow and bind to each other and, at the same time mechanically stick to the ceramic particles of the mixed powder batch, while the ceramic particles of the mixed powder batch remain unsintered;

"sieving"—a screening method for separating a mixture of metal-ceramic particle sizes into two or more composite particle size fractions;

"homogenization"—the process of uniformly dispersing and distributing powder particles throughout a flowable medium, such as an ink, a paste or a gel;

"green state"—an as-formed ceramic body before sintering; the as-formed ceramic body may be, but is not limited to, a pressed ceramic powder compact, a pressed ceramic powder having organic or inorganic additives, a ceramic tape, a ceramic film, a ceramic sheet, or a laminated multi-sheet (or multilayer) ceramic;

"flexural strength"—a measure of the ultimate strength of a specified beam in bending as defined by ASTM C1161-13;

"CTE match"—when the CTE of two different materials are either equal, similar, or complementary to each other, where the CTE comprises a converter of $1 \times 10^{-6}$ length/length/degree Centigrade (° C.)=0.55556 length/length/degree Fahrenheit (° F.);

"equal CTE match"—a 0 per ° C. (0 per ° F.) difference in the CTE of two dissimilar materials;

"similar CTE match"—a difference in the CTE of two dissimilar materials ranging between >0 per ° C. to ±2.5 per ° C. (>0 per ° F. to ±1.4 per ° F.); "complementary CTE match"—a difference in the CTE of two dissimilar materials ranging between >2.5 per ° C. to +10 per ° C. (>1.4 per ° F. to ±5.6 per ° F.).

DESCRIPTION OF THE FIGURES

FIG. 1 is a bright-field optical microscope image at 500× magnification showing a ceramic reinforced metal composite (CRMC) 100 created in-situ during co-sintering a ceramic body and electrical conductors formed when a via is filled with a paste made from a powder of composite particles. Bright-field illumination causes metals to appear dark while ceramics appear bright. FIG. 1 reveals that the composite CRMC 100 of the present invention at least consists of a metal 104 and a ceramic 102. The metal 104 and the ceramic 102 of the CRMC 100 are uniformly distributed and the CRMC 100 exhibits a density greater than 95%. The CRMC 100 of FIG. 1 is only an example and is not meant to be limiting.

Figure 2:
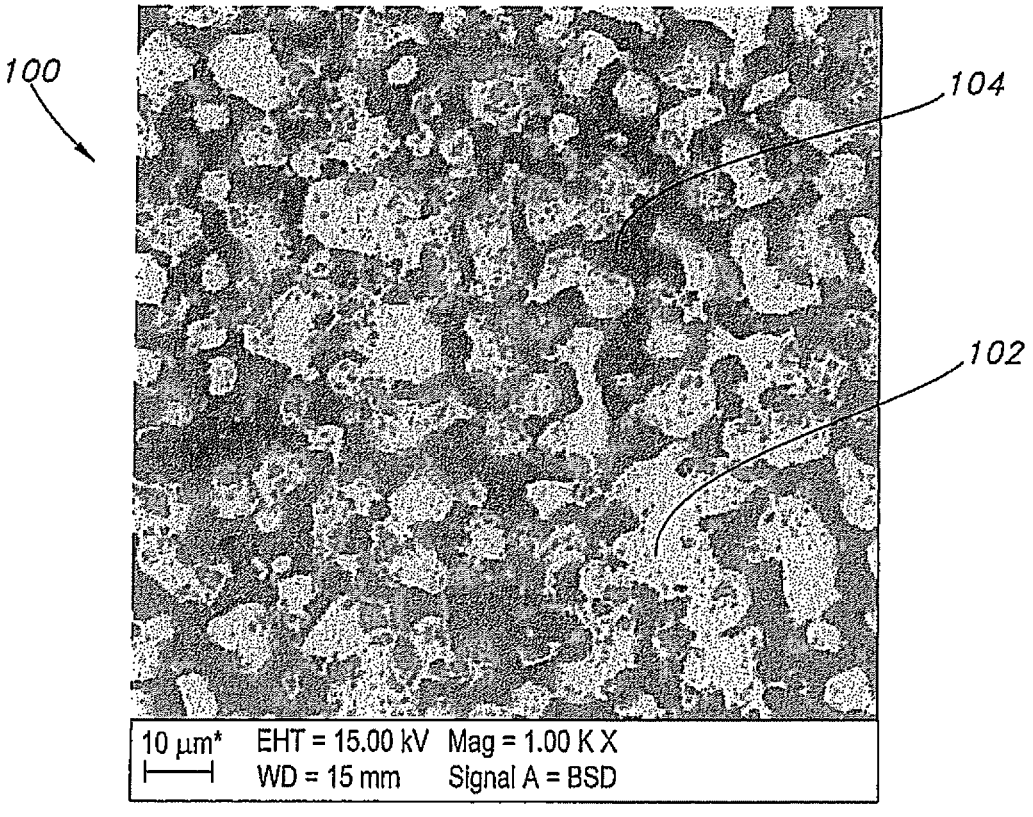
FIG. 2 is a backscattered-electron (BSE) scanning electron microscope (SEM) image of the CRMC of FIG. 1.

FIG. 2 is a backscattered-electron (BSE) scanning electron microscope (SEM) image of the CRMC 100 of FIG. 1 at 1,000× magnification. A BSE SEM provides contrast such that metals exhibit a brighter BSE intensity, while ceramics exhibit a darker BSE intensity. FIG. 2 reveals that both the metal 104 and the ceramic 102 of the CRMC 100 contain inclusions and that the CRMC 100 is essentially devoid of porosity, meaning no visible void space, indicating high density close to 100% and extremely low void fraction near 0. Additionally, the metal 104 and the ceramic 102 of the CRMC 100 each seem to wind around and about each other, exhibiting an intertwining character that is best described as an infiltration over, a penetration through, and a spreading about one another, where the metal 104 and the ceramic 102 fully contact each other throughout. In other words, the CRMC 100 of the present invention is a homogeneously distributed monolithic solid comprising a reinforced metal and a reinforced ceramic uniformly intermingled in union with one another, where the inclusions embedded within the metal 104 and the ceramic 102 are unique composite reinforcements of the metal 104 and the ceramic 102.

Figure 3:
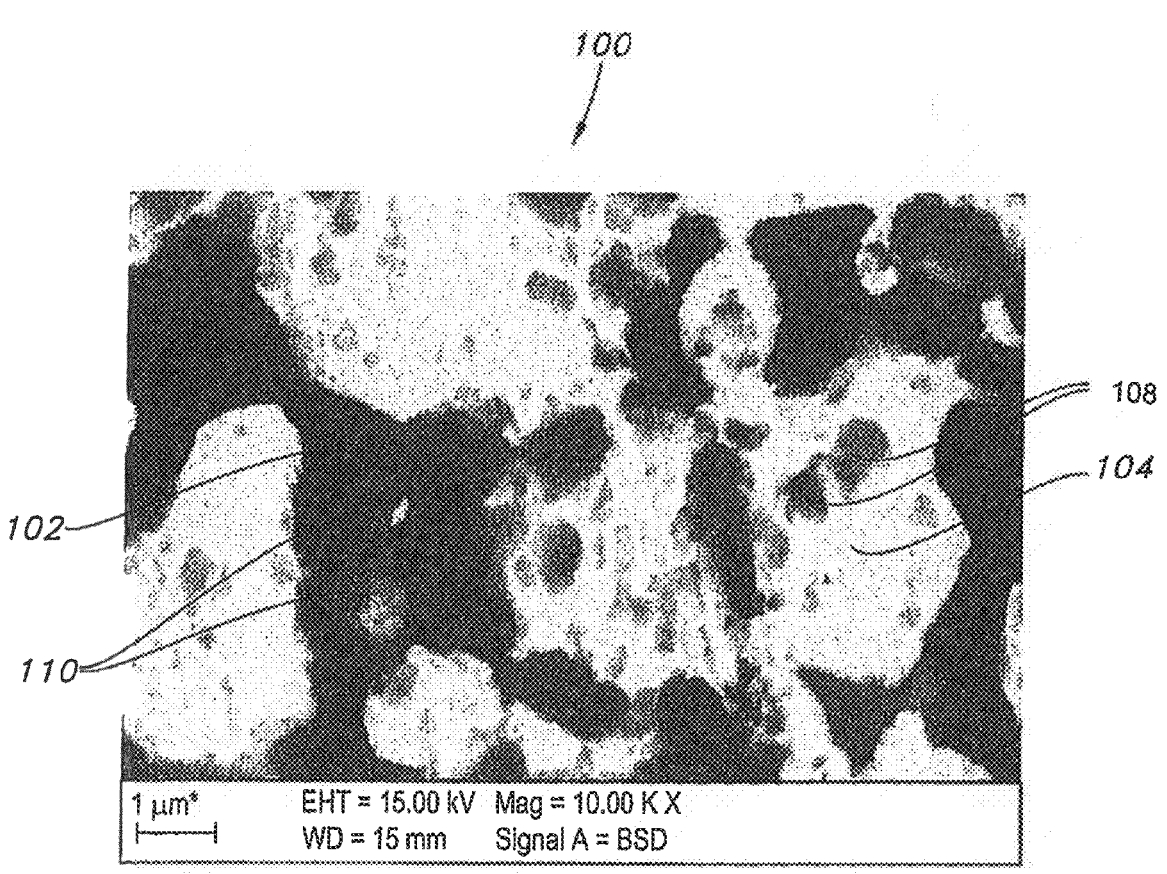
FIG. 3 is a BSE SEM image of the CRMC at 10,000× magnification.

FIG. 3 is a BSE SEM image of the CRMC 100 of the present invention at 10,000× magnification. The BSE SEM image contrast shows that the metal 104 contains ceramic reinforcement 108 and the ceramic 102 contains metal-based reinforcement 110. Also visible is that the metal 104 and the ceramic 102 each surround their respective inclusions. Consequently, the metal 104 is a metal matrix for the ceramic reinforcement 108 and the ceramic 102 is a ceramic matrix for the metal-based reinforcement 110. Accordingly, the microstructure of the CRMC 100 of FIG. 3 comprises two different composite materials, a metal matrix composite (MMC), comprising a matrix of metal 104 within which ceramic reinforcements 108 are embedded, and a ceramic matrix composite (CMC), comprising a matrix of ceramic 102 within which metal-based reinforcements 110 are embedded.

Figure 4:
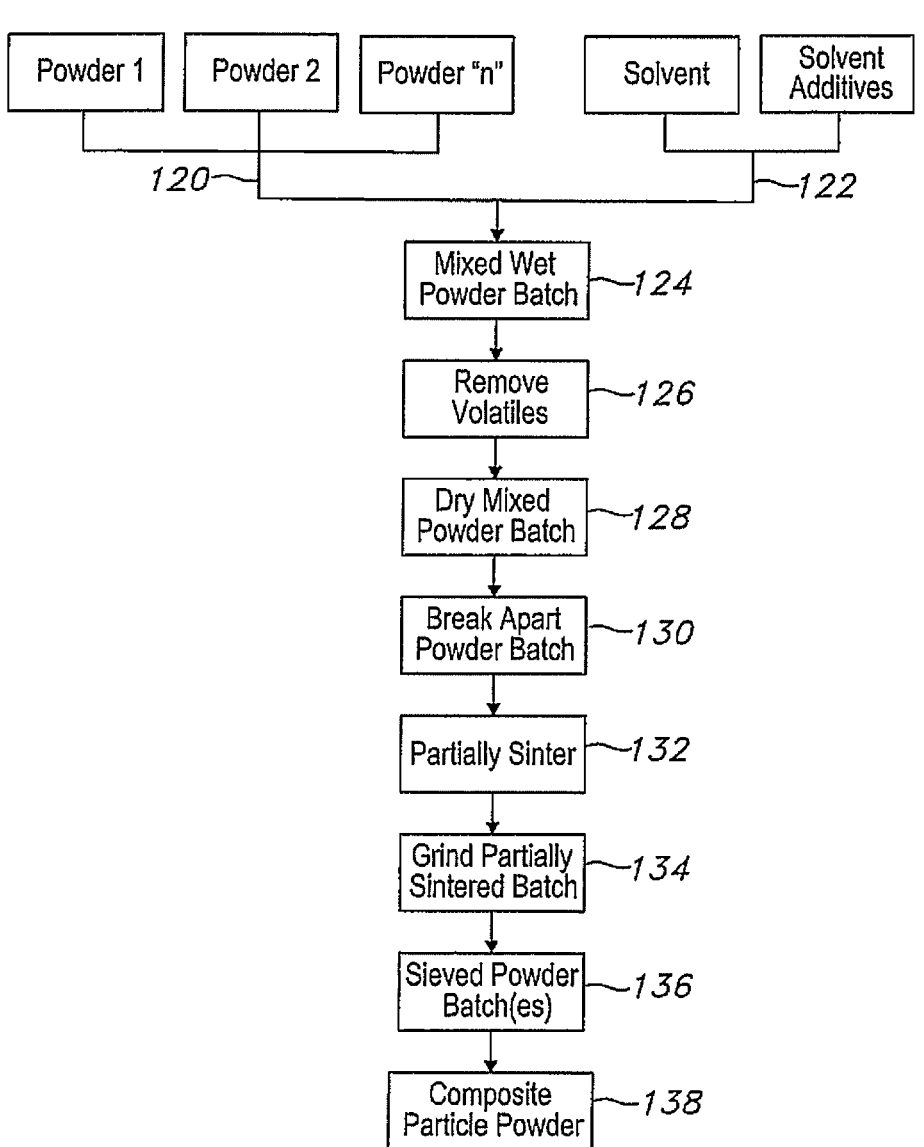
FIG. 4 is the flow chart for forming a composite particle powder.
Figure 6:
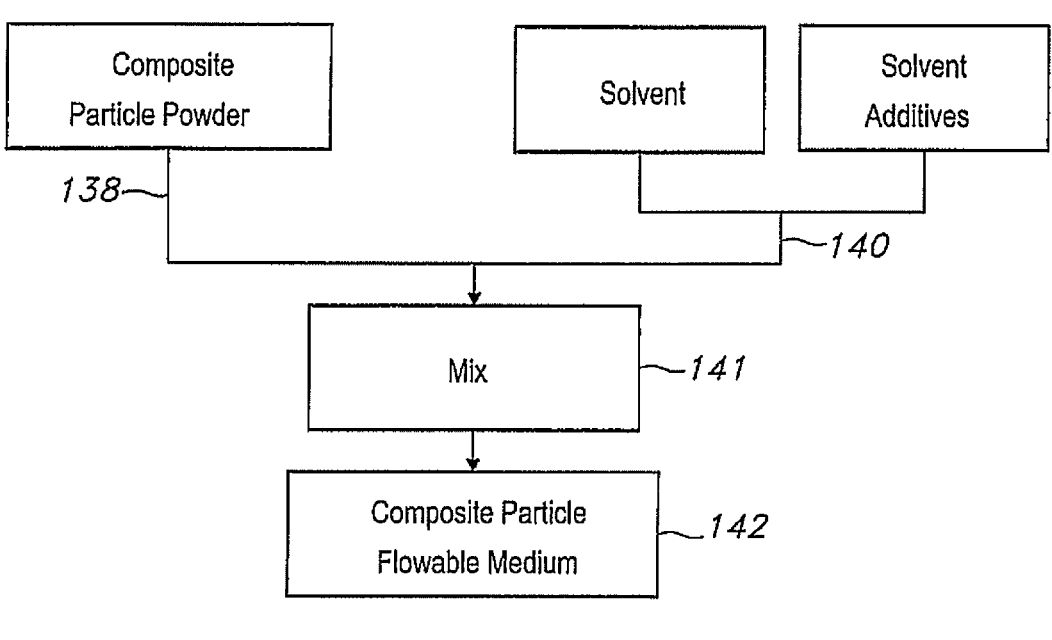
FIG. 6 is the flow chart for forming a composite particle flowable medium.
Figure 7:
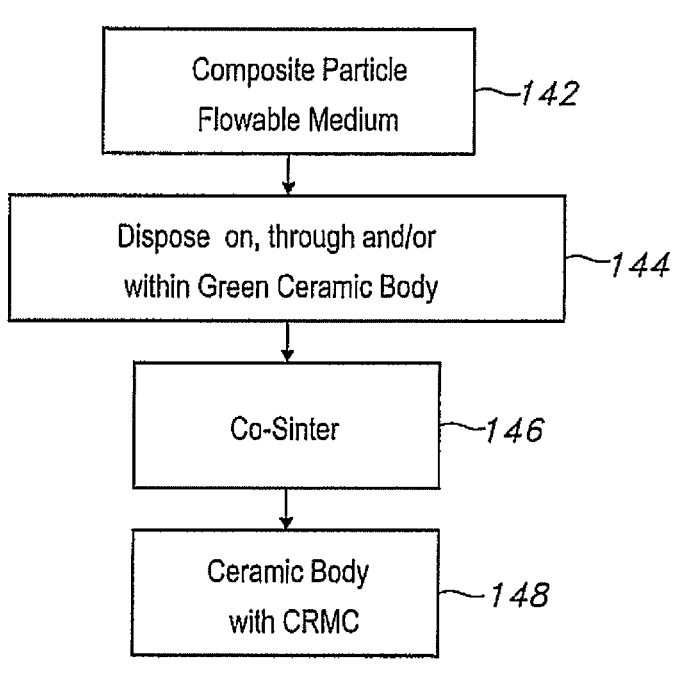
FIG. 7 is the flow chart for forming a hermetically sealed ceramic body with CRMC.

FIGS. 4, 6 and 7 are flow charts of the process for creating the CRMC 100 of the present invention. A three-step process is used to form hermetically sealed ceramic bodies containing CRMC 100. The CRMC 100 of a hermetically sealed ceramic body may be one or more solid electrical conductors, for example, electrically conductive pathways, electrically conductive co-sintered solid vias, circuit traces, electrodes, and/or electrical circuits, all of which can all be made by the three-step CRMC method disclosed herein.

FIG. 4 is the flow chart for STEP 1, which forms a composite particle powder 138 containing particles having a metal and a ceramic. STEP 1 involves mixing a metal and ceramic powder blend 120 and a solvent and optional additives 122 to form a mixed wet powder batch 124. The metal powder may be selected from the group of gold, platinum, palladium, silver, iridium, rhenium, rhodium, titanium, tantalum, tungsten, niobium, zirconium, vanadium, and alloys or combinations thereof. The ceramic powder may be selected from one or more of the alumina, baria, calcia, ceria, magnesia, silica, strontia, titania, and zirconia ceramic families and combinations thereof. The size of the metal or the ceramic particles of the metal and ceramic powder blend 120 ranges between ≥1 nanometer (nm) to ≤45 microns (μm).

Mixing the metal and ceramic powder blend 120 and the solvent and optional additives 122 may be done by a ribbon mixer, a tumble mixer, a planetary mixer, a centrifugal mixer, a magnetic mixer, an ultrasonic mixer or a resonant acoustic mixer to form the mixed wet powder batch 124.

The mixed wet powder batch 124 then undergoes drying or vaporization to remove the volatiles 126. Volatiles may be removed 126 by one of drying in air, heating in a furnace, or exposing to a vacuum to provide a dry mixed powder batch 128. The properties of the drying container will generally depend on the drying method used. As the ceramic component of the mixed wet powder batch 124 can be abrasive, the drying container should have excellent wear and abrasion resistance, regardless of drying method. For drying by heat, the furnace boat should be capable of withstanding the drying temperature, taking into consideration whether drying was done under reducing, inert, or high vacuum conditions. For high temperature drying, the furnace boat must also have good high temperature chemical resistance in addition to high temperature functional capability. Refractory furnace boats are useful for high temperature drying. Alumina is a common refractory furnace boat as alumina possesses a high melting point, strong hardness, and good chemical stability, making it a good material to withstand high temperature and chemical corrosion. Alumina is versatile and has low material cost. Zirconia, zirconia stabilized with yttria, magnesia or calcia, alumina-zirconia, boron nitride and fused silica refractory furnace boats are also options. Removing the volatiles 126 causes the metal and ceramic powder particles to compact and mechanically stick together resulting in a dry mixed powder batch 128 that has clumps, aggregates and/or agglomerates of non-uniform particle packing.

After removing the volatiles 126, the dry mixed powder batch 128 is subjected to an attrition step where the powder particles are broken apart 130. This can be done by hand, for example, using a mortar and pestle, or by conventional crushing, milling, pulverizing or grinding technologies to reduce the dry mixed powder particle size. Such particle size adjustment processes proceed through mechanisms of compression, mechanical impact or particle attrition. In the case of compression, the clumps, aggregates and/or agglomerates are subjected to stress between rollers, which then break them apart to form smaller dry mixed powder batch particles. In the case of mechanical impact, the clumps, aggregates and/or agglomerates are compressed between grinding media causing shearing forces that fragment them into smaller dry mixed powder batch particles. In particle attrition, the surfaces of the clumps, aggregates and/or agglomerates are subjected to wear or erosion by contact with grinding media, which breaks them apart into smaller dry mixed powder batch particles.

The broken apart dry mixed powder batch 130 is then partially sintered 132. The partial sintering 132 of the present invention is specifically directed toward thermally initiating sufficient softening of the metal 104 of the broken apart dry mixed powder batch 130 so that the metal 104 begins to flow, without affecting the ceramic 102 of the broken apart dry mixed powder batch 130, which remains solid. During partial sintering, the softened metal 104 of the broken apart dry mixed powder batch 130 spreads about, over and between the solid ceramic 102. As the spreading metal 104 continues to flow so that the metal particles coalesce and fuse, while at the same time, surround, capture, and mechanically adhere to the solid ceramic 102.

For example, the inventors have discovered that platinum (Pt) powder, depending on particle size, can start to sinter above 400° C. The inventors have also discovered that alumina ($Al_2O_3$) powder can start to sinter above 1,000° C. (depending on its purity). For instance, 96% $Al_2O_3$ powder has been shown to start sintering at 1,300° C. By varying combinations of other oxides in the 96% $Al_2O_3$ powder and restricting particle size of $Al_2O_3$ powder, the $Al_2O_3$ powder sinter start can be adjusted. By selecting a temperature that targets the metal 104 of the broken apart dry mixed powder batch 130 so that it softens and spreads, while the ceramic 102 remains solid, the ceramic 102 can freely float with the spreading metal 104. On solidification of the metal 102, the ceramic 102 is either embedded within or mechanically adhered to the metal 104. Depending on the metal 104 and ceramic 102 materials selected to create the broken apart dry mixed powder batch 130, the partial sinter temperature range may be between ≥350° C. to ≤1,000° C. For partial sintering a Pt and Al.sub.2O.sub.3 broken apart dry mixed powder batch 130, the partial sinter temperature ranges between ≥400° C. to ≤900° C.

It is understood that partial sintering may be accomplished by one of: thermal processing at a temperature and/or pressure that is less than a co-sintering temperature; selective inhibition sintering; selective laser sintering; or selective reactive sintering. Other methods that can be used to partial sinter include electron beam melting, multi-beam laser additive manufacturing, selective mask sintering, high-speed sintering, selective heat sintering, spark plasma sintering, and binder jetting. It is also understood that the composite particle powder 138 can be made by alternate methods besides thermal partial sintering. For example, composite particle powders 138 can alternatively be made by co-precipitation, co-deposition, an organometallic route, reactive sintering, reactive hot isostatic pressing, among others. The inventors, however, prefer thermal partial sintering to form the composite particle powder 138 because it is simple, more efficient and the most flexible approach for creating the metal and ceramic composite particle powders 138 of the present invention.

After partial sintering, the partially sintered batch 132 is then ground to form a ground partially sintered batch 134. Grinding may be done by a ball mill, tube mill, roller mill, media, or a vertical mill or a tumbler; a hammer and impactor pulverizer; a ring or disc mill; a high-pressure grinding roller or roll mill; a granulator; a cutting, knife or shredder pulverizer; a rotor, pin or universal mill; a jet or fluid energy mill; or a buhrstone or attrition mill.

The ground partially sintered batch 134 is then sieved to provide one or more sieved powder batches 136. The sieved powder batch(es) 136 then becomes one or more composite particle powders 138. Multiple composite powder batches 138 are obtained by consecutive sieving to separate fine composite particles from more course composite particles. Consecutive sieving passes the ground partially sintered batch 134 through one or more sieves of specified mesh size. The ground partially sintered batch 134 may be passed through "n" number of sieves of specified consecutively smaller mesh sizes. In general, the sieve traps oversized composite particles above the screen, while undersized composite particles pass through the screen. Sieves can be used in stacks to divide composite particle powders 138 into various particle size fractions, so that composite particle powder formulations having specified composite particle size distributions can be made. In other words, consecutive sieving can separate the produced composite particle powder 138 into various powder groups, each powder group being defined by an average composite particle size, a composite particle size range, or a composite particle size distribution.

Further regarding consecutive sieving, the composite particles are generally collected from each mesh size after sieving. The mesh number, which is also a sieve identifier, is a measure of how many openings there are per linear inch in the sieve screen. The sieve screen may be in the form of a metal wire cloth, a perforated metal plate or an electroformed sheet. Commercially available sieve mesh sizes are typically regulated by standards. ISO-3310 is an international standard having the general title, "Test Sieves—Technical requirements and testing". The ISO-3310 standard has three parts: Part 1—test sieves of metal wire cloth; Part 2—test sieves of perforated metal plate, and Part 3—test sieves of electroformed sheets.

ISO-3310 conforms to ISO 565. ISO 565 defines nominal sizes of screen openings. Nominal sizes of openings are given as follows: (a) for metal wire cloth—ranges between 125 mm to 20 μm; (b) for perforated metal plate—square holes: from 125 mm to 4 mm/round holes: from 125 mm to 1 mm; (c) for electroformed sheet with square or circular apertures—from 500 μm to 5 μm.

Other commonly used standards include EN-933 (European standard), ASTM E11 and ASTM E313 (U.S. standards). Pending application needs, custom sieve mesh sizes are also an option. The composite particle powder 138 may have metal content ranging between ≥1% to ≤99% by volume. The composite particle powder 138 may have a ceramic powder content ranging between ≥1% to ≤99% by volume. The particle size of the composite particle powder of the present invention ranges between ≥5 nanometers to ≤100 microns in diameter.

Optionally, after partial sintering, but prior to forming a composite particle flowable medium 142, or after sieving, but prior to forming a composite particle flowable medium 142, the metal and ceramic composite material may be subjected to a reduction treatment (not shown in FIG. 4), for example, in a nitrogen and hydrogen gas mixture (such as, 95% $N_2$, 5% $H_2$), at a temperature range in between 200° C. to 700° C. Reduction treatments can be used to adjust the composite particle composition of the final composite particle powder 138.

Figure 5:
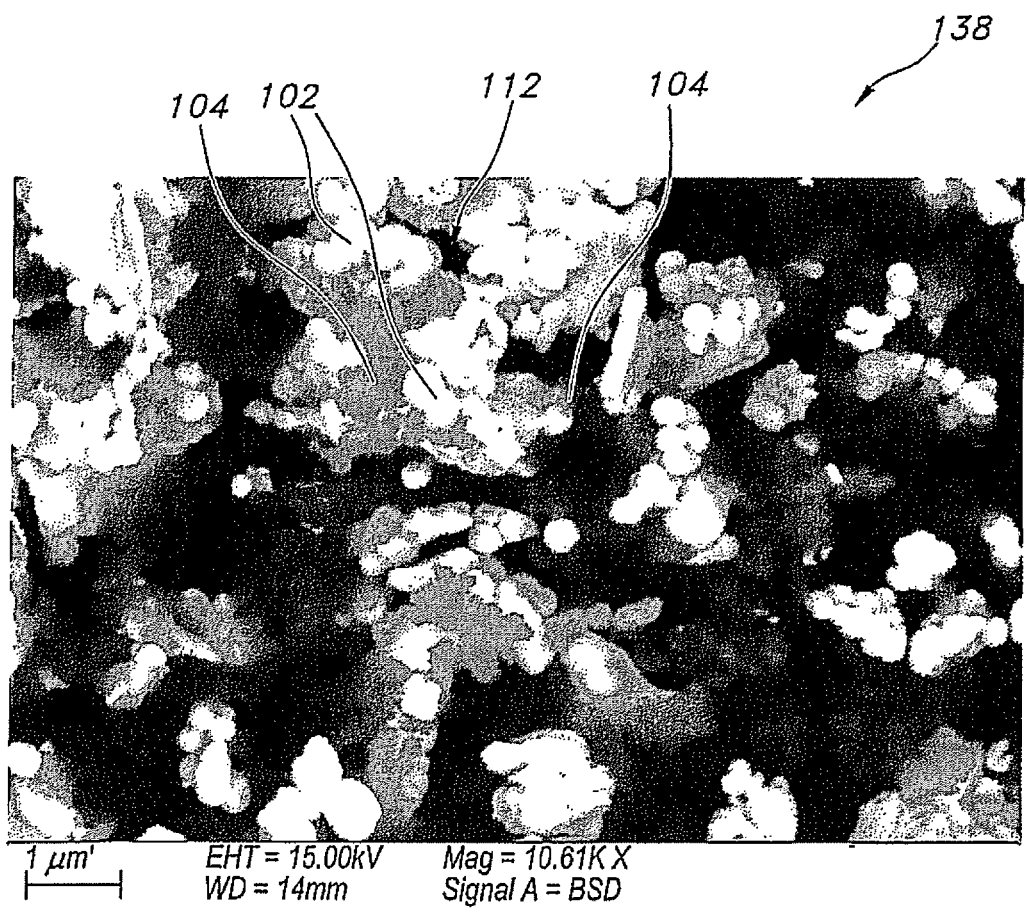
FIG. 5 is a BSE SEM image of a composite particle powder.

FIG. 5 is a BSE SEM image of the composite particle powder 138 made by STEP 1 of FIG. 4 at about 10,000× magnification. The BSE SEM contrast shows that the composite particles 112 of the composite particle powder 138 comprise a metal 104 and a ceramic 102 that are adhered to each other.

FIG. 6 is the flow chart for STEP 2, which forms a composite particle flowable medium 142, such as an ink, a paste or a gel. In STEP 2, the composite particle powder 138 and one or more solvents and optional solvent additives 140 are mixed 141. An ink may be used to form, for example, electrically conductive traces or electrode plates on or within a ceramic body. The ink may comprise a composite particle powder volume loading ranging between ≥1 volume % and ≤40 volume %.

A paste may be used to form electrical conductors, for example, in via through-holes or in blind holes in a ceramic body, such as an insulator for a hermetically sealed feedthrough, a housing of a medical device, a substrate for an electrical component, among others. The paste may comprise a composite particle powder volume loading ranging between ≥20 volume % and ≤90 volume %.

A gel may be used to form, for example, electrically and/or thermally conductive pads, pockets or pocket-pads, hermetic seams or joints, or electrically conductive traces on, through and/or within a ceramic body. The gel may comprise a composite particle powder volume loading ranging between ≥40 volume % and ≤80 volume %. Mixing 141 the composite particle powder 138 and the solvent and optional solvent additives 140 may be done by a ribbon mixer, a tumble mixer, a planetary mixer, a centrifugal mixer, a magnetic mixer, an ultrasonic mixer or a resonant acoustic mixer to form the composite particle flowable medium 142.

A homogenization process (not shown) may optionally be added to uniformly disperse and distribute the composite particles 112 of the composite particle powder 138 throughout the composite particle flowable medium 142.

Homogenizing of the composite particle flowable medium 142 may further include a breakdown process (not shown) that may optionally further reduce the size of any composite powder agglomerates, aggregates, or clumps so that composite particle flowable medium 142 can flow smoothly and can easily be dispensed. Homogenization may be done by one of a mortar and pestle, a blender type instrument, a bead mill, an ultrasonic treatment or sonication, a rotor-stator mixer, a high-pressure homogenizer, a ball mill, a high or ultra-high shear mixer, among other similarly physical force methods. The viscosity of the composite particle flowable medium 142 may be adjusted by the size and volume % loading of the composite particles 112 and/or by specifying the shapes and sizes of the particles of the metal 104 and the ceramic 102 powders originally used to form the mixed wet powder batch 124. Viscosity ranges of the composite particle flowable medium 148 of the present invention are given in Table 1 below. The units of the viscosities of Table 1 are in cP at a shear rate of $1 \text{ s}^{-1}$, where 1 cP=1 mPa*s.

TABLE 1

| Flowable medium | Viscosity range (cP) |
| --- | --- |
| Ink | 0.1-50,000 |
| Paste | $1 \times 10^5\text{-}1 \times 10^{10}$ |
| Gel | 10,000-500,000 |

To achieve suitable CRMC 100 electrical conductivity after forming a hermetically sealed ceramic body with CRMC 148, the preferred embodiment of the composite particle flowable medium 142 comprises a metal content>20% by volume. CRMC 100 electrical conductivity increases as volume % of the metal increases. The preferred metal content of the composite particle flowable medium 142 for ceramic bodies requiring suitable electrical conductivity, for example, for use in an AIMD, ranges between >20 volume % to ≤99 volume %.

To achieve suitable CRMC 100 solderability after forming a hermetically sealed ceramic body with CRMC 148, the preferred metal content of the composite particle flowable medium 142 is ≥25% by volume. The 25% volume % minimum was established when the inventors discovered that co-sintering temperatures>1,000° C. can cause a glass or ceramic skin to form on the surface of the CRMC 100 due to the glass or ceramic being incorporated within the metal. Once incorporated within the metal, the glass or ceramic then migrates through the metal to redeposit on the surface of the CRMC 100. As glasses and ceramics are generally not wettable by common solders, the redeposited glass or ceramic undesirably destroys the solderability of the surface of the CRMC 100. The inventors demonstrated the creation of a ceramic skin on the surface of CRMC 100 by co-sintering a Pt and $Al_2O_3$ composite particle flowable medium 142 disposed within a via of an $Al_2O_3$ ceramic test coupon. Co-sintering was conducted at 1,550° C. The inventors established that, when the Pt metal content of the composite particle flowable medium 142 disposed within the via of the $Al_2O_3$ ceramic test coupon was <25 volume %, an alumina ceramic skin was consistently formed on the surface of the CRMC 100. More importantly, because of the alumina ceramic skin, the inventors were consistently unable to make a solder attachment to the CRMC 100 surface. In contrast, when the inventors increased the Pt metal content of the $Pt/Al_2O_3$ composite particle flowable medium 142 to ≥25 volume %, the surface of the CRMC 100 of every test sample was devoid of the ceramic skin. Most importantly, the CRMC 100 of every sample devoid of the alumina ceramic skin was consistently solderable, with solder attachments consistently being made successfully.

The solvent of STEPS 1 and 2 may be selected from the group consisting of: an alcohol, a hydrocarbon, and water. Examples of solvents besides water include, but are not limited to, butynol, butyl carbitol, ethanol, ethylene glycol, diethylene glycol, glycerol, methanol, propanol, propylene glycol, methyl ethyl ketone, terpineol, benzene, cyclohexane, heptane, hexane, n-octyl alcohol, toluene, xylene and combinations thereof. AS disclosed, optional additives may also be added to the solvent.

The optional additives of STEPS 1 and 2 may comprise one of an inhibitor, a modifier, a dispersant, a surfactant, a plasticizer, a binder and combinations thereof. Inhibitors may be used to delay, slow or prevent an undesirable result or enable a desirable outcome. For example, inhibitors may be used to selectively alter or prevent sintering of a material, such as, to delay particle sintering, inhibit particle sintering, or encourage regional particle sintering while at the same time inhibiting particle sintering outside of the region. Inhibitors may also be used to accelerate or deaccelerate material grain growth, thereby precisely controlling the density and porosity of the resultant sintered body. Dispersants and surfactants wet and disperse fine powders and may be used for rheology control. Dispersants and surfactants can help to decrease viscosity and help achieve a narrow particle size distribution by reducing agglomeration. Inhibitors may be mechanical, chemical or thermal. Modifiers influence the physical, chemical, electrochemical, optical, electrical, and transport properties of a material. Plasticizers promote plasticity and flexibility of a material. Plasticizers may be selected from the group consisting of phosphorated plasticizers, chloroparaffins, phthalates, adipates, sebacates and combinations thereof.

Suitable dispersants and surfactants of STEPS 1 and 2 include, but are not limited to, polymeric polyelectrolytes, such as those based on acrylic acid, including sodium and/or ammonium salts, e.g., NARLEX LD-42 and LD-45, available from National Starch Co., Bridgewater, N.J., and DARVAN C and 821A, available from R.T. Vanderbilt & Co., Norwalk, Conn., sodium, potassium, or ammonium polyphosphates and pyrophosphates, amines, such as di- or tri-alkylamines, e.g., diethylamine, tripropylamine, di- or trialkanolamines, e.g., triethanolamine, N,N-diethyl-ethanolamine, polyethylene imines, e.g., Corcat P-600 (MW=600,000) and Corcat P-12 (MW=12,000), available from Virginia Chemical, Portsmouth, Va., morpholine, and other amine dispersants known in the art. Polyelectrolytes including quaternary ammonium salts, e.g., EMCOL CC-55 and CC-42, available from Witco Chem. Corp., Houston, Tex.; polyethylene glycols and polyoxyalkylene derivatives of propylene glycol, e.g., Pluronic L-12, available from BASF Corp., Parsippany, N.J., polyvinylpyrrolidone, vinylacetates, and the like, and compatible mixtures thereof, are also contemplated.

Suitable binders of STEPS 1 and 2 may be selected from the group consisting of ethyl cellulose, acrylic resin, polyvinyl alcohol, polyvinyl butyral and a poly(alkylene carbonate) having the general formula R—O—C(═O)—O with $R=C_1$ through $C_5$. Poly(ethylene carbonate) or polypropylene carbonate) are preferred poly(alkylene carbonates).

FIG. 7 is the flow chart for STEP 3, which forms a hermetically sealed ceramic body with CRMC 148. The composite particle flowable medium 142 is disposed on, through and/or within a green-state (pre-sintered) ceramic body 144. The green state ceramic body 144 may be a single layer ceramic body, a single construct ceramic body, or a multilayer ceramic body. Green state ceramic bodies 144 may be formed using any current ceramic forming technologies. Green state multilayer ceramic body may be made by forming "n" number of ceramic single layers or sheets that are then stacked and laminated, for example, by applying pressure.

Alternatively, a monolithic green state ceramic body 144 of the present invention may be formed by one of powder compacting, injection molding, tape casting, slip casting, mold casting, additive manufacturing, 3D printing, lamination, among others. Additional methods for forming green state ceramic bodies 144 are disclosed in U.S. Pat. No. 8,653,384 (now RE47,624); U.S. Pat. Nos. 8,938,309; 9,233,253; 9,352,150; 9,463,329; 9,492,659; 9,511,220; 9,889,306; 9,993,650; 10,046,166; 10,249,415; 10,272,252; 10,272,253; 10,420,949; 10,500,402; 10,559,409; 10,881,867; 10,857,368; 11,071,858; and 11,198,014, which are all assigned to the present assignee, the contents of which are fully incorporated herein by these references. The composite particle flowable medium 142 and the green state ceramic body 144 are then co-sintered 146 to form the hermetically sealed ceramic body with CRMC 148.

Figures 8, 9:
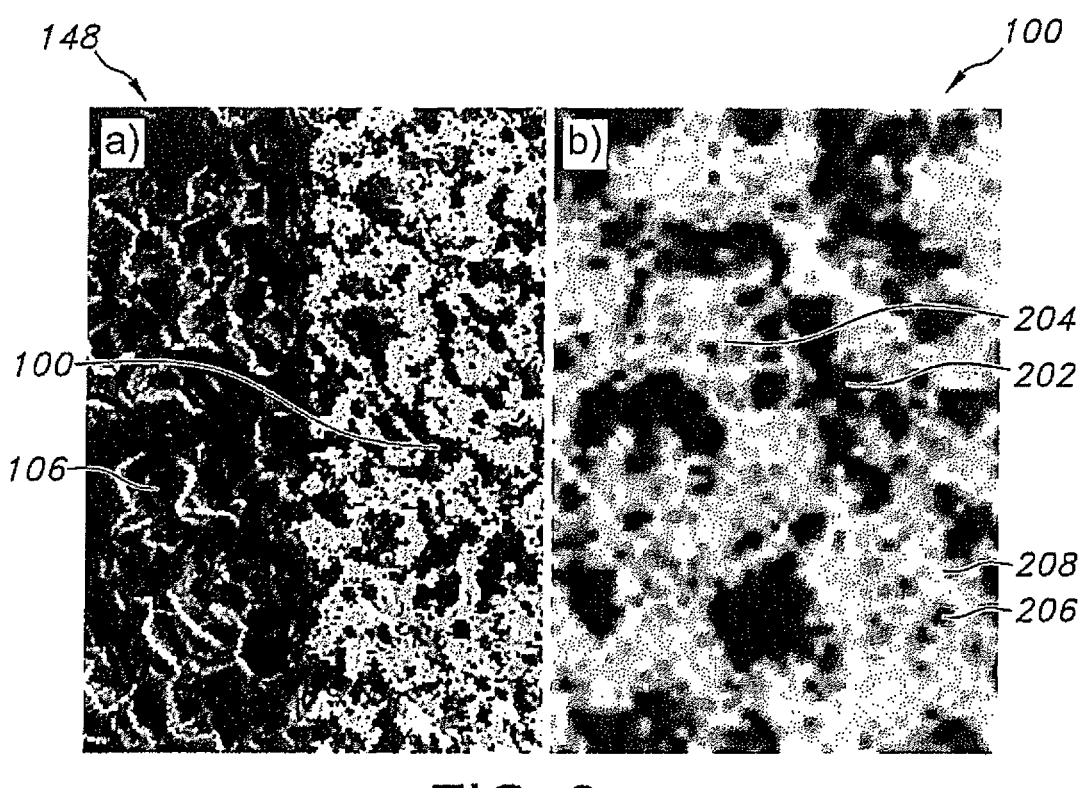
FIG. 8 is a spilt SEM image of a hermetically sealed ceramic body showing the CRMC at two different magnifications.
FIG. 9 is a spilt SEM image of a ceramic body showing a prior art cermet at two different magnifications.
Figure 10:
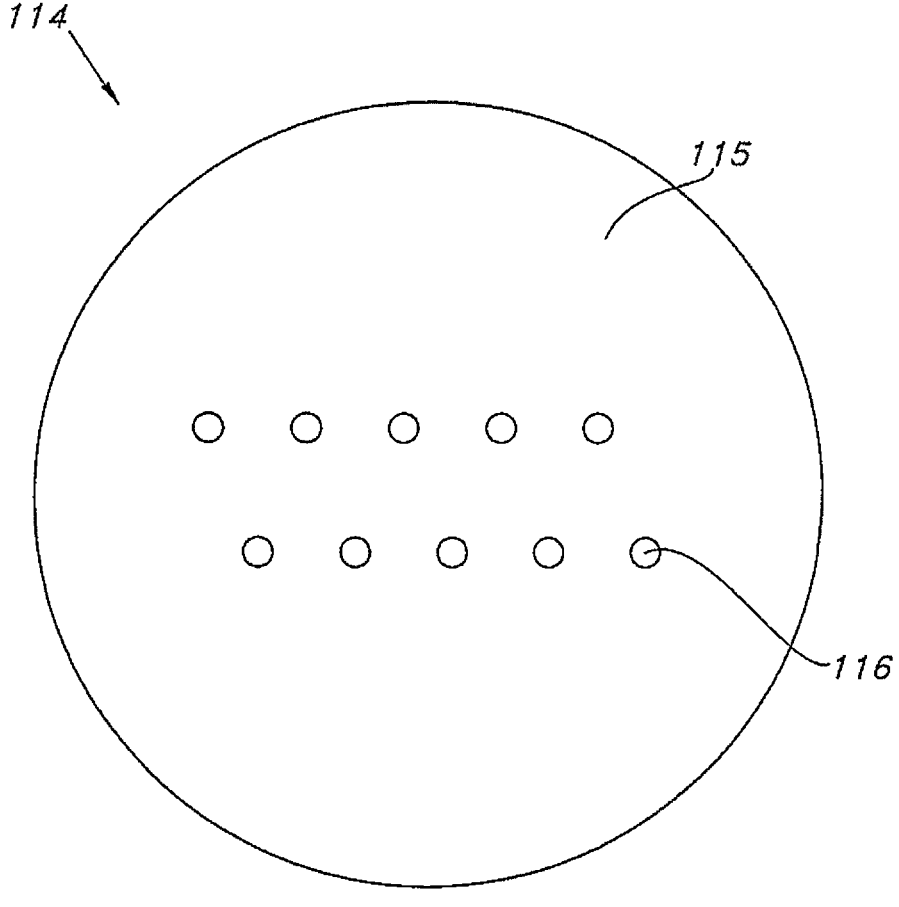
FIG. 10 is top view of a test coupon having hermetically sealed CRMC solid via electrical conductors.

FIG. 8 is a split SEM image of (a) a hermetically sealed ceramic body with CRMC 148; and (b) an enlarged view of the CRMC 100 of the present invention. The ceramic body 106 of the hermetically sealed ceramic body with CRMC 148 is $Al_2O_3$. The CRMC 100 comprises a metal matrix composite 204 and a ceramic matric composite 202. The hermetically sealed ceramic body with CRMC 148 was made using a $Pt/Al_2O_3$ composite particle flowable medium 142, which was prepared from a $Pt/Al_2O_3$ composite particle powder 138. The composite particles 112 of the composite particle powder 138, as previously disclosed by FIG. 5, comprise adhered Pt metal 104 and $Al_2O_3$ ceramic 102. The $Pt/Al_2O_3$ composite particle flowable medium 142 of FIG. 8 comprises 38 volume % of the $Pt/Al_2O_3$ composite particle powder 138 and 62 volume % solvent and optional additives 122, the additives being a polymeric dispersant, a cellulose based binder and a sintering inhibitor. The $Pt/Al_2O_3$ composite particle flowable medium 142 was disposed in each of ten (10) drilled vias 116 of a monolithic $Al_2O_3$ test coupon 114, as illustrated by FIG. 10. Each via diameter of the monolithic $Al_2O_3$ test coupon 114 was 0.013 inch with a length of 0.030 inch. Forty-eight monolithic $Al_2O_3$ test coupons 114 having $Pt/Al_2O_3$ composite particle flowable medium 142 disposed in each via were then co-sintered to form a ceramic body with CRMC 148 (48 $Al_2O_3$ ceramic test coupons having 10 electrically conductive vias each provide a total of 480 hermetically sealed $Pt/Al_2O_3$ CRMC 100 solid via electrical conductors).

The hermetically sealed monolithic $Al_2O_3$ test coupon 114 comprising solid $Pt/Al_2O_3$ CRMC 100 solid via electrical conductors were subjected to immersion testing in phosphate buffered saline (PBS) at 60° C. for up to 4,000 hours. Twelve (12) evaluation samples were helium leak tested at 1,000, 2,000, 3,000 and 4,000 hours using a Varian leak tester. As each monolithic $Al_2O_3$ test coupon 114 has ten (10) hermetically sealed solid $Pt/Al_2O_3$ CRMC 100 vias, each of the four (4) groups of 12 evaluation samples provided hermeticity test results for 120 hermetically sealed $Pt/Al_2O_3$ CRMC 100 solid via electrical conductors. Every hermetically sealed via in each evaluation group retained hermeticity after immersion testing, each group measuring leak rates ranging between 0.2 to $3.4\times10^{-10}$ std cc He/s.

FIG. 9 is a split SEM image of a prior art cermet taken from a paper entitled "Advanced CerMet Ceramic Composites for Medical Applications, authored by Robert Dittmer et al., and published in the Journal of the Mechanical Behavior of Biomedical Materials 75 (2017) 206-211. The split SEM image of FIG. 9 exhibits (a) a prior art CerMet-ceramic composite 500 having an insulating ceramic matrix 510 and a CerMet conductor 520, and (b) an enlarged view of the CerMet conductor 520. The paper discloses that the insulating ceramic matrix 510 is an alumina ceramic matrix 530, and the CerMet conductor 520 has platinum metal 540 and alumina ceramic 550. The authors disclose that the CerMet-ceramic samples of FIG. 9 were made using a CerMet paste having platinum particles and alumina particles with a hydrophilic ether-based binder and ester alcohols as solvents. The CerMet paste is then pushed through a stencil into cavities formed by punching a ceramic green layer of a tape; stacking and laminating multiple CerMet paste-filled layers; and then co-firing the multiple stacked and laminated CerMet paste-filled layers to form the CerMet-ceramic composite 500. The authors disclose that the as-manufactured CerMet-ceramic composite samples have a leak rate less than $1\times10^{-12}$ mbar L s$^{-1}$, which was sustained after thermal cycle testing between −60° C. to 200° C. for 80 cycles.

Referring again to FIGS. 8 and 9, when the microstructure of FIG. 8 is compared to the microstructure of FIG. 9, striking distinctions are observed. The first striking distinction is that the CRMC 100 of FIG. 8 comprises an electrically conductive metal matrix composite 204 within which ceramic particles 206 are embedded (in other words, the CMC is a ceramic particle reinforced metal composite). In contrast, the CerMet conductor 520 of FIG. 9 basically only comprises Pt 540. There is no reinforcement. The second striking difference is that the CRMC 100 of FIG. 8 comprises a ceramic matrix composite 202 within which metal-containing particles 208 are embedded. In contrast, the CerMet conductor 520 of FIG. 9 only basically comprises $Al_2O_3$ ceramic 550. There is no metal-based particle reinforcement.

FIG. 10 is a schematic of a test coupon 114 used to evaluate the hermeticity of a hermetically sealed ceramic body with CRMC 148. The test coupon 114 comprises an $Al_2O_3$ ceramic disc 115 having CRMC 100 solid via electrical conductors 116. As previously disclosed, the diameter of the test coupon solid via electrical conductor 116 is 0.013 inch and the length is 0.030 inch. After immersion testing up to 4,000 hours, the measured leak rate ranged between 0.2 to $3.4\times10^{-10}$ std cc He/s.

Figures 11, 12:
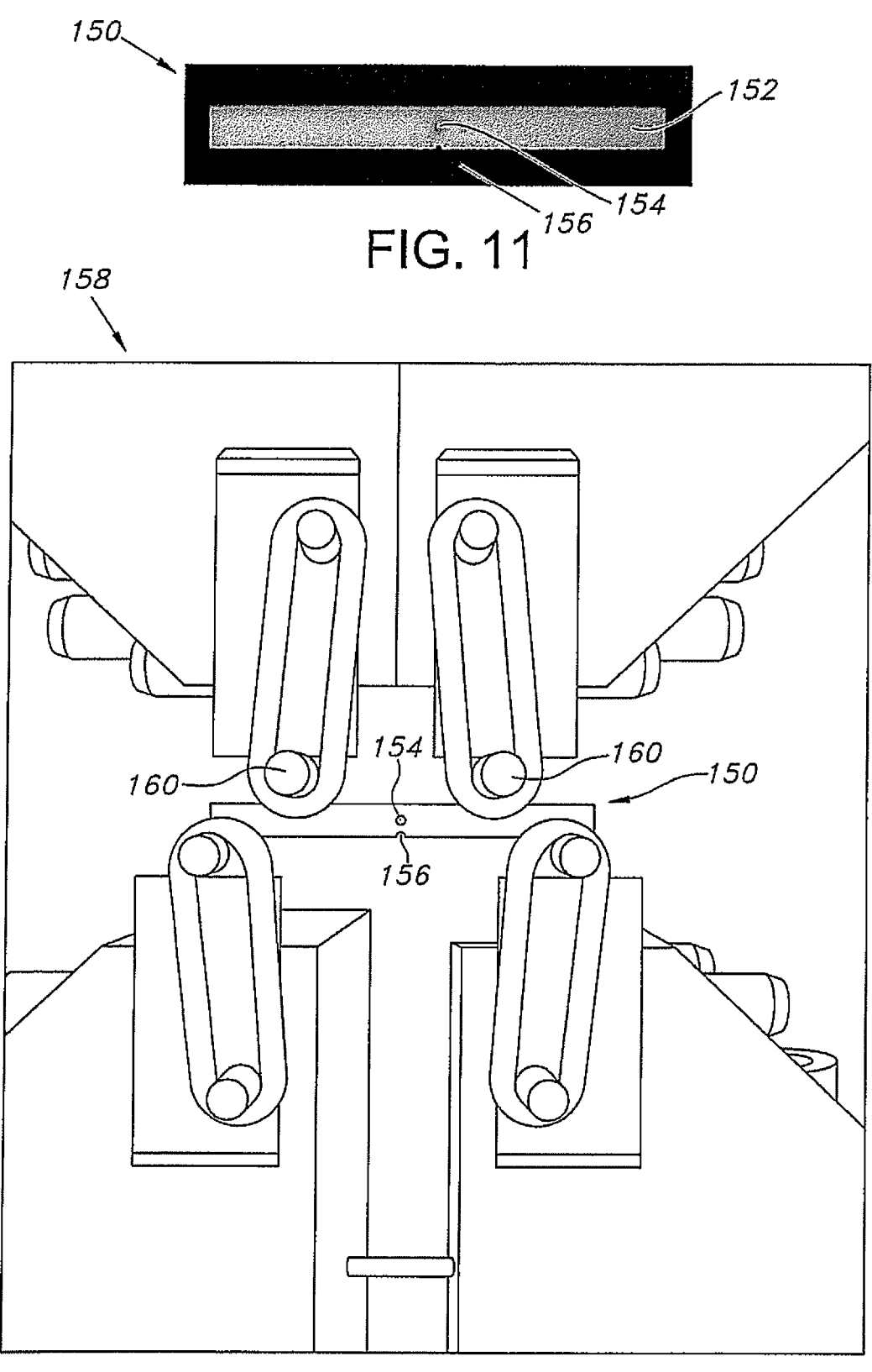
FIG. 11 is a photograph of a ceramic test bar having a solid CRMC via.
FIG. 12 is photograph of the ceramic test bar of FIG. 11 inserted into a four-point-¼ point bend test fixture.

FIG. 11 is a photograph of a ceramic test bar 150 comprising a ceramic beam 152 comprising $Al_2O_3$ and a central solid via 154 comprising the CRMC 100 of FIG. 8. The diameter of the CRMC 100 solid via 154 is 0.33 mm (0.013 in.). The $Al_2O_3$ ceramic beam 152 is rectangular and is sized in accordance with Specimen Table 3 Size A of ASTM C1161-13, that is, 2.0 mm wide, 1.5 mm thick, 25 mm long (0.08 in. wide, 0.06 in. thick, 1 in. long). ASTM C1161-13 generally describes the apparatus, specimen requirements, test procedure, calculations, and reporting requirements for testing the flexural strength of advanced ceramics in ambient temperature. The $Al_2O_3$ ceramic beam 152 of FIG. 11 has a notch 156 longitudinally aligned with the vertical diameter of the CRMC 100 solid via 154. It is inherently difficult to reliably measure the fracture resistance of brittle materials as the test method must create a stress state that approximates pure shear. The notch 156 facilitates fracture resistance measurement of the brittle ceramic test bars 150 by providing a stress concentration at or near the notch tip to ensure that a crack initiates in the loading direction. Accordingly, four-point bend testing was conducted on eighteen (18) ceramic test bars 150, each test bar 150 being subjected to loading followed by fracture path analysis.

Referring to the CerMet-ceramic composite of FIG. 9, the authors disclose that the mechanical strength of the CerMet-ceramic composite was evaluated by three-point bend testing. The three-point bending stage has a support width of 12 mm (0.5 in.). The test samples were 6 mm wide, 1.1 mm thick, 16 mm long (0.23 in. wide×0.04 in. thick×0.6 in. long). Each sample had five conductive pathways, each having a 300 μm (0.012 in.) diameter vertical interconnect access (VIA). There was no assessment of fracture path or any disclosure on the effects of three-point bending at the interface between the CerMet and the ceramic. Only the mechanical strength of the CerMet-ceramic composite compared to a pure ceramic without any VIAs was reported. As increased flexural strength is reported for the CerMet-ceramic composite without fracture path data or analysis, no correlation between hermeticity and flexural strength can be made.

FIG. 12 is a schematic of a four-point-¼ bend test fixture 158 in which the ceramic test bar 150 of FIG. 11 is inserted. The construct of the four-point-¼ bend test fixture 158 complies with the requirements set forth by the international standard ASTM C1161-13. The four-point bend test used to assess fracture path assures that maximum flexural stress is spread over the portion of the ceramic test bar 150 between loading pins 160. The CRMC 100 solid via 154 of the ceramic test bar 150 is centrally positioned between the loading pins 160 so that the solid via 154 is in the center between the loading pins 160 and in-line with the notch 156 of the ceramic test bar 150 to ensure that a crack initiates in the loading direction. By ensuring that crack initiation is in the loading direction, the effect of stress at the solid via 154 can be determined. Analysis of the fracture path 162 provides insight into the strength of the interface between the solid material hermetically sealed within the via 154 and the ceramic beam 152. Thereby, when the loading pins 160 apply the load, crack propagation initiates from the notch 156, and propagates in the loading direction approaching the solid via 154, before finally traversing the full width of the ceramic test bar 150. In this way, both the flexural strength of the ceramic test bar 150 can be measured, and the fracture strength of the interface between the solid via 154 and the ceramic beam 152 can be evaluated. The measured flexural strength also provides insight into the tendency for premature failure of a test specimen having a ceramic body having a solid via therewithin. Resistance to premature failure is determined by examining the combination of the stable region during loading (before crack formation and propagation); the crack propagation path of the test specimen; and the morphology of the fracture.

Figure 13:
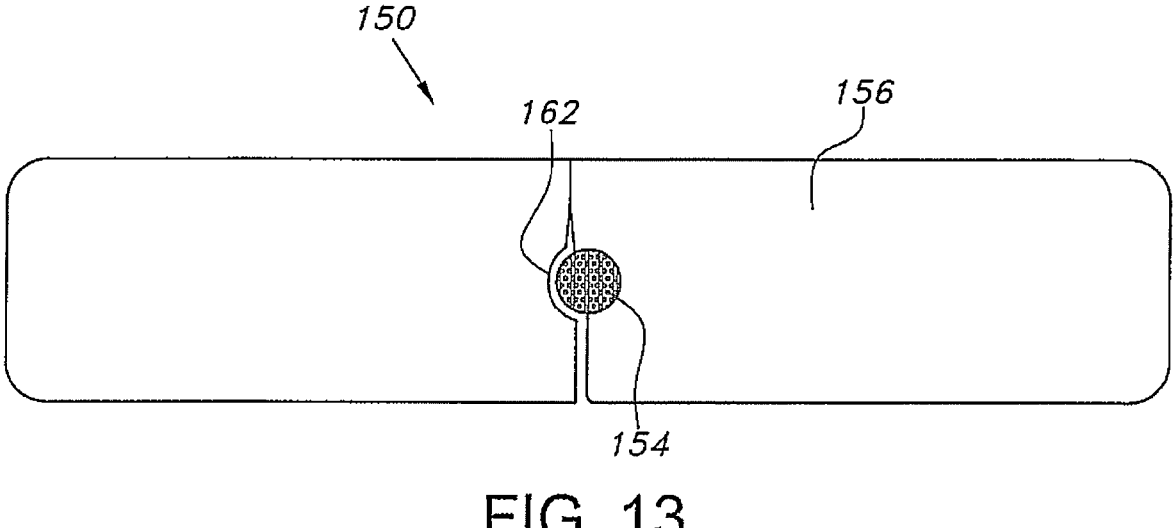
FIG. 13 is an illustration of an undesirable fracture path.

FIG. 13 is an illustration of an undesirable fracture path 162 that can be formed through a ceramic test bar 150 having a solid via 154 during four-point-¼ bend testing. The fracture path 162 illustrated propagates through the body of the ceramic test bar 150 from the notch 156 to and around the solid via 154, along the interface between the solid via 156 and the ceramic beam 152, and across the full width of the ceramic beam 152, which spans from the notched edge to the opposite edge of the ceramic test bar 150. Such a fracture path 162 indicates that the interface between the solid via 156 and the ceramic beam 152 has lower fracture strength in comparison to the test beam parent materials, namely, the ceramic beam 152 and the solid via 154 materials. The lower fracture strength at the joining interface between the ceramic beam 152 and the solid via 154 indicates weak bonding therebetween. Such fracture paths 162 are always undesirable for interfaces intended to impart and retain hermeticity, as weak interfacial bonding can potentially result in potentially dangerous unpredictable hermeticity loss.

Figure 14:
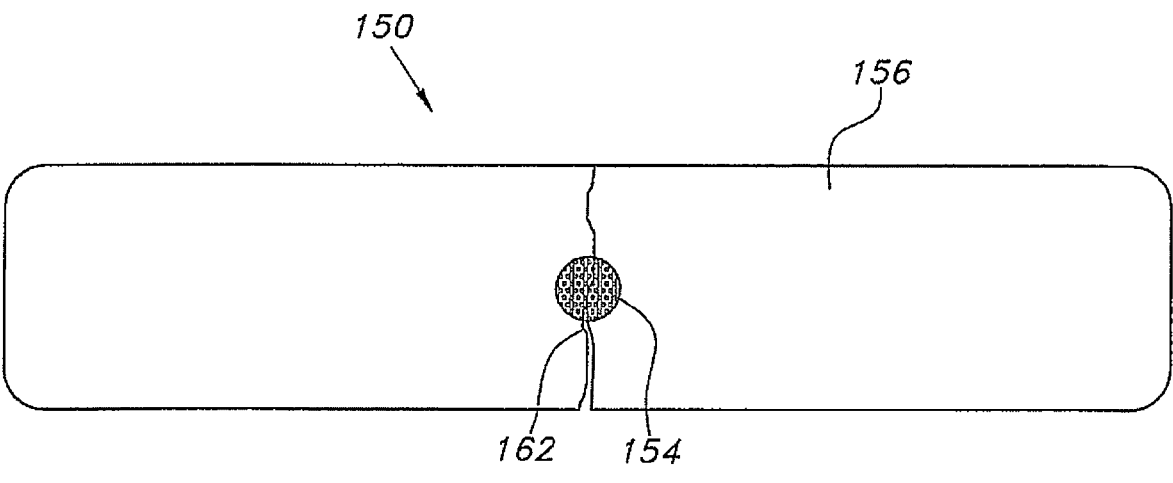
FIG. 14 is an illustration of a desirable fracture path.

FIG. 14 is an illustration of a preferred fracture path 162 that can be formed through a ceramic test bar 150 having a solid via 154 during four-point-bend testing. The fracture path 162 illustrated propagates through the body of the ceramic test bar 150, from the notch 156, passing through the interface between the solid via 156 (which is the fracture entry point into the solid via electrical conductor) and the ceramic beam 152, traversing the full diameter of the solid via 154, then again passing through the interface between the solid via 156 and the ceramic beam 152 (which is the fracture exit point from the solid via electrical conductor), to traverse the full width of the body of the ceramic beam 152 (which spans from the notched edge to the opposite edge of the ceramic test bar 150). Such a fracture path indicates that the interface between the solid via 156 and the ceramic beam 152 has higher fracture strength in comparison to the test beam parent materials, namely, the ceramic beam 152 and the solid via 154 materials. The higher fracture strength indicates strong bonding at the joining interface of the ceramic beam 152 and the solid via 154. Such fracture paths are always desirable for interfaces intended to impart and retain hermeticity, as unpredictable hermeticity loss is generally not an issue when fractures propagate directly through mating dissimilar material interfaces.

More importantly, because an implanted medical device is required to sustain hermeticity over the operating life of the implant, when an implanted medical device comprises a ceramic body 106 with a solid via 154 that has a higher interfacial fracture strength, the medical device characteristically can retain hermeticity over its useful implant life. Thus, fracture propagation paths traversing dissimilar material interfaces indicate a robust interface capable of sustained hermeticity. Sustained hermeticity over the operational or service life of an implanted device or system is critical, as without sustained hermeticity, an implant patient is exposed to dangerous risk, which can be life-threatening, particularly if the patient depends on the therapy delivered by the implanted device. As previously provided, pacemaker dependent implant patients cannot live without the pacemaker. If the implanted pacemaker loses hermeticity, body fluids can enter inside of the pulse generator of the pacemaker. The body fluids can cause the electronics of the pacemaker to fail. If the electronics fail, then electrical stimulation therapy cannot be delivered to the heart. If electrical stimulation therapy cannot be delivered to the heart of a pacemaker dependent patient, the heart may stop beating and the pacemaker dependent patient could very well die.

Figure 15:
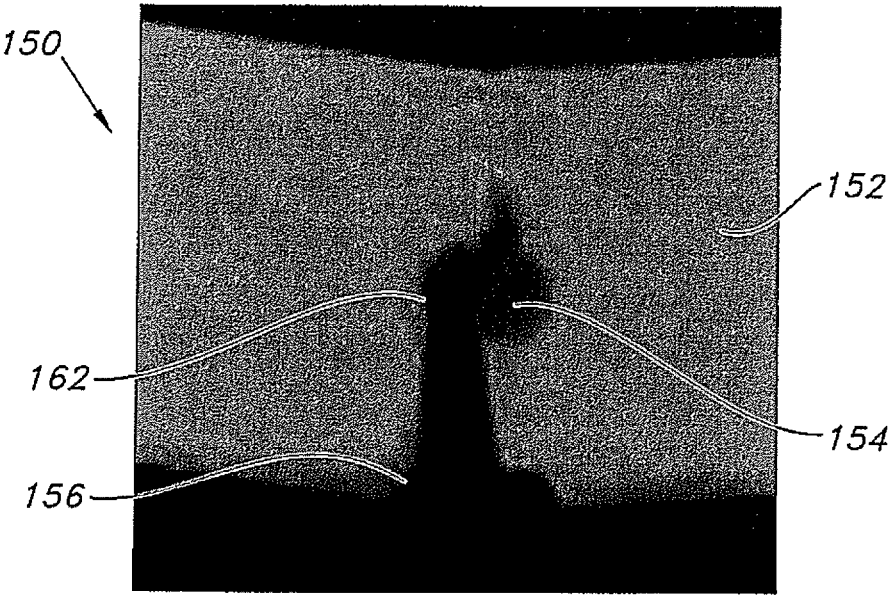
FIG. 15 is a photograph of a ceramic test bar having an undesirable fracture path.

FIG. 15 is an optical microscope photograph of an actual ceramic test bar 150 having an undesirable fracture path 162. The design and four-point bend testing of the ceramic test bar 150 of FIG. 15 are in accordance with ASTM C1161-13. The fracture path 162 demonstrates that a crack can propagate from the notch 156 and about the interface of a solid via 154 into the body of the ceramic beam 152. The inventors have observed that ceramic test bars 150 having an Al$_2$O$_3$ ceramic beam 152 and a prior art cermet solid via 154 with a microstructure similar to the prior art CerMet-ceramic composite 500 of FIG. 9 can exhibit the undesirable fracture path 162 represented by FIG. 13.

Figure 16:
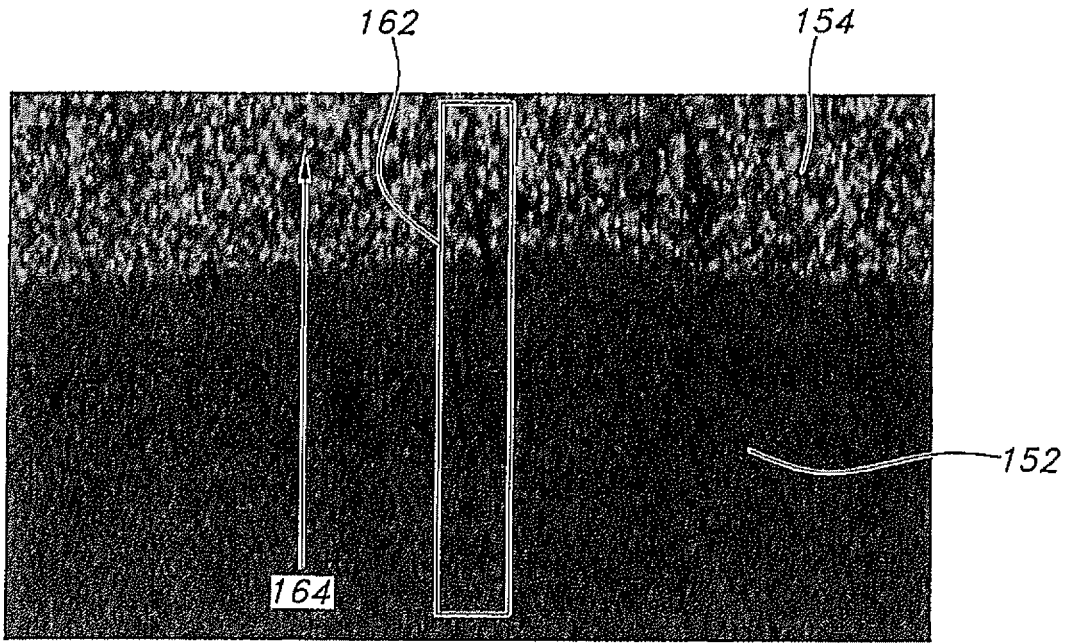
FIG. 16 is a SEM image of a desirable fracture path formed during four-point-¼ bend testing.

FIG. 16 is a SEM image of a desirable fracture path 162 traversing a CRMC/Al₂O₃ interface of a ceramic test bar 150, also designed in accordance with ASTM C1161-13. The solid via 154 is the CRMC 100 of the present invention (as previously shown by the hermetically sealed ceramic body with the CRMC 148 of FIG. 8). The test bar 150 of FIG. 16 was subjected to the ASTM C1161-13 four-point bend test using the testing fixture of FIG. 12. The arrow shows the direction of crack propagation 164 of the fracture path 162, which is highlighted by the rectangular box. The fracture path 162 traverses the interface of the solid via 154 of CRMC 100 and the ceramic beam 152 of Al₂O₃ ceramic. The inventors have observed that ceramic test bars 150 having a ceramic beam 152 that is an Al₂O₃ ceramic and a solid via 154 that is CRMC 100, consistently exhibit the preferred fracture path 162 of FIG. 14. Notably, all 18 of the ceramic test bars 150 of FIG. 11 tested using the test fixture of FIG. 12 exhibited the same direction of crack propagation 164 and the preferred fracture path 162 of FIG. 16.

Further regarding fracture paths, of particular significance is that the CRMC 100 of the present invention consistently exhibited the preferred fracture path 162 of FIG. 14, that is entering and traversing the CRMC/Al₂O₃ interface, passing through the CRMC 100, then exiting the CRMC 100 by traversing once again through the CRMC/Al₂O₃ interface. There were no test samples that exhibited fracture propagation along any length of the CRMC/Al₂O₃ interface. Of significance is that the only difference between the CRMC of the present invention of FIG. 8 and the prior art cermet, such as the CerMet-ceramic composite 500 of FIG. 9, is the conductive paste used to form their respective electrical conductors. The CRMC 100 of FIG. 8 is formed by co-sintering a Pt/Al₂O₃ composite particle flowable medium 142 and an Al₂O₃ ceramic body 106, while prior art cermets, such as the CerMet of FIG. 9, are formed by co-firing conductive pastes having mixed metal and ceramic particles; hence, the mixed metal and ceramic powders used to form the conductive paste provides an electrically conductive paste having discrete particles of metal and ceramic instead of an electrically conductive paste having a powder comprising the metal/ceramic composite particles of the present invention. As hermetic cermet-containing samples can fracture along the interface between the cermet and the ceramic, without a fracture path analysis after three-point bend testing, which permits evaluation of the microstructure and morphology of the materials along the fracture path, it seems that the authors may have erroneously concluded that leak-tight bonding between platinum and alumina is reflected in the mechanical parameters of the ceramic. Moreover, leak-tight bonding means that matter (solid, liquid, or gas) cannot escape or spill out from the bond, so it only relates to a leak rate. A leak-tight bond has nothing at all to do with the mechanical strength of anything. In other words, just because the CerMet-ceramic composite demonstrated a higher flexural strength with the CerMet solid via does not mean that the interface between the CerMet and the ceramic will sustain hermeticity for the life of an implanted medical device.

Regarding once again the composite particle flowable medium 142 of FIG. 8, a composite particle powder 138 is used to form an electrically conductive paste. The composite particles are formed by intentionally partially sintering a blend of ceramic and metal powders prior to grinding and sieving so that metal/ceramic composite particles comprising adhered metal 104 and a ceramic 102 are formed. Thus, the four-point-¼ bend testing establishes that the conductive pastes of the present invention made using composite particle powders having adhered metal 104 and ceramic 102 (in other words, the composite particle flowable medium 142 of the present invention) imparts mechanical strength to the interface between the CRMC and the ceramic body, which is demonstrated by preferred fracture path propagation traversing CRMC-ceramic interfaces.

Figure 17:
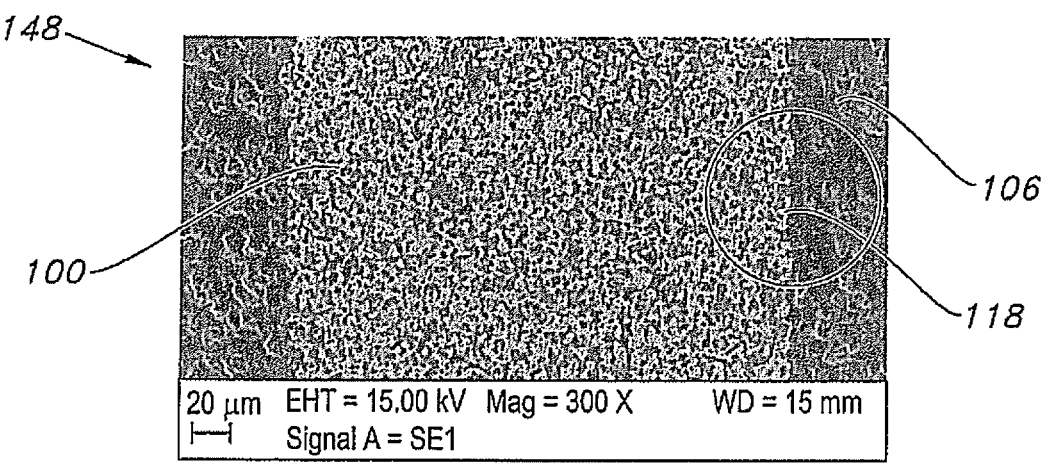
FIG. 17 is the SEM image of a hermetically sealed ceramic body with CRMC at 300×.
Figure 18:
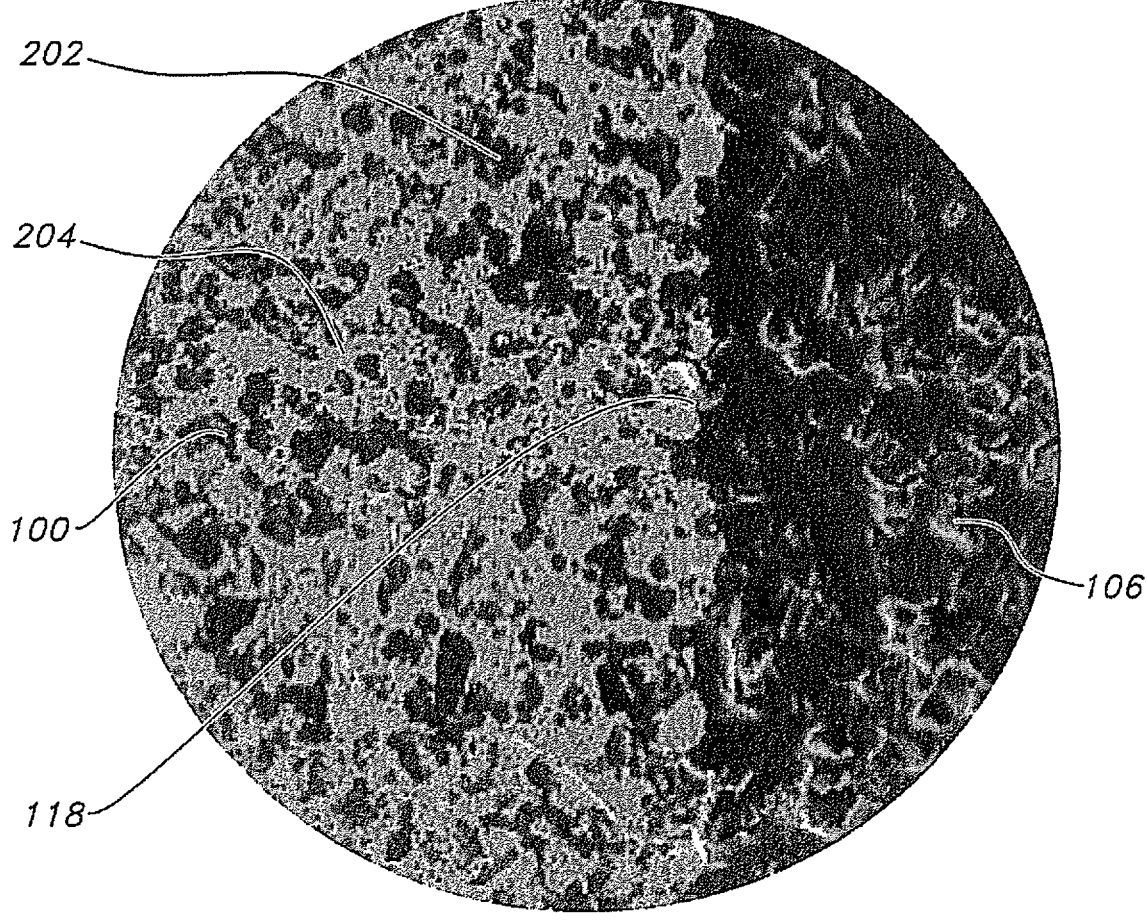
FIG. 18 is an enlarged view of the hermetically sealed ceramic body of FIG. 17 showing the interface between the ceramic body and the CRMC.

FIGS. 17 and 18 are SEM images of the CRMC 100 of the present invention. FIG. 17 is the SEM image of a hermetically sealed ceramic body with CRMC 148 at 300× magnification. FIG. 18 is an enlarged view of the interface 118 between the CRMC 100 and the ceramic body 106 encircled on the right of FIG. 17. Examination of FIG. 17 reveals that the CRMC 100 and the ceramic body 106 are in intimate contact at the interface 118. The enlarged view of FIG. 18 more clearly shows the interface 118 and that the CRMC 100 comprises a ceramic matrix composite 202 and a metal matrix composite 204.

Figure 19:
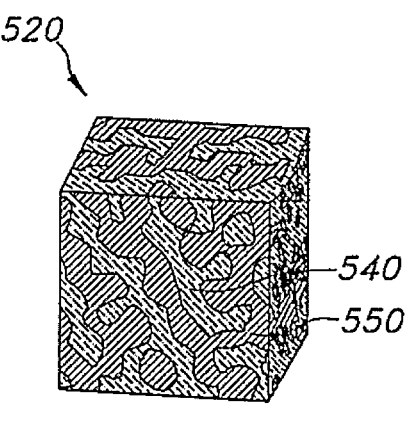
FIG. 19 is a model of a traditional prior art cermet.

FIG. 19 is a model of a traditional prior art cermet, similar to the CerMet-ceramic composite 500 of FIG. 9. The cermet model of FIG. 19 closely resembles the CerMet conductor 520 depicted by FIG. 9, and matches the description written in the Dittmer et al. paper. The cermet model of FIG. 19 shows an interpenetrating network incorporating a metal 540 and a ceramic 550. The CerMet technology implements conductive pathways (CerMet conductor 520) by a high-temperature co-fired ceramic (HTCC) method that provides vertical interconnect access of the metal 540 to the insulating ceramic matrix 510 of the CerMet-ceramic composite 500. The authors describe in their Results that the ceramic 550 of the interpenetrating network structure horizontally permeates the CerMet conductor 520, which allows the metal 540 to pervade vertically through the whole thickness of the CerMet conductor 520. The authors further describe in their Abstract that the CerMet electrical conductor 540 is not a single metallic phase but is a ceramic-metal mixture. The authors thereby specifically ascribe that the interpenetrating microstructure of the CerMet allows for a strong and hermetic integration of the electrical conductor into the ceramic matrix, which, otherwise, would be impossible to accomplish due to a metal and ceramic mismatch in thermal expansion.

Figure 20:
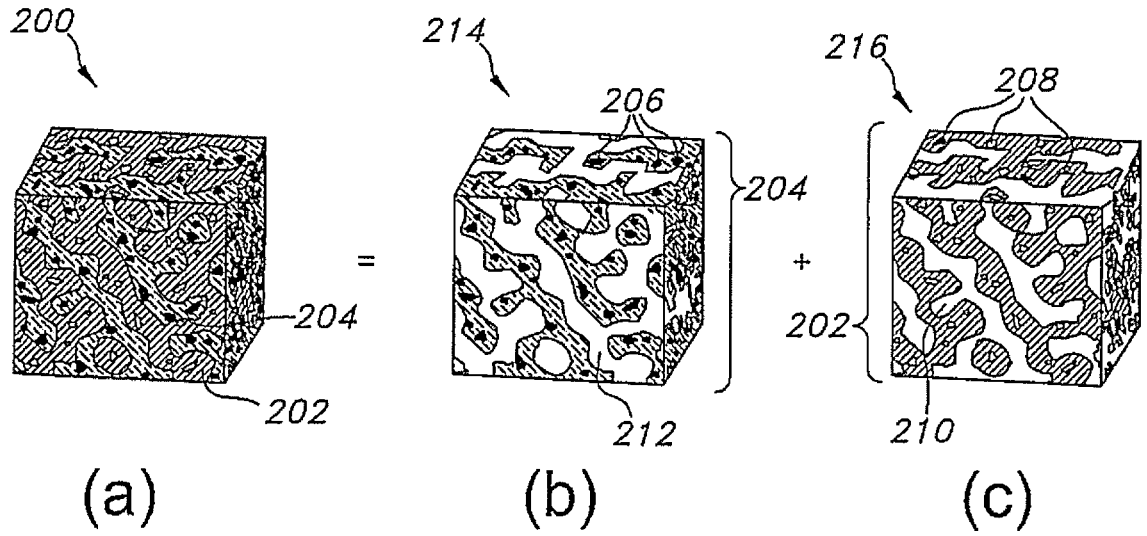
FIG. 20 is a model of (a) the CRMC of the present invention, including separate models of (b) the metal matrix composite (MMC) and (c) the ceramic matrix composite (CMC) of the CRMC.

FIG. 20 is a model of (a) the CRMC interpenetrating network 200, including separate models of (b) the metal matrix composite (MMC) interconnecting network 214 and (c) the ceramic matrix composite (CMC) interconnecting network 216. FIG. 20(*a*) shows that a the CRMC interpenetrating network 200 forms a composition composite, which incorporates a metal matrix composite (MMC) 204 and a ceramic matrix composite (CMC) 202. FIGS. 20(*b*) and 20(*c*) are extracted from the composition composite CRMC interpenetrating network 200 of FIG. 20(*a*). FIG. 20(*b*) shows that the MMC 204 has an interconnecting composite network 214 having reinforcing ceramic-based particles 206 embedded within a metal matrix 212. FIG. 20(*c*) shows that the CMC 202 has an interconnecting composite network 216 having reinforcing metal-containing particles 208 embedded within a ceramic matrix 210. Comparison of FIGS. 20(*b*) with 20(*c*) reveals that the MMC interconnecting network 214 conforms to the CMC interconnecting network 216.

Figure 21:
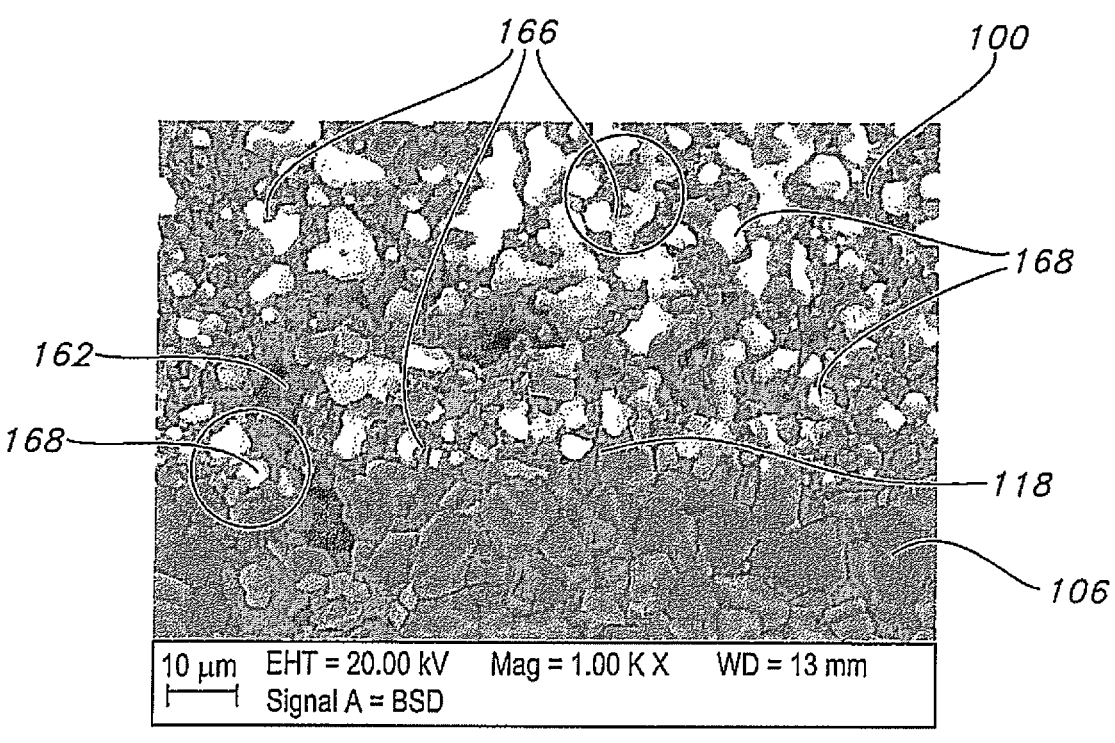
FIG. 21 is a SEM image of the CRMC of the present invention.

FIG. 21 is a SEM image representative of the CPMC 100 of FIG. 8. The CRMC 100 was formed using a Pt/Al₂O₃ composite particle powder 138 made in accordance with STEP 1 of FIG. 4 using the formulation of TABLE 2 below. Partial sintering was conducted at 450° C. The Pt/Al₂O₃ composite agglomerates were sieved using a 325 mesh, which resulted in a particle size of the Pt/Al$_2$O$_3$ composite particle powder 138 ranged from 1 μm to 50 μm. Less than 1% of the Pt/Al$_2$O$_3$ composite particle powder 138 comprised particles smaller than 1 μm. The CPMC 100 of the present invention may comprise composite particle powder 138 having a particle size ranging between ≥1 μm to ≤350 μm, with less than 1% of the particles being <1 μm.

TABLE 2

|  | Solution Components | Vol % |
|---|---|---|
| Solvent | (3.5:1 Terp:EC) Terpineol + EC | 24% |
| Alcohol | Terpineol | 20% |
| Additive | Sintering inhibitor | 15% |
| Additive | Dispersant | 2% |
| Ceramic Powder | Al$_2$O$_3$ powder | 20% |
| Metal Powder | Pt powder | 19% |

The Pt/Al$_2$O$_3$ composite particle powder 138 was then made into a Pt/Al$_2$O$_3$ paste composite particle flowable medium 142 in accordance with STEP 2 of FIG. 6 using the formulation of TABLE 3 below. The optional homogenization was also done.

TABLE 3

|  | Solution Components | Vol % |
|---|---|---|
| Solvent | (3.5:1 Terp:EC) Terpineol + EC | 36% |
| Alcohol | Terpineol | 23% |
| Additive | Dispersant | 3% |
| CRMC Powder | Pt/Al$_2$O$_3$ composite particle powder | 38% |

The hermetically sealed ceramic body with CRMC 148 was then made in accordance with STEP 3 of FIG. 7. The Pt/Al$_2$O$_3$ paste composite particle flowable medium 142 was disposed within a drilled via of a green state Al$_2$O$_3$ ceramic beam 152. The green state Al$_2$O$_3$ ceramic beam 152 and the Pt/Al$_2$O$_3$ paste composite particle flowable medium 142 were then co-sintered at 1,550° C.

Referring to FIG. 21, a preferred fracture path 162 that traverses the interface 118 between the CRMC 100 and the ceramic body 106 at 1,000× magnification is observable. Examination of the microstructure of the CRMC 100 reveals that the adhered metal and ceramic therewithin has two distinct morphologies. Notably, both mechanical interlocking 166 and chemical bonding 168 of the adhered metal and ceramic is observed in the CRMC 100 microstructure.

Figures 22, 23:
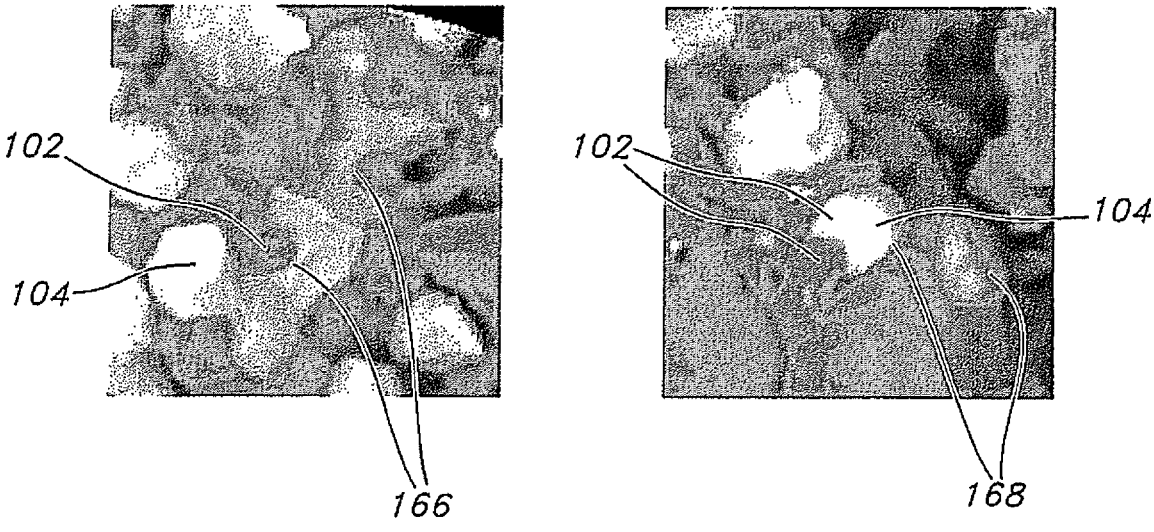
FIG. 22 is an enlarged view of the CRMC of FIG. 21 showing mechanically bonded metal and ceramic.
FIG. 23 is an enlarged view of the CRMC of FIG. 21 showing chemically bonded metal and ceramic.

FIG. 22 is an enlarged view of the CRMC 100 microstructure encircled on the left side of FIG. 21. The morphology of the adhered metal 104 and ceramic 102 is a mechanical interlocking 166, where the metal 104 conformally partially surrounds the ceramic 102 in a lock-and-key manner. In other words, the metal 104 and the ceramic 102 are physically locked to each other.

FIG. 23 is an enlarged view of the microstructure of the CRMC 100 encircled on the right side of FIG. 21. The morphology of the adhered metal and ceramic reveals chemical bonding 168, where the atoms of the metal 104 and the ceramic 102 are combined and held together by a strong combining force. In general, chemical bonding can be either covalent or ionic. Chemical elements that share electrons are covalently bonded. Chemical elements that have oppositely charged ions are ionically bonded by a strong attraction between the oppositely charged ions.

Figure 24:
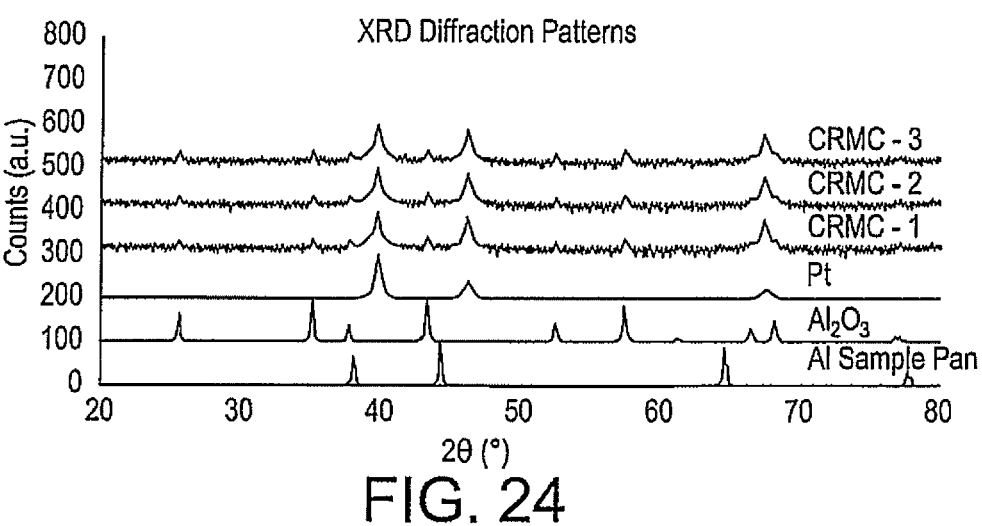
FIG. 24 is a graph of the CRMC acquired XRD patterns.
Figure 25:
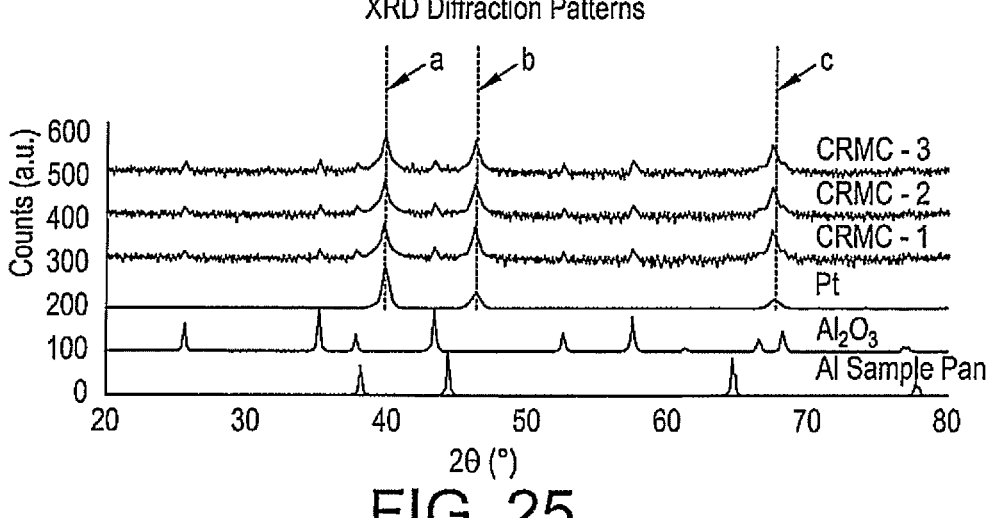
FIG. 25 is the graph of FIG. 24 with Pt reference sticks.
Figure 26:
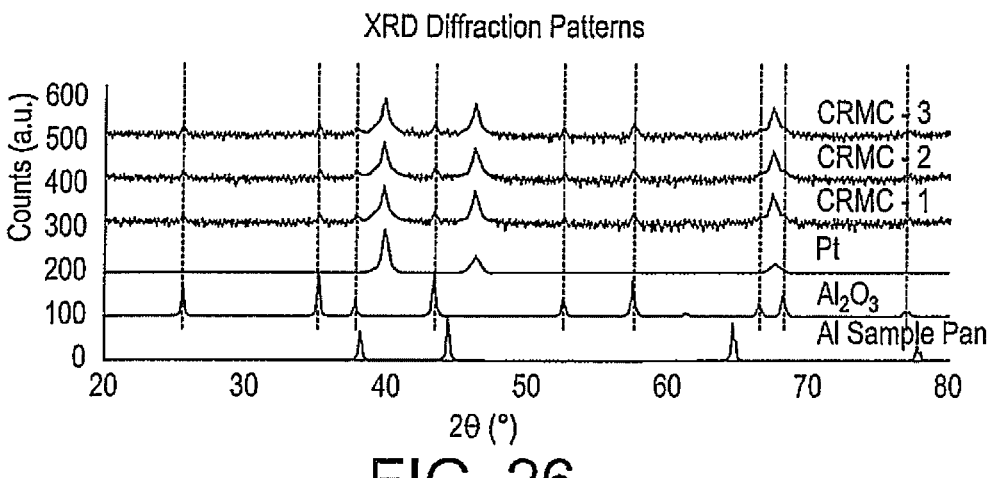
FIG. 26 is the graph of FIG. 24 with $Al_2O_3$ reference sticks.

FIGS. 24, 25 and 26 are graphs showing acquired X-ray diffraction (XRD) patterns. XRD patterns provide information on the structure of a solid material. XRD is a scattering technique where X-rays are scattered by the electrons of atoms present in a material without changing the material's wavelength. Since X-rays have wavelengths comparable to the interatomic spacing of a crystalline solid (between 0.2 nm and 10 nm), the incident X-ray beam diffracts in specific directions, in accordance with Bragg's law. The resulting diffraction pattern, given by the positions and intensities of the diffraction effects, is a fundamental physical property of a material, thus providing not only identification of the material elements or compounds, but it also defines its structure.

FIG. 24 provides the XRD patterns of Pt, Al$_2$O$_3$ and three CRMC 100 samples (CRMC-1, CRMC-2, and CRMC-3). XRD in each case was conducted using an aluminum (Al) pan. An XRD diffraction pattern of the Al pan was first acquired to remove any interference from being introduced to the references and the CRMC 100 samples. Individual XRD diffraction patterns of Pt and Al$_2$O$_3$ were separately acquired from the powders used to make the CRMC 100 samples. The reference powder particle size ranges between 0.1 μm and 10 μm. The individual Pt and Al$_2$O$_3$ diffraction patterns are used as references to which the CRMC 100 samples are compared. The Pt and the Al$_2$O$_3$ powders were loosely placed on the Al pan and spread flat with a straight edge before their respective XRD diffraction patterns were acquired.

Referring again to FIG. 24, examination of the acquired XRD patterns of the CRMC samples relative to the reference XRD diffraction patterns of Pt and Al$_2$O$_3$, the intensities of the Pt peaks of each CRMC sample is notably stronger than the intensities of the Al$_2$O$_3$ peaks. The intensities of the Al$_2$O$_3$ peaks are lower due to the much lower scattering efficiency of Al$_2$O$_3$ compared to Pt. Pt has much higher scattering efficiency than Al$_2$O$_3$, which actually dwarfs the scattering response of the Al$_2$O$_3$ such that some of the Al$_2$O$_3$ peaks are hard to discern. Nonetheless, XRD diffraction unquestionably establishes that the CRMC 100 samples evaluated comprise a Pt metal 104 and an Al$_2$O$_3$ ceramic 102.

FIG. 25 is the same graph as FIG. 24, except that three reference sticks a, b, and c were added. The three reference sticks a, b, and c dissect the Pt reference peaks through the tip of each peak so that the position and width of the CRMC sample peaks can be compared with the Pt reference peaks. The reference sticks a, b, and c show that the intensity peaks of all three CRMC samples align with the Pt reference, however, they have an apparent slight shift to the left, a sharper peak and decreased width. The apparent increased sharpness and decreased width suggests that the Pt of the CRMC has larger grains than the Pt reference material. The apparent slight shift to the left suggests that the Pt of the CRMC samples has increased tensile lattice strain compared to the Pt reference.

FIG. 26 is also the same graph of FIG. 24, except nine reference sticks are added. The nine reference sticks (unlabeled vertical dotted lines) now dissect the Al$_2$O$_3$ reference peaks through the tips of each peak for comparing the Al$_2$O$_3$ diffraction peaks of the CRMC samples relative to the Al$_2$O$_3$ reference. Although the Al$_2$O$_3$ diffraction peaks are weak, peak alignment with the Al$_2$O$_3$ reference is observable, which, as previously disclosed, confirms Al$_2$O$_3$ is present in the CRMC.

Figure 27:
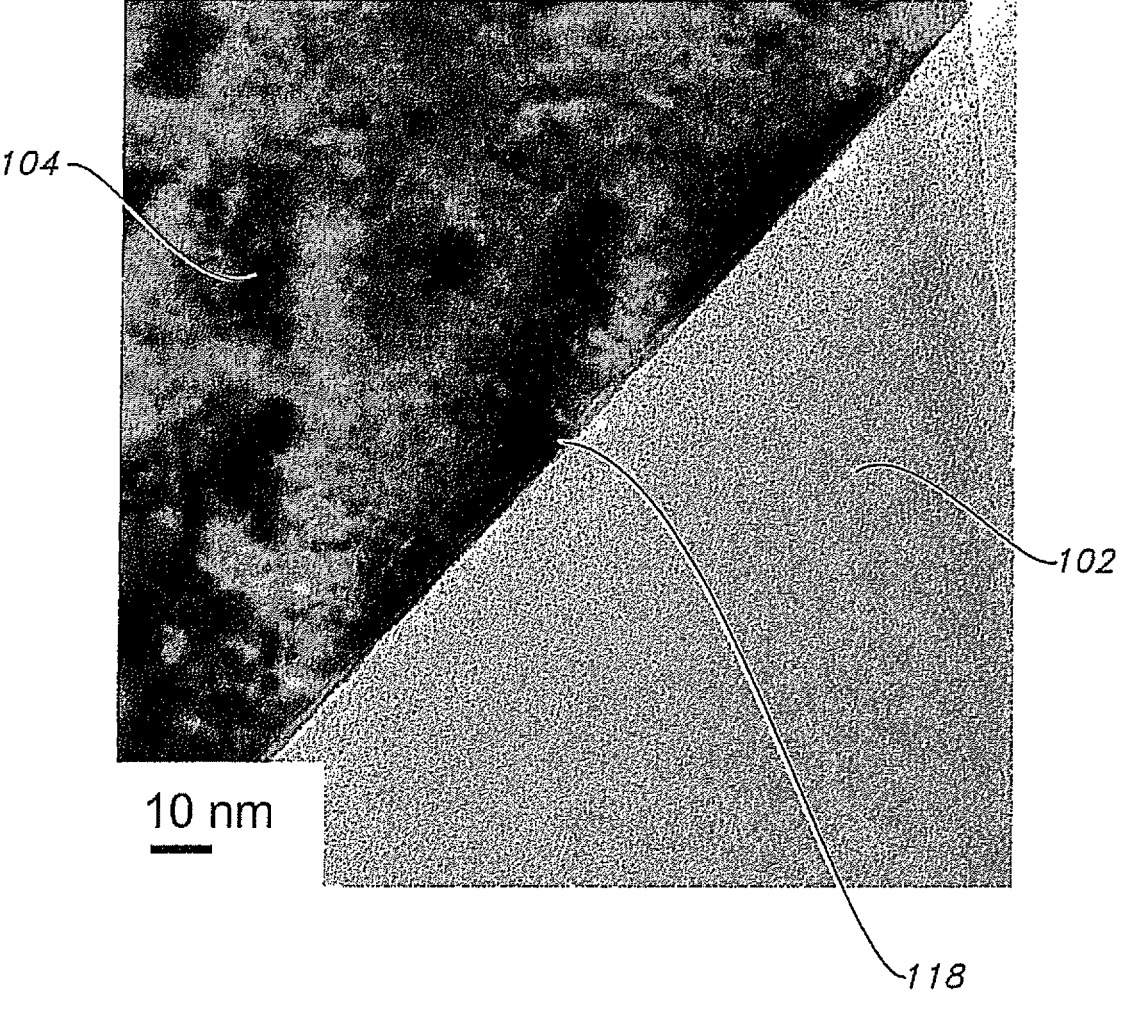
FIG. 27 is a transmission electron microscope (TEM) image of a Pt—$Al_2O_3$ interface.

FIG. 27 is a transmission electron microscope (TEM) image of the interface 118 between the adhered Pt metal 104 and $Al_2O_3$ ceramic 102 of the CRMC 100 of the present invention. The adhered Pt—$Al_2O_3$ interface 118 has a thickness ranging between 1.5 nm to 2 nm thick. The thickness of an adhered Pt and $Al_2O_3$ interface 118 may therefore range between ≥0.1 nm to ≤200 nm.

Figure 28:
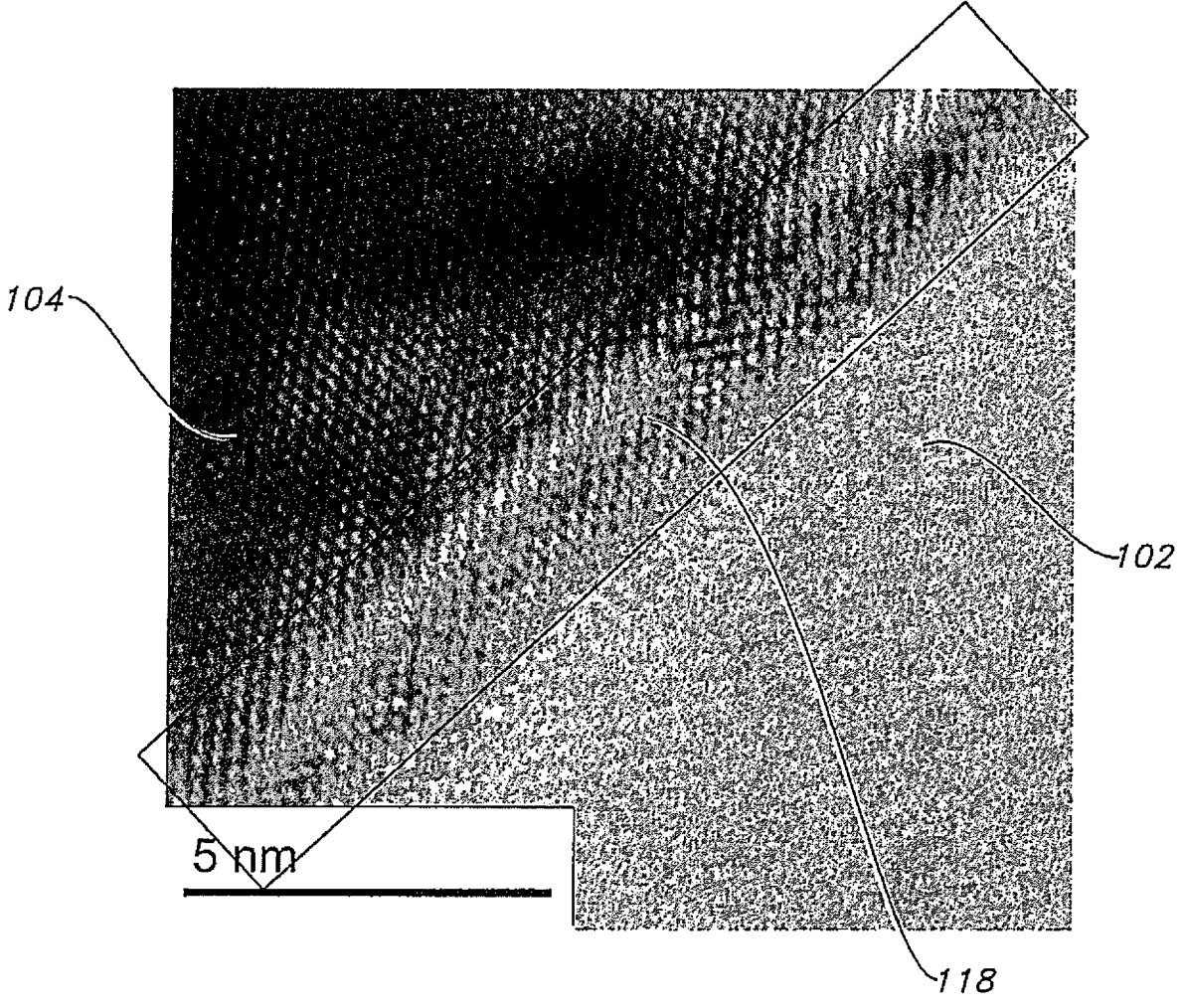
FIG. 28 is a high-resolution TEM image of the Pt—$Al_2O_3$ interface of FIG. 27.

FIG. 28 is a high-resolution TEM (HRTEM) image of the adhered Pt—$Al_2O_3$ interface 118 of FIG. 27. Inspection of the atomic arrangement at interface 118 (within rectangle) shows disorder, dislocation and intermingling of Pt metal 104 and the $Al_2O_3$ ceramic 102 atoms. Such disorder, dislocation and intermingling of two dissimilar materials suggests chemical bonding between the materials.

Figure 29:
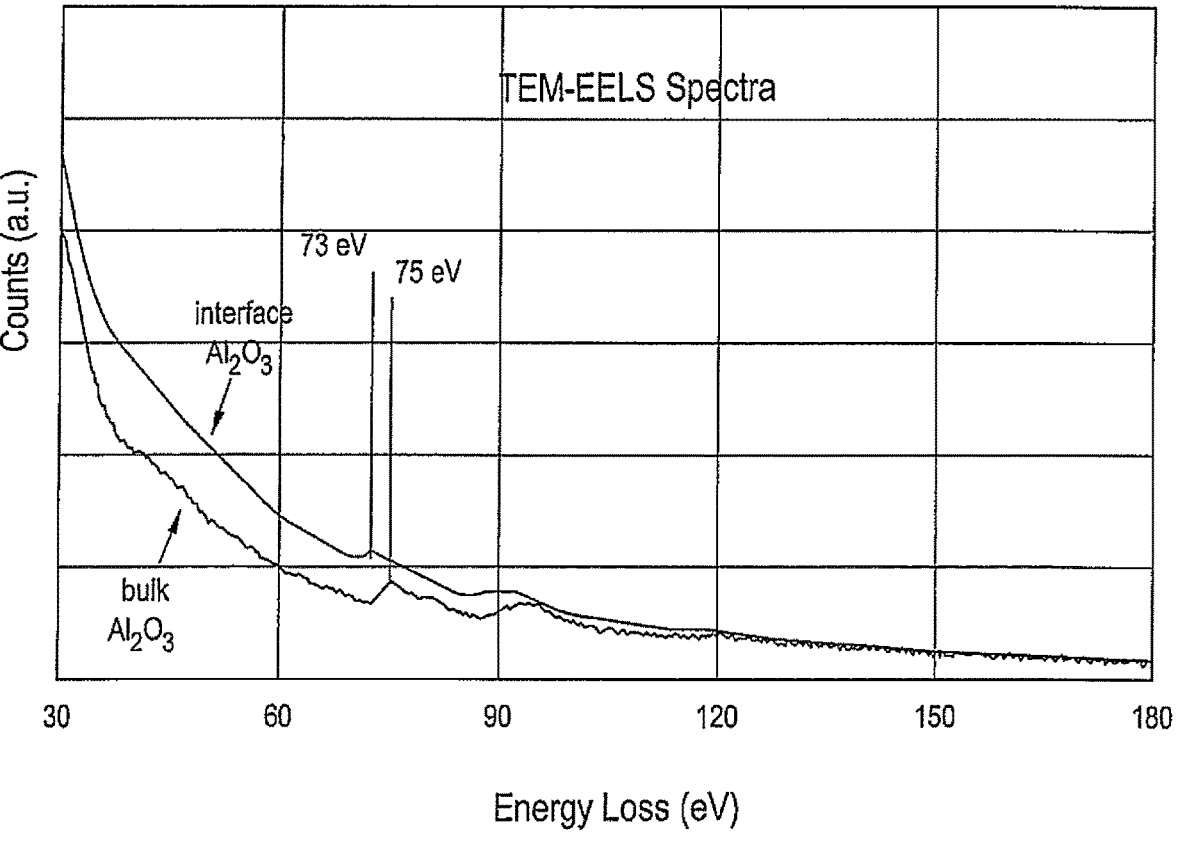
FIG. 29 is an overlay of spectra obtained by transmission electron microscopy-based electron energy-loss spectroscopy (TEM-EELS) conducted at the Pt—$Al_2O_3$ interface of FIG. 28.

FIG. 29 is an overlay of spectra obtained by transmission electron microscopy-based electron energy-loss spectroscopy (TEM EELS) conducted at the Pt—$Al_2O_3$ interface 118 in the area of the rectangle of FIG. 28. TEM-EELS is a technique that measures the change in kinetic energy of electrons after they interact with a sample. TEM-EELS is used to determine the atomic structure and chemical properties of the sample, including the type and quantity of atoms present, the chemical state of the atoms and the collective interactions of the atoms with their neighbors. The TEM-EELS graph of FIG. 28 shows an $Al_2O_3$ spectrum at the adhered Pt—$Al_2O_3$ interface 118 of the CRMC 100 of the present invention and the spectrum of the $Al_2O_3$ powder used to make the composite particle powder 132 of the paste that was co-sintered with the $Al_2O_3$ ceramic body 106. The spectrum of the $Al_2O_3$ at the interface 118 is then compared to the spectrum of the starting $Al_2O_3$ to determine energy loss. Energy loss provides insight into the valence state of the elements of the $Al_2O_3$ at interface 118. The $Al_2O_3$ spectra of FIG. 28 shows an energy difference of 2 eV, indicating a chemical shift. Chemical shift denotes a change in the local chemical environment, which implies a redistribution of valence charge within the $Al_2O_3$ molecule. The $Al_2O_3$ at interface 118 lost about 2 eV of energy, which indicates that the valence state of the aluminum atom of $Al_2O_3$ at interface 118 changed from a valence state of $Al^{3+}$ to a valence state of $Al^{2+}$. Redistribution of valence charge characteristically occurs with atomic bonding. Therefore, the disorder, dislocation and intermingling of the $Al_2O_3$ and Pt atoms at interface 118 of FIG. 28 in context with the 2-eV energy loss by the aluminum atom as determined by the graph of FIG. 29 is compelling evidence toward the formation of Pt—O bonds at the adhered Pt—$Al_2O_3$ interface 118. The implied formation of Pt—O bonds indicate that the Pt and $Al_2O_3$ are not just adhered, but also have direct Pt—$Al_2O_3$ bonding. Such direct Pt—$Al_2O_3$ bonding is microscopically visible in FIGS. 21 and 23.

Figure 30:
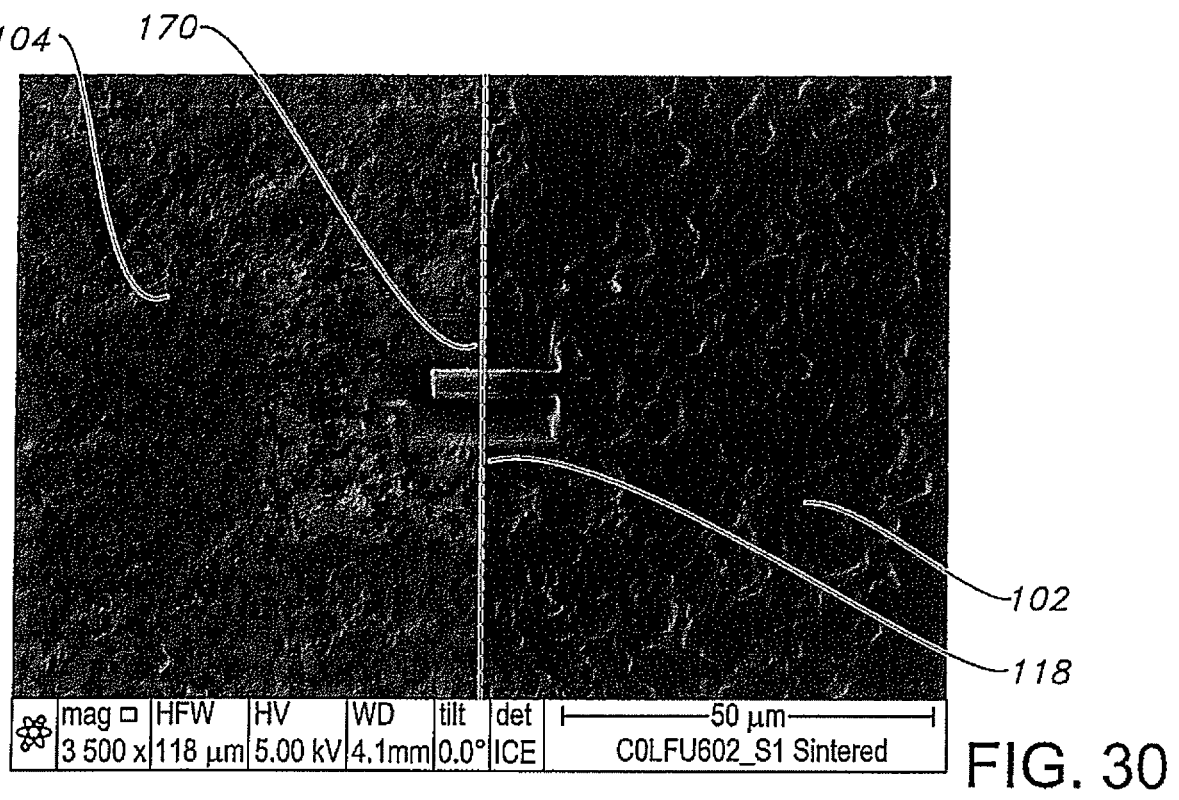
FIG. 30 is an SEM image of a top-down view of a lift out location for a Pt—$Al_2O_3$ interface TEM-ready sample.
Figure 31:
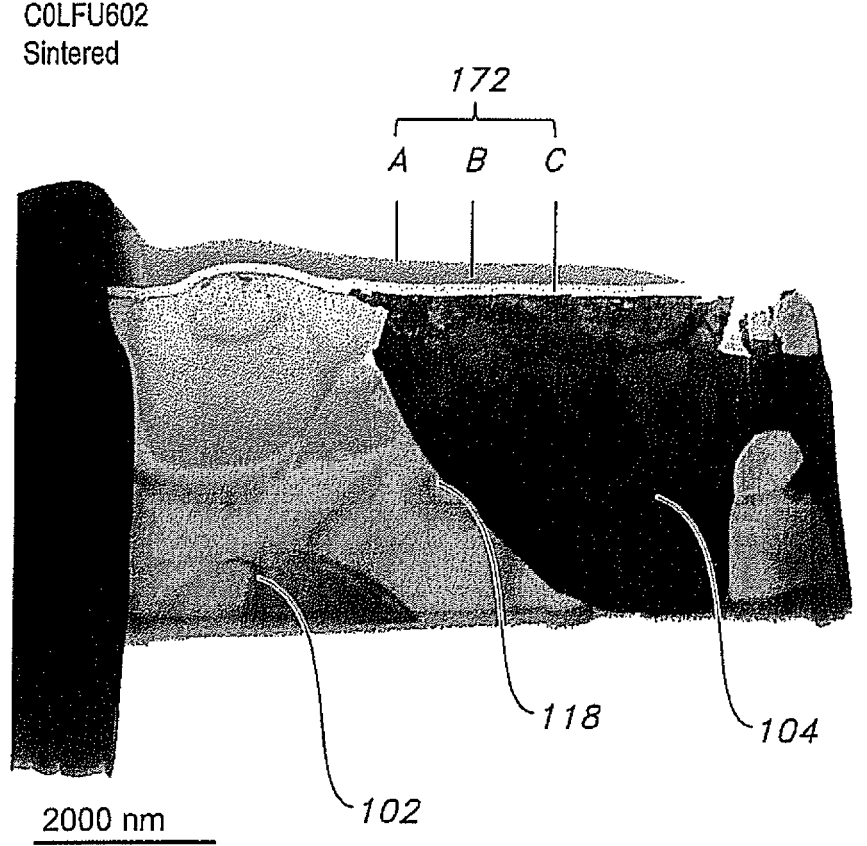
FIG. 31 is a bright field TEM image of the TEM-ready sample extracted from the lift out location of FIG. 30.
Figure 32:
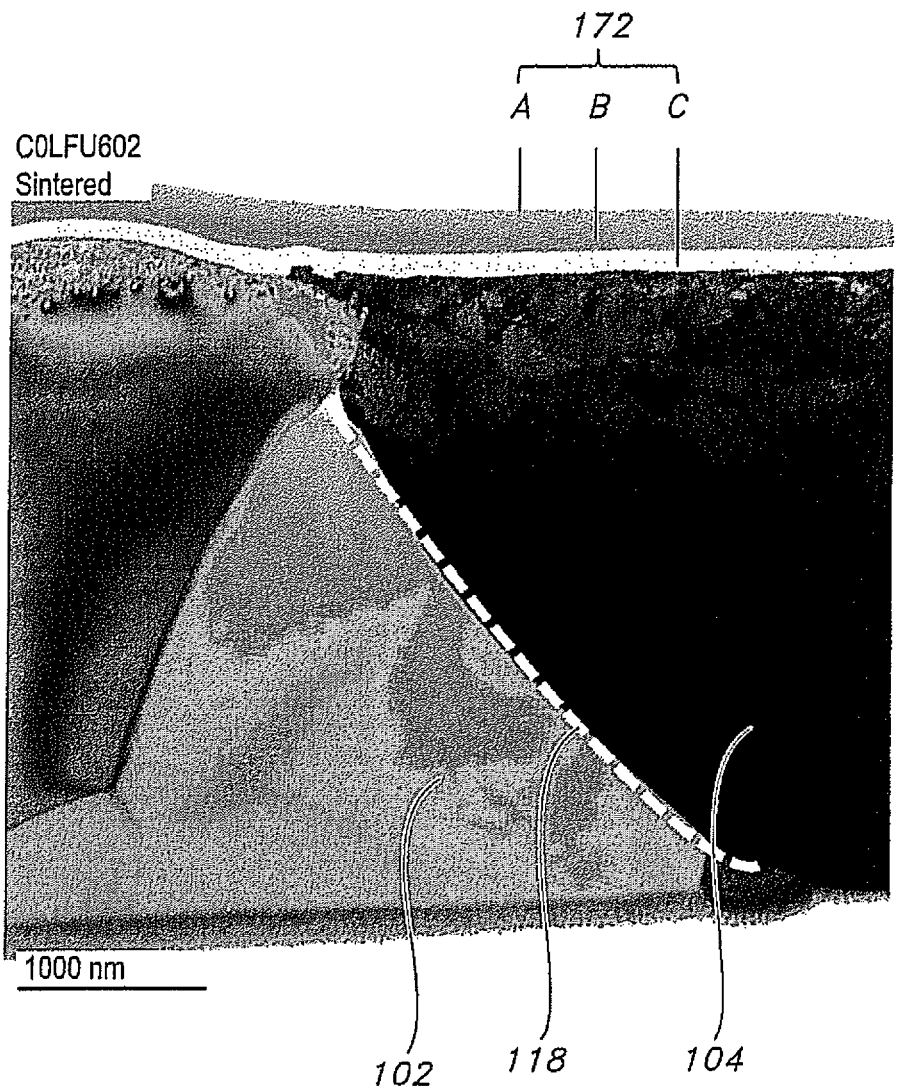
FIG. 32 is a higher magnification of the TEM image of FIG. 31.

FIGS. 30, 31 and 32 are images related to a TEM-ready CRMC 100 test sample for use in conducting selected area electron diffraction (SAED), which also sometimes uses the acronym SAD. TEM SAED patterns are analyzed to evaluate the crystallographic structure of materials. Understanding the crystallographic structure of materials along an interface 118 provides insight to interfacial bonding.

FIG. 30 is an SEM image of a top-down view of a lift out location 170 at the interface 118 of Pt metal 104 and $Al_2O_3$ ceramic 102. The dashed line between the Pt metal 104 and the $Al_2O_3$ ceramic 102 identifies a Pt—$Al_2O_3$ interface 118. The TEM-ready sample was prepared by an in-situ focused ion beam (FIB) lift out technique using an FEI Strata 400 Dual Beam FIB-SEM. The in-situ FIB is slices of an electron transparent lamella from the lift out location 170 at the Pt—$Al_2O_3$ interface 118.

FIG. 31 is a bright field TEM image of the TEM-ready sample extracted from the lift out location 170 of FIG. 30.

The TEM-ready sample has a cap 172 comprising sputtered iridium (Ir) A, protective carbon B, and e-Pt/I—Pt C layers, which were applied prior to FIB final milling. The TEM-ready sample has a lamella thickness of about 100 nm. The TEM-ready sample was imaged using an FEI Tecnai Talos field emission gun-transmission electron microscope (FEG-TEM) operated at 200 kV in the bright-field (BF) and a high-resolution (HR) TEM modes.

FIG. 32 is a higher magnification of the TEM image of FIG. 31. A dashed line identifies the Pt—$Al_2O_3$ interface 118 TEM-ready sample of FIG. 32. TEM SAED was conducted on both sides of the Pt—$Al_2O_3$ interface 118. TEM SAED provides information about a crystallographic structure by reflecting the atomic arrangement of the crystal. A lattice is an ordered set of points. The lattice points represent the positions of the atoms of a crystal. A lattice point row that is parallel to the intersection of two or more parallel planes defines a zone axis. When two different materials have lattice planes that are in parallel and intersect a common direction, the common direction establishes that the two materials have the same zone, and chemical bonding between the two materials is indicated. As such, TEM SAED of the Pt and $Al_2O_3$ of FIG. 32 was conducted in accordance with the physics of Bragg diffraction. Bragg diffraction patterns depend on the orientation of the TEM-ready sample to the TEM electron beam. When the sample is tilted so a lattice plane of atoms satisfies the crystallographic direction of the Bragg condition, then a distinctive diffraction pattern can be obtained having diffraction maxima in arrangements that appear as spots. The spots are called reflections, as they reflect the crystal structure of the sample. The diffraction patterns of different materials can then be analyzed to determine if there are lattice planes in each material that intersect a common direction (in other words, have a common zone axis).

Figure 33:
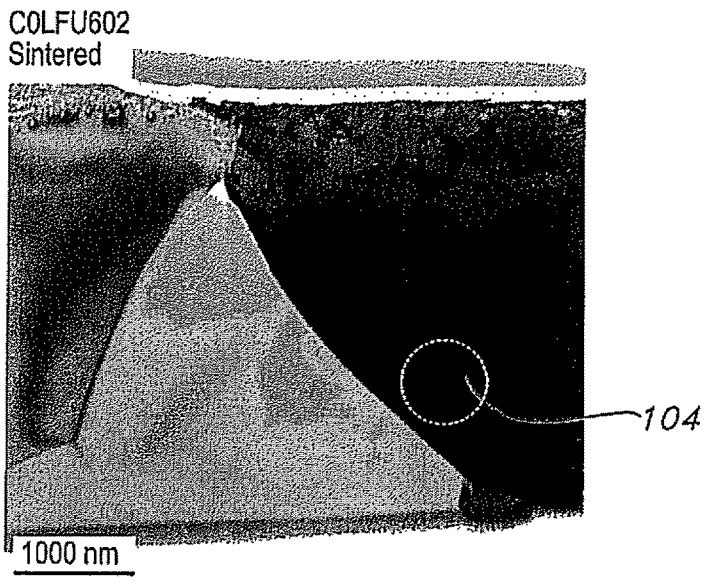
FIG. 33 shows a dashed circle on the Pt side of FIG. 32.

FIG. 33 shows a dashed circle on the Pt metal 104 of FIG. 32, which identifies the relative location where TEM SAED was conducted on the Pt side of interface 118.

Figure 34:
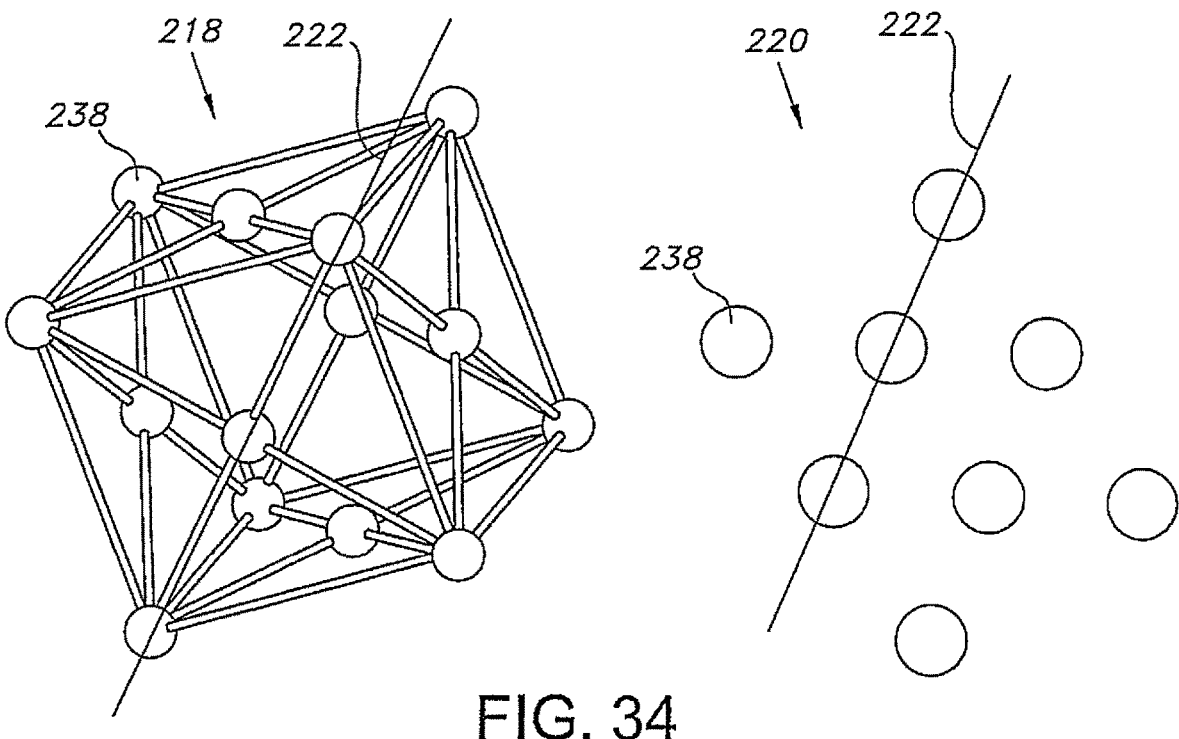
FIG. 34 illustrates 3D ball-and-stick and 2D ball molecular models for Pt.

FIG. 34 illustrates molecular models for Pt metal 104. On the left side is a 3D ball-and-stick model 218, and on the right side is a face view 2D ball model 220. The balls of each model represent Pt atoms 238, and the sticks between the balls of the 3D model 218 represent atom-to-atom bonds. The 3D model 218 of FIG. 34 shows that the unit cell of Pt is a close packed face centered cubic (FCC). The 3D model 218 has six faces, each face having five Pt atoms 238 arranged like the face of a dice marked with five dots. The 2D model 220 shows a face view of two Pt FCC unit cells.

Referring again to FIG. 34, the straight line diagonally through each model represents a Pt zone axis 222. As previously disclosed, the zone axis is a basis line to which lattice plane parallellity is assessed. The Pt zone axis 222 is used to determine orientation of the Pt lattice planes.

Figure 35:
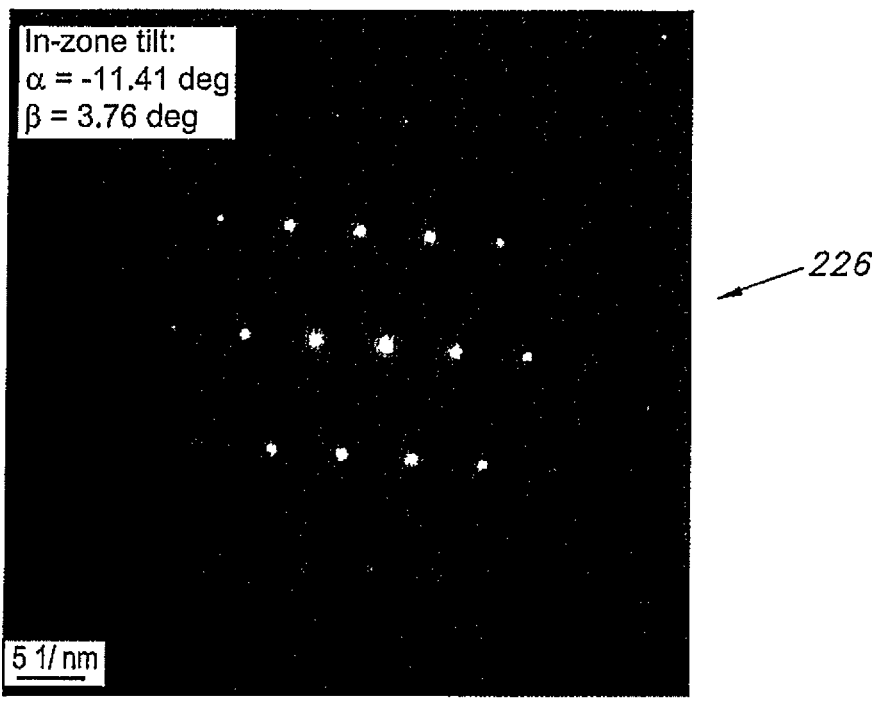
FIG. 35 is a Pt transmission electron microscope selected area electron diffraction (TEM SAED) pattern on the Pt side of the interface of FIG. 33.

FIG. 35 is a TEM SAED Pt diffraction pattern 226 on the Pt side of interface 118 as indicated by the dashed circle of FIG. 33. The TEM-ready sample was rotated to an in-zone tilt having α, β angles of α (−11.41°) and β (3.76°). The in-zone tilt positions the Pt zone axis 222 parallel to the electron beam of the TEM.

Figure 36:
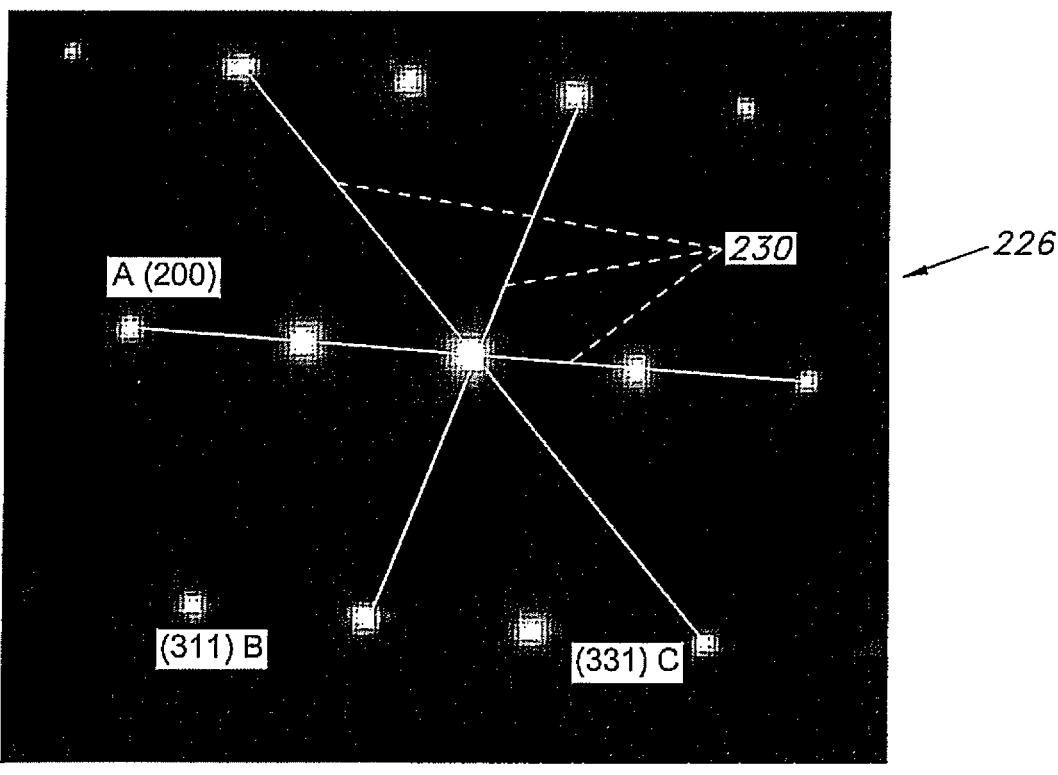
FIG. 36 is an enlarged view of the in-zone Pt TEM SAED pattern of FIG. 35.

FIG. 36 is an enlarged view of the TEM SAED in-zone Pt diffraction pattern 226 of FIG. 35 showing three lines A, B and C, each indicating a lattice plane 230. Line A signifies the (200) Pt lattice plane 230, line B the (311) Pt lattice plane 230, and line C the (331) Pt lattice plane 230.

Figure 37:
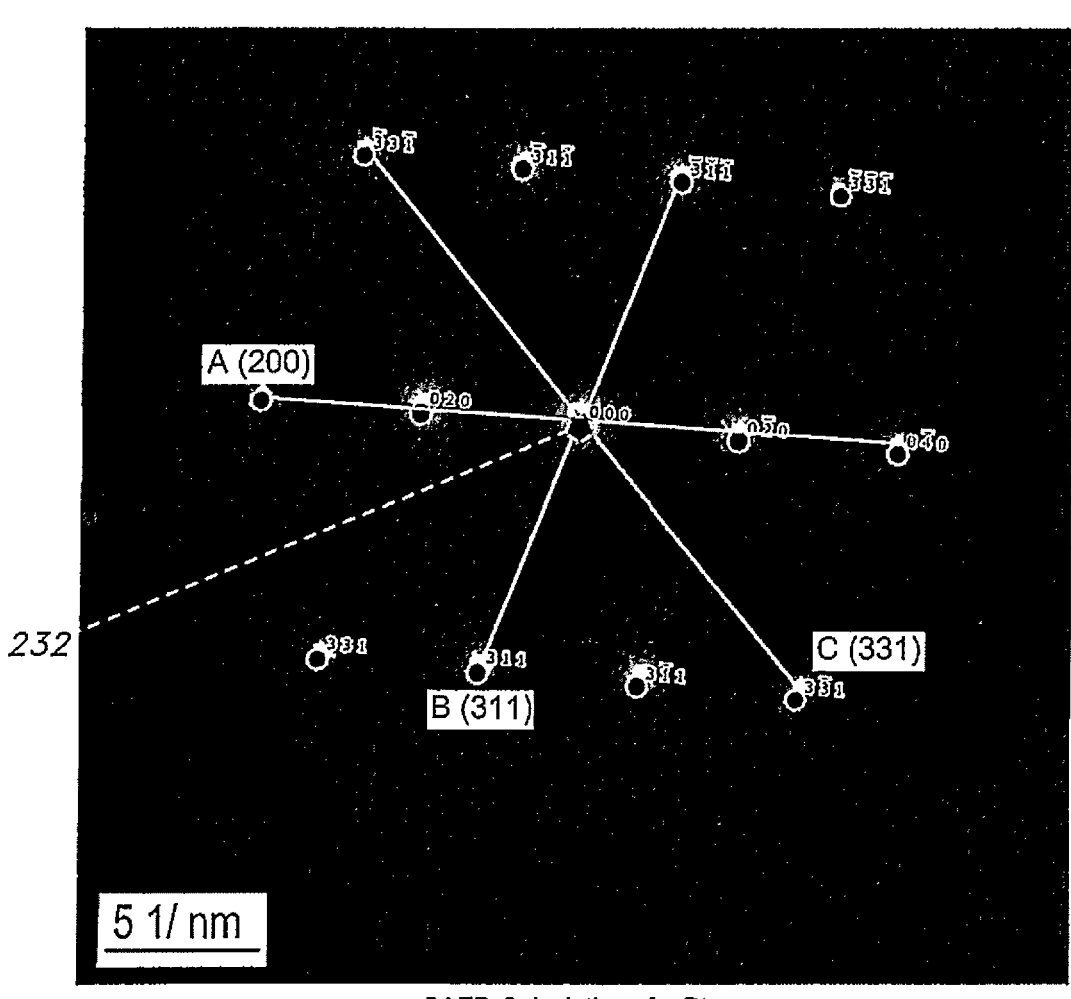
FIG. 37 shows the indices for each spot of the Pt TEM SAED pattern of FIG. 36.

FIG. 37 shows the indices for each spot of the TEM SAED Pt diffraction pattern 226 of FIG. 36. The haloed black spot in the center of the Pt diffraction pattern 226 is the (000) spot. As the electron beam and the zone axis direction are the same, (000) is assigned on the basis that the haloed spot is the closest to the electron beam. All other spot measurements are made relative to the (000) spot. The software used to index the Pt diffraction pattern 226 was EMView. The image was calibrated using the scale marker (5.1/nm). The calculations for indexing are provided at the bottom of FIG. 37.

Figure 38:
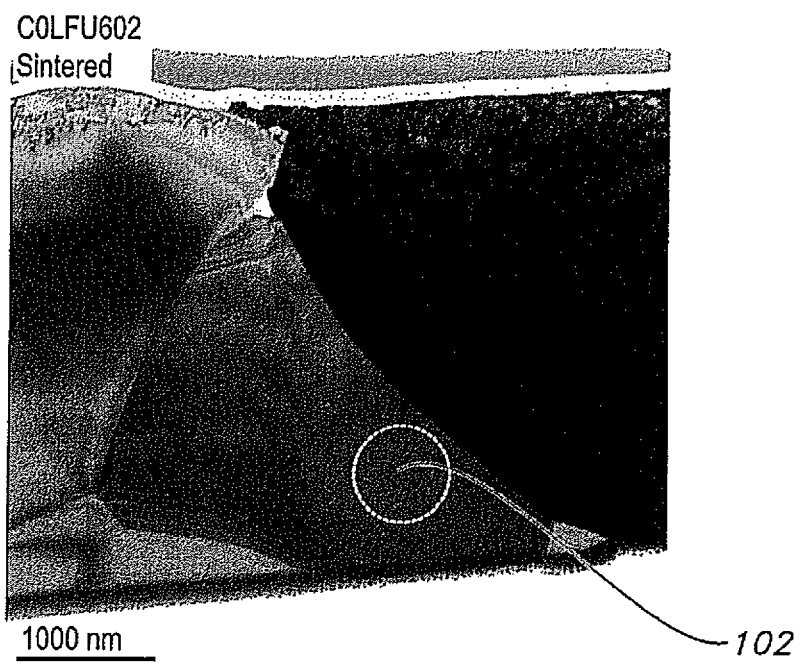
FIG. 38 shows a dashed circle on the $Al_2O_3$ side of FIG. 32.

FIG. 38 shows a dashed circle on the $Al_2O_3$ ceramic 102 of FIG. 32, which identifies the relative location where TEM SAED was conducted on the $Al_2O_3$ side of interface 118.

Figure 39:
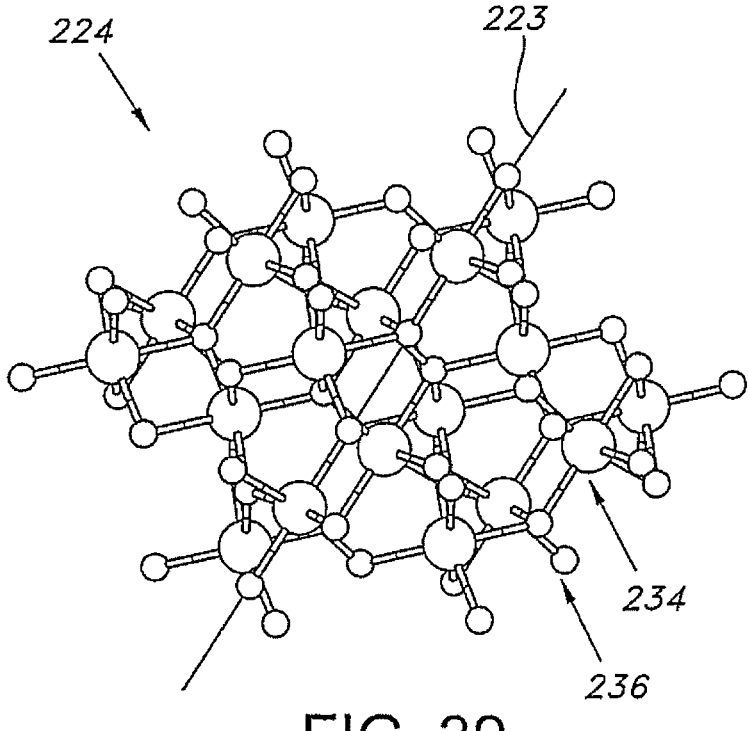
FIG. 39 illustrates 3D ball-and-stick molecular models for $Al_2O_3$.

FIG. 39 illustrates a molecular 3D ball-and-stick model 224 for $Al_2O_3$ ceramic 102. The large balls represent oxygen atoms 234 and the small balls represent aluminum atoms 236. The aluminum atoms 236 are tetrahedrally coordinated to the oxygen atoms 234, displaying trigonal symmetry. The sticks in the model indicate atom-to-atom bonding. The straight line drawn diagonally through the $Al_2O_3$ ball-and-stick model represents the $Al_2O_3$ zone axis 223. As previously disclosed, the zone axis is a basis line to which lattice plane parallellity is assessed. The $Al_2O_3$ zone axis 223 is used to determine orientation of the $Al_2O_3$ lattice planes.

Figure 40:
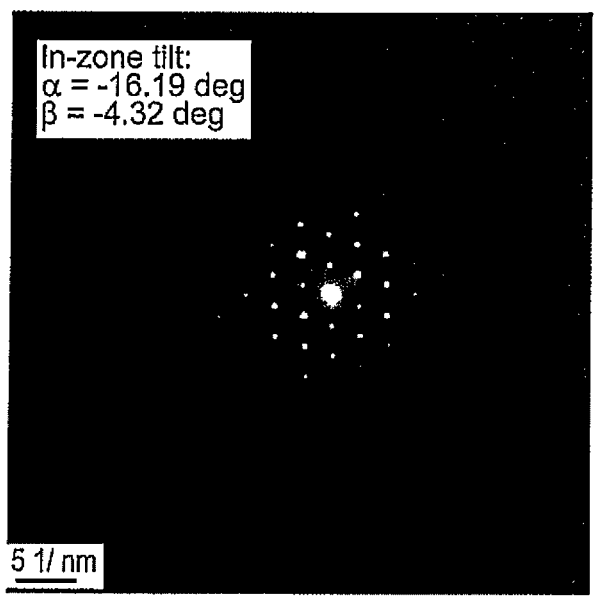
FIG. 40 is an in zone $Al_2O_3$ TEM SAED pattern on the $Al_2O_3$ side of interface of FIG. 33.

FIG. 40 is a TEM SAED diffraction pattern 228 on the $Al_2O_3$ side of interface 118, as indicated by the dashed circle of FIG. 38. The TEM-ready sample was rotated to an in-zone tilt having $\alpha$, $\beta$ angles of $\alpha$ (−16.19°) and $\beta$ (−4.32°). The in-zone tilt positions the $Al_2O_3$ zone axis 223 parallel to the electron beam of the TEM.

Figure 41:
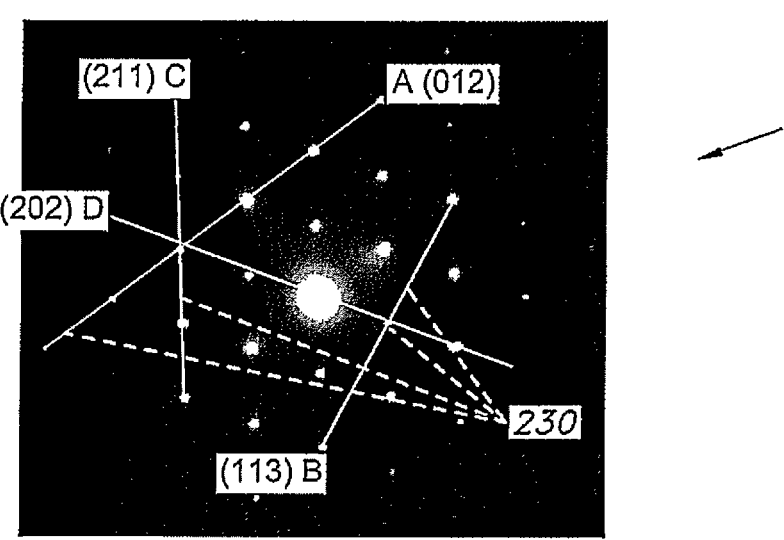
FIG. 41 is an enlarged view of the $Al_2O_3$ TEM SAED pattern of FIG. 40.

FIG. 41 is an enlarged view of the TEM SAED in zone $Al_2O_3$ diffraction pattern 228 of FIG. 40 showing four lines A, B, C and D, each indicating a lattice plane 230. Line A signifies the (012) $Al_2O_3$ lattice plane 230, line B the (113) $Al_2O_3$ lattice plane 230, line C the (211) $Al_2O_3$ lattice plane 230, and line D the (202) $Al_2O_3$ lattice plane 230.

Figure 42:
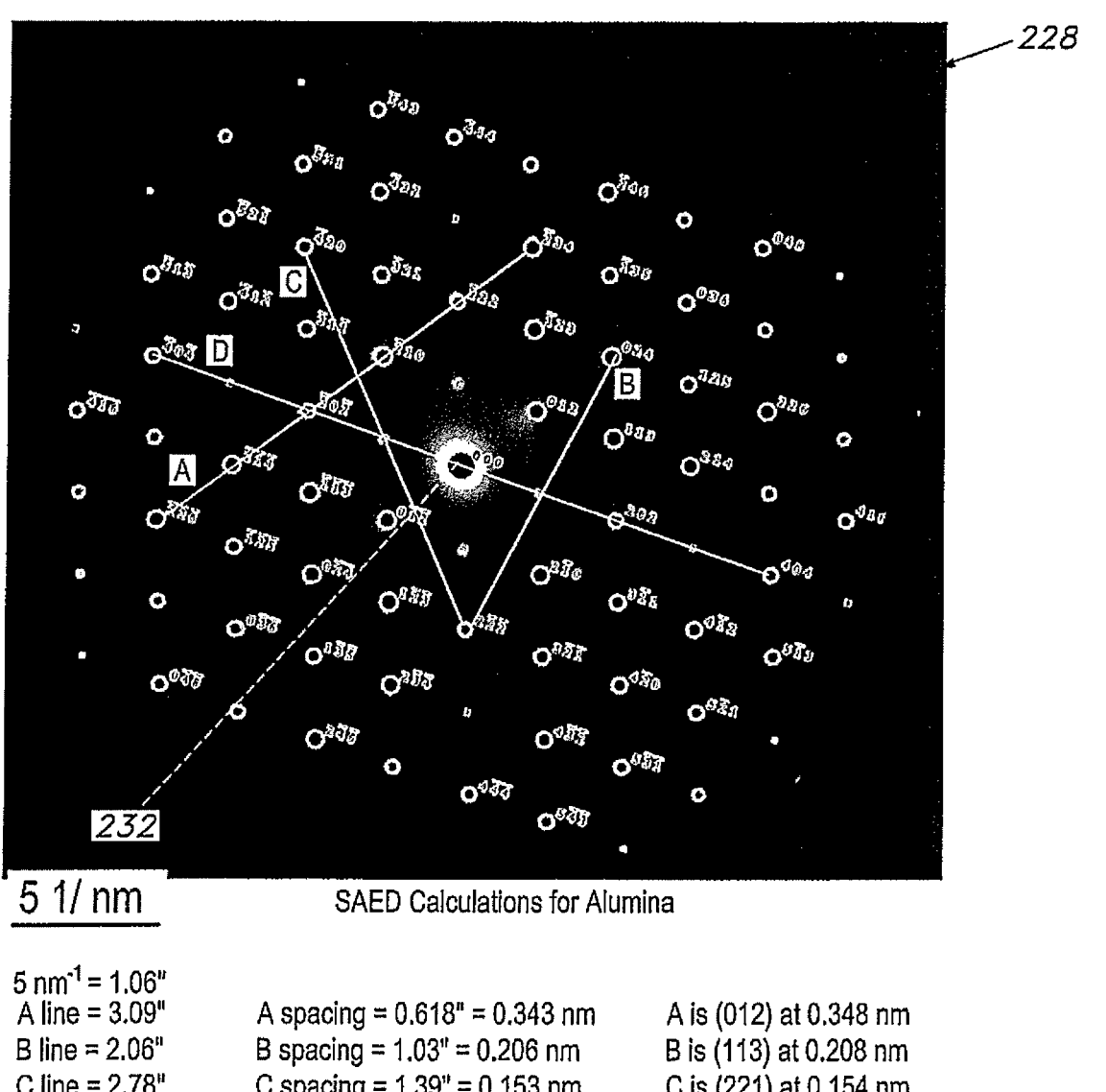
FIG. 42 shows the indices for each spot of the TEM SAED $Al_2O_3$ diffraction pattern of FIG. 41.

FIG. 42 shows the indices for each spot of the TEM SAED in zone $Al_2O_3$ diffraction pattern 228 of FIG. 41. The haloed black spot in the center of the $Al_2O_3$ diffraction pattern 228 is the (000) spot. All other spot measurements are made relative to the (000) spot, which is the closest spot to the electron beam. The software used to index the $Al_2O_3$ diffraction pattern 228 was EMView. The image was calibrated using the scale marker (5.1/nm). The calculations for indexing are provided at the bottom of FIG. 42.

Figure 43:
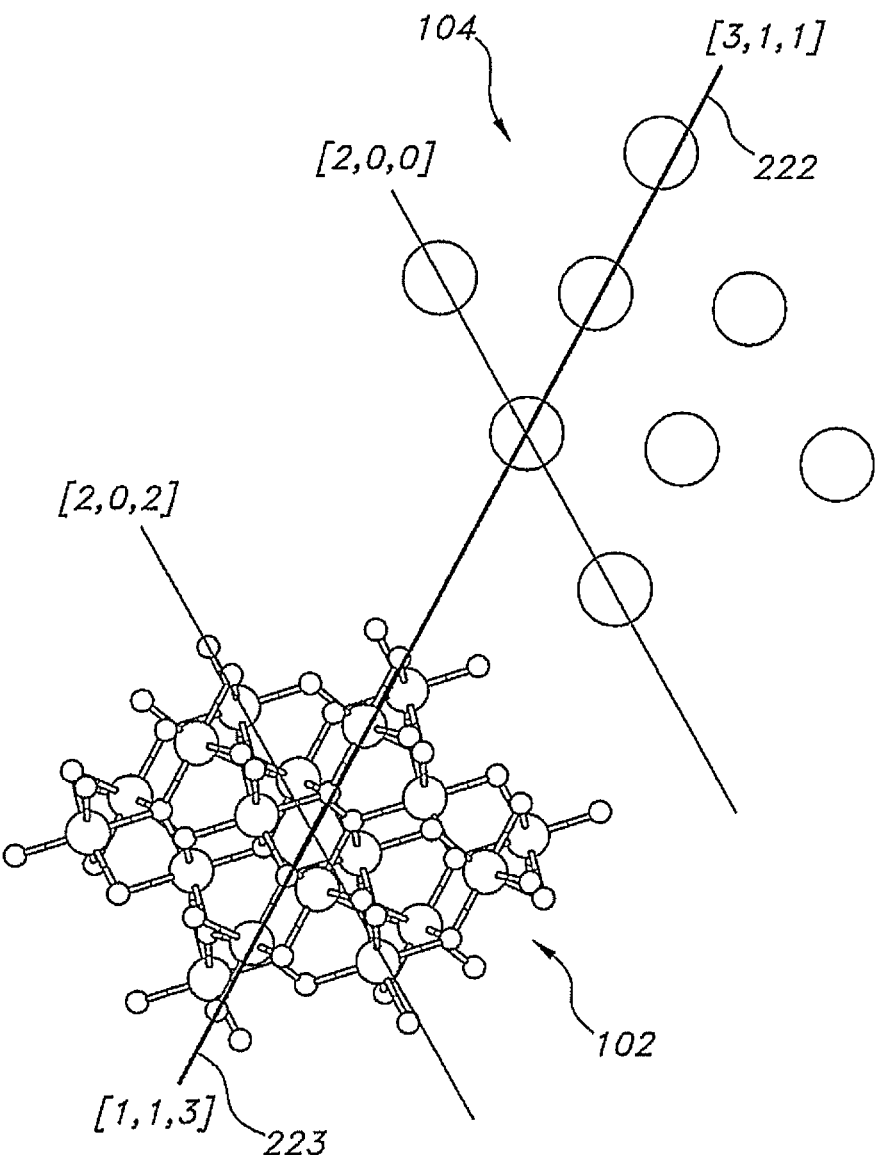
FIG. 43 combines the $Al_2O_3$ ball-and-stick model of FIG. 39 and the 2D face view Pt ball model of FIG. 34 with their respective diffraction pattern information.

FIG. 43 combines the $Al_2O_3$ ball-and-stick model 224 of FIG. 39 and the 2D face view Pt ball model 220 of FIG. 34 with their respective diffraction pattern information. The Pt diffraction pattern 226 of FIG. 36 identifies a (200) plane. The $Al_2O_3$ diffraction pattern 228 of FIG. 41 identifies a (202) plane. FIG. 43 shows that the (200) plane of the Pt has a row of atoms in the [2,0,0] direction and that (202) plane of the $Al_2O_3$ has a row of atoms in the [2,0,2] direction. FIG. 43 also shows that when the (200) plane of the Pt is in parallel with the (202) plane of the $Al_2O_3$, a row of atoms in the Pt (311) plane and the $Al_2O_3$ (113) plane share a common direction. The (311) and (113) planes are two planes of one (hkl) family, so are equivalent planes. The combined common direction is illustrated by joining the Pt zone axis 222 and the $Al_2O_3$ zone axis 223. The Pt zone axis 222 has a row of atoms in the [3,1,1] direction and the $Al_2O_3$ zone axis has a row of atoms in the [1,1,3] direction. It follows then that, since the (311) and (113) planes are equivalent because they belong to the same (hkl), then the [3,1,1] and [1,1,3] directions are also equivalent, which is why the direction of Pt and $Al_2O_3$ zone axes merge so nicely. Accordingly, as the Pt and $Al_2O_3$ have lattice planes that are in parallel and intersect a common direction, the common direction indicates that the Pt and $Al_2O_3$ are chemically bonded.

The TEM SAED Pt and $Al_2O_3$ diffraction pattern provides a local relationship between the in-zone Pt and $Al_2O_3$. Accordingly, the specific planes and directions identified are not a universal representation along the entire Pt—$Al_2O_3$ interface. Polycrystalline materials, including the CPMC 100 of the present invention, comprise a plurality of Pt and $Al_2O_3$ grains that can be differently oriented one to the other. While this particular TEM SAED analysis reflects specific in zone Pt and $Al_2O_3$ planes intersecting a specific common zone axis, it is understood that TEM SAED conducted in other select Pt and $Al_2O_3$ interface areas may find different parallel planes sets and common directions than those of FIG. 43. Regardless, TEM SAED Pt and $Al_2O_3$ diffraction pattern analysis further supports the chemical bonding of Pt and $Al_2O_3$ at interface 118.

Figure 44:
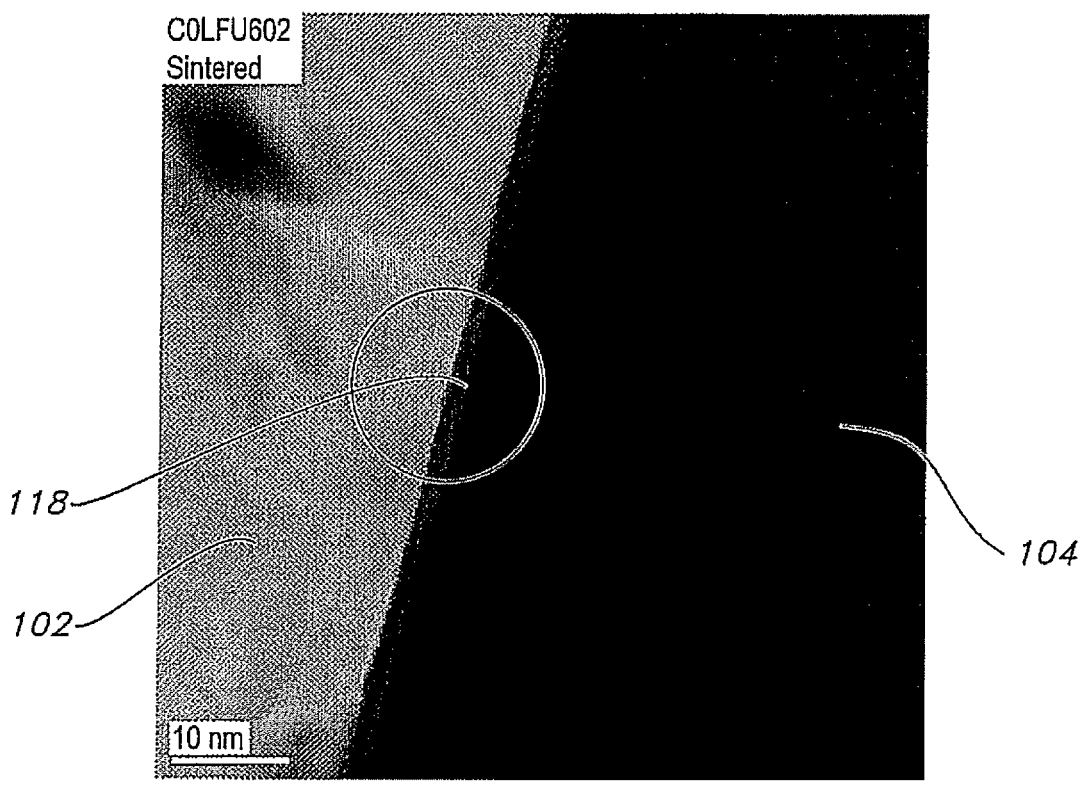
FIG. 44 illustrates a TEM image of an interface between the Pt and $Al_2O_3$.

FIG. 44 illustrates a TEM image of an interface 118 between the Pt metal 104 and the $Al_2O_3$ ceramic 102 of the CRMC 100 of the present invention. As indicated by the 10 nm image marker of FIG. 44, the thickness of the Pt—$Al_2O_3$ interface 118 is about 1.5 nm. Higher sintering temperatures and/or longer sintering times will increase the thickness of an interface 118 between a metal 104 and a ceramic 102. Higher sintering temperatures may be held for a time period conducive for achieving a desired target thickness. Other non-limiting factors that influence the thickness of an interface 118 comprising a metal 104 and a ceramic 102 include: powder composite particle size and/or morphology; composite particle powder composition and/or formulation; and/or composite particle loading. The thickness of a metal-ceramic interface 118 may therefore range between >0 nm to ≤200 nm. Depending on the application needs, the thickness of the metal-ceramic interface 118 may reasonably be greater than 200 nm up to 500 nm.

Figure 45:
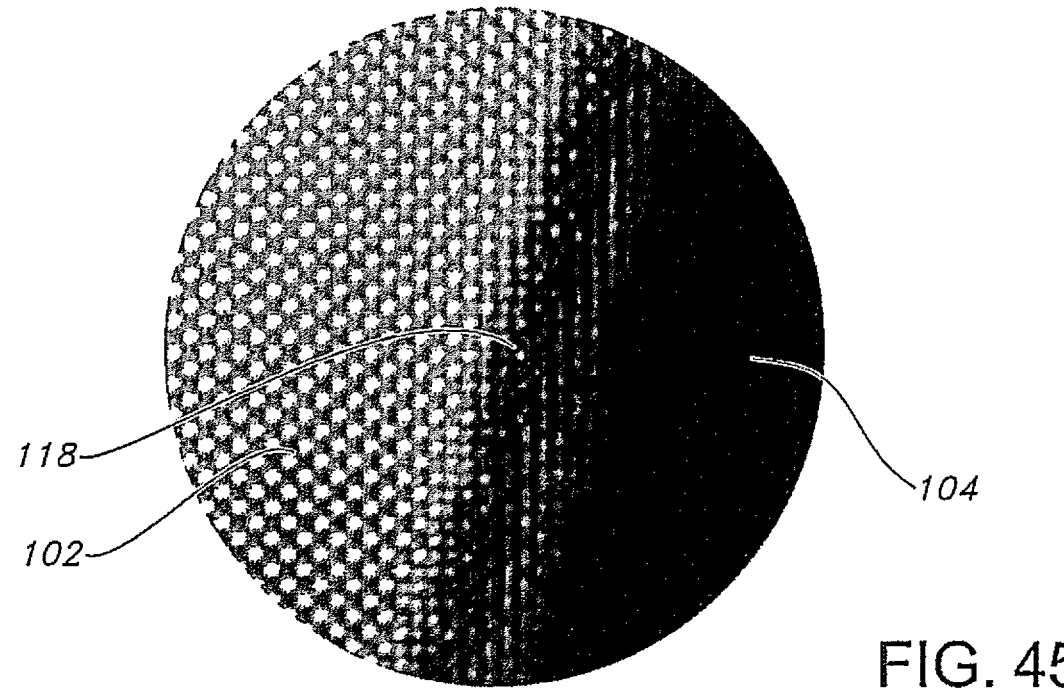
FIG. 45 is an enlarged view of the Pt—$Al_2O_3$ interface of FIG. 44.

FIG. 45 is an enlarged view of the Pt—$Al_2O_3$ interface 118 in the area indicated by the circle of FIG. 44. The atomic arrangement at the Pt—$Al_2O_3$ interface 118 of FIG. 45 shows disorder, dislocation and intermingling of the Pt metal 104 and $Al_2O_3$ ceramic 102, similar to the adhered Pt—$Al_2O_3$ interface 118 of FIG. 28.

Figure 46:
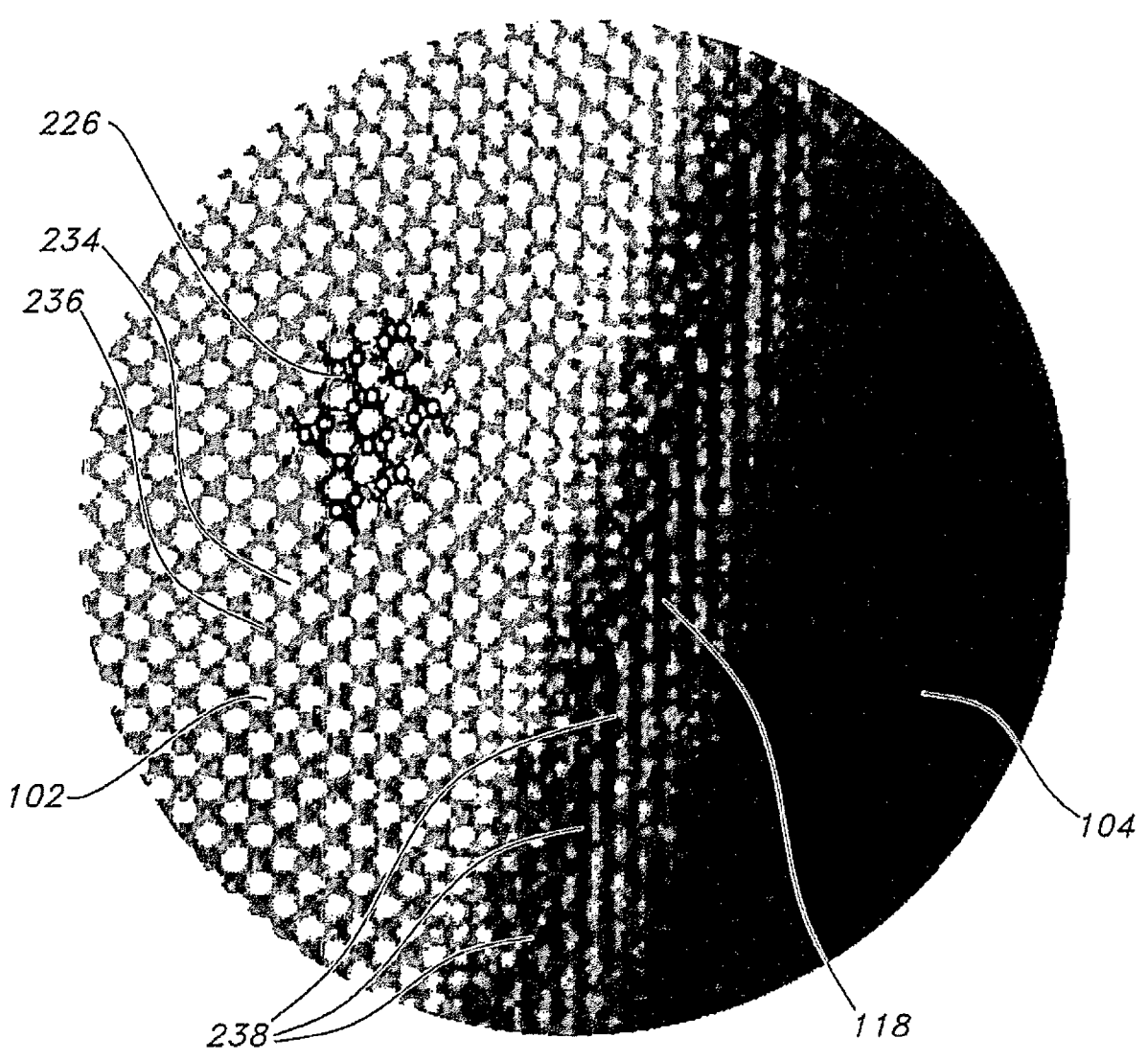
FIG. 46 is an enlarged view of FIG. 45 with the $Al_2O_3$ ball-and-stick model of FIG. 39 superimposed atop the $Al_2O_3$.

FIG. 46 illustrates the enlarged view of the TEM image of FIG. 45 with the $Al_2O_3$ ball-and-stick model superimposed atop the $Al_2O_3$ ceramic 102 near the Pt—$Al_2O_3$ interface 118 of the TEM-ready sample. The atoms of the $Al_2O_3$ ceramic 102 itself are clearly visible in this TEM image. The large light spherical bodies are the oxygen atoms 234, and the small dark spherical bodies are the aluminum atoms 236. The large balls of the superimposed $Al_2O_3$ ball-and-stick model precisely overlay the oxygen atoms 234 of the $Al_2O_3$ ceramic 102 and the small balls of the superimposed $Al_2O_3$ ball-and-stick model precisely overlay the aluminum atoms 236 of the $Al_2O_3$ ceramic 102. Such precise alignment of the ball-and-stick model demonstrates atomic fit to atoms of the crystalline structure of $Al_2O_3$. Examination of the full arrangement of the $Al_2O_3$ oxygen atoms 234 and the aluminum atoms 236 of FIG. 46 reveals that, away from interface 118, the oxygen and aluminum atom arrangement match repeatedly to the modelled arrangement of the $Al_2O_3$ ball-and-stick aluminum and oxygen atoms. However, the closer the $Al_2O_3$ oxygen and aluminum atoms are to the Pt—$Al_2O_3$ interface 118, the more disordered and dislocated the oxygen and aluminum atomic arrangement becomes. More importantly, within the thickness of the Pt—$Al_2O_3$ interface 118, oxygen and aluminum atom disorder and dislocation is fully introduced all along interface 118 due to an intermingling of Pt atoms 238 therethrough. The Pt atoms 238 are the larger dark spherical bodies and the aluminum atoms 236 are the smaller dark spherical bodies. Such disorder and dislocation of both the oxygen atoms 234 and the aluminum atoms 236 in conjunction with the intermingling of Pt atoms 238 along the entire interface 118 convincingly further support the formation of Pt—O bonds at the Pt—$Al_2O_3$ interface 118. To those skilled in the art, it is understood that any two chemically bonded materials always exhibit some degree of interfacial disorder and dislocation in either one or both of the bonded materials. As shown by FIG. 46, atomic disorder and dislocation can be visibly identified near and within the Pt—$Al_2O_3$ interface 118.

FIGS. 47 through 69 illustrate various medical device component embodiments incorporating a ceramic body 106 comprising one or more CPMC 100 electrical conductors.

Hermeticity is a critical requirement for medical implantable devices. Implantable components for medical devices and systems may comprise a helium leak rate no greater than $1 \times 10^{-6}$ std cc He/s. For example, feedthroughs for implantable medical devices may comprise a helium leak rate no greater than $1 \times 10^{-7}$ std cc He/s. Implantable devices and systems may comprise helium leak rates that vary as the internal free volume of the implantable device or system varies. For example, a coin-sized implantable device may comprise a helium leak rate no greater than $1 \times 10^{-9}$ std cc He/s. An implantable sensor, micro-electromechanical system (MEMS) or bion may comprise a helium leak rate of $1 \times 10^{-11}$ to $1 \times 10^{-13}$ std cc He/s. In an embodiment, a ceramic body 106 having one or more hermetically sealed CRMC 100 electrical conductors comprises a leak rate ranging between $1 \times 10^{-6}$ std cc He/s to $1 \times 10^{-13}$ std cc He/s.

Active implantable medical devices (AIMD) can be used in both low voltage and high voltage applications. For example, cardiac pacemakers are generally low voltage devices, while implantable cardiac defibrillators are generally high voltage devices. Likewise, some AIMDs deliver low current stimulation therapy, while other AIMDs deliver high current shocking pulses. As such, the electrical resistance of a medical device electrical conductor becomes important. In an embodiment, a ceramic body 106 having one or more hermetically sealed CRMC 100 electrical conductors comprises an electrical resistance ranging between $\geq 0$ mΩ to $\leq 1,000$Ω. In an embodiment, a ceramic body 106 having one or more hermetically sealed CRMC 100 electrical conductors comprises an electrical resistance of no more than $1,000$Ω. In an embodiment, a ceramic body 106 having one or more hermetically sealed CRMC 100 electrical conductors comprises an electrical resistance of no more than $500$Ω. In an embodiment, a ceramic body 106 having one or more hermetically sealed CRMC 100 electrical conductors comprises an electrical resistance of no more than $100$Ω. In an embodiment, a ceramic body 106 having one or more hermetically sealed CRMC 100 electrical conductors comprises an electrical resistance of no more than $10$Ω. In an embodiment, a ceramic body 106 having one or more hermetically sealed CRMC 100 electrical conductors comprises an electrical resistance of no more than $1$Ω. In an embodiment, a ceramic body 106 having one or more hermetically sealed CRMC 100 electrical conductors comprises an electrical resistance of no more than 500 mΩ. In an embodiment, a ceramic body 106 having one or more hermetically sealed CRMC 100 electrical conductors comprises an electrical resistance of no more than 50 mΩ. In an embodiment, a ceramic body 106 having one or more hermetically sealed CRMC 100 electrical conductors comprises an electrical resistance of no more than 10 mΩ. In an embodiment, a ceramic body 106 having one or more hermetically sealed CRMC 100 electrical conductors comprises an electrical resistance of no more than 1 mΩ.

Coefficient of thermal expansion (CTE) mismatch can be a serious concern for AIMDs, as hermetic seals can be compromised if the CTE mismatch between two mating materials is too large. It is understood that the CTE of a material defines how the size of an object changes as temperature changes. In general, during heating, a material having higher CTE produces compressive stress on a material having lower CTE. Then, during cooling, the material having higher CTE produces tensile stress on the material having lower CTE. As such, since large CTE mismatch induces tensile stresses in one material and compressive stresses in the other material; hence, CTE is an important factor for medical implantable device components. Using Pt and $Al_2O_3$ as an example, TABLE 4 below lists publicly disclosed CTEs of commercially available Pt metal and various $Al_2O_3$ formulations. The CTEs of these commercial materials were determined by a dilatometer test method performed at 1,000° C. in accordance with ASTM Standard E228, entitled: "Standard Test Method for Linear Thermal Expansion of Solid Materials With a Push-Rod Dilatometer". Inspection of the $Al_2O_3$ CTE data of TABLE 4 establishes that the CTE of $Al_2O_3$ depends on the purity level of the $Al_2O_3$. Using the CTE of commercially available solid Pt metal as a reference basis, the CTE mismatch between the solid Pt metal and the $Al_2O_3$ materials can be determined. The CTE values of TABLE 4 reveal that, at 1,000° C., a higher $Al_2O_3$ content results in a closer CTE match of the $Al_2O_3$ to a solid Pt metal. It is understood that the CTE of a solid material, such as the solid Pt reference basis of TABLE 4, refers to a rate at which a material expands with an increase in temperature. More specifically, CTE is generally determined without material phase change, meaning that the material is expected to still be in its solid form. Solid metals typically have higher CTEs than ceramics.

TABLE 4

| Material | CTE $(10^{-6\ per}$ ° C.) | CTE $(10^{-6\ per}$ ° F.) | Pt CTE mismatch $(10^{-6\ per}$ ° C.) | Pt CTE mismatch $(10^{-6\ per}$ ° F.) |
|---|---|---|---|---|
| Pt | 8.8 | 4.9 | | |
| 92% $Al_2O_3$ | 7.1 | 3.9 | 1.7 | 1.0 |
| 94% $Al_2O_3$ | 8.1 | 4.5 | 0.7 | 0.4 |
| 96% $Al_2O_3$ | 8.2 | 4.6 | 0.6 | 0.3 |
| 99.5% $Al_2O_3$ | 8.4 | 4.7 | 0.4 | 0.2 |

TABLE 5 below lists the CTE of the CRMC 100 of FIG. 21 and the Pt and $Al_2O_3$ powders used to form the Pt/$Al_2O_3$ composite particles by the partial sinter process. TABLE 5 also contains the CTEs of the commercially available $Al_2O_3$ formulations of TABLE 5. The CTE of the CRMC 100 of FIG. 21 is presented in the Row 2 of TABLE 5 and is the comparison reference basis. The CTE of the Pt and $Al_2O_3$ powders are shown in Rows 3 and 4. The CTEs of commercially available $Al_2O_3$ are shown in Rows 5 through 9. CTEs of the CRMC 100, the Pt and the $Al_2O_3$ source materials were obtained using optical dilatometry. Dilatometric analysis was conducted on green paste test samples at 1,550° C. The data of TABLE 5 demonstrates that a CRMC CTE match of +0.2 per ° C. (+1 per ° F.) can be achieved starting with Pt and $Al_2O_3$ powders. The data of TABLE 5 also demonstrates that a CTE match between the CRMC 100 and the commercially available $Al_2O_3$ ranges between 0.6 per ° C. (0.4 per ° F.) to −0.7 per ° C. (−0.4 per ° F.). Accordingly, since the CTE match of the CRMC 100 and the $Al_2O_3$ transitions from a positive to a negative, the data demonstrates that the CTE of the CRMC 100 of the present inventions can be engineered to match the material of the ceramic body.

TABLE 5

| Row | Reference Basis | CTE $(10^{-6\,per}$ ° C.) | CTE $(10^{-6\,per}$ ° F.) | | |
|---|---|---|---|---|---|
| 2 | CRMC | 7.7 | 4.3 | | |

| Row | Source Material | CTE $(10^{-6\,per}$ ° C.) | CTE $(10^{-6\,per}$ ° F.) | CRMC CTE match $(10^{-6\,per}$ ° C.) | CRMC CTE match $(10^{-6\,per}$ ° F.) |
|---|---|---|---|---|---|
| 3 | Pt | 7.9 | 4.4 | −0.2 | −0.1 |
| 4 | $Al_2O_3$ | 7.5 | 4.2 | 0.2 | 0.1 |

| Row | Material | CTE $(10^{-6\,per}$ ° C.) | CTE $(10^{-6\,per}$ ° F.) | CRMC CTE mismatch $(10^{-6\,per}$ ° C.) | CRMC CTE mismatch $(10^{-6\,per}$ ° F.) |
|---|---|---|---|---|---|
| 5 | CRMC | 7.7 | 4.3 | | |
| 6 | 92% $Al_2O_3$ | 7.1 | 3.9 | 0.6 | 0.4 |
| 7 | 94% $Al_2O_3$ | 8.1 | 4.5 | −0.4 | −0.2 |
| 8 | 96% $Al_2O_3$ | 8.2 | 4.6 | −0.5 | −0.3 |
| 9 | 99.5% $Al_2O_3$ | 8.4 | 4.7 | −0.7 | −0.4 |

In an embodiment the ceramic body 106 is alumina ($Al_2O_3$), wherein the $Al_2O_3$ comprises a purity range of 92% to 99.9% and the CRMC comprises a CTE matched to the CTE of the $Al_2O_3$. In an embodiment, the CTE match of the ceramic body 106 and the CRMC 100 electrical conductor ranges between 0 per ° C. to ±10 per ° C. (0 per ° F. to ±5.61 per ° F.). In an embodiment, the CTE match of the ceramic body 106 and the CMC 100 electrical conductor ranges between 0 per ° C. to ±5 per ° C. (0 per ° F. to ±2.8 per ° F.). In an embodiment, the CTE match of the ceramic body 106 and the CRMC 100 electrical conductor ranges between 0 per ° C. to ±2.5 per ° C. (0 per ° F. to ±1.4 per ° F.).

While the CRMC-ceramic CTE match of the CRMC of TABLE 5 comprises a Pt/$Al_2O_3$ composition composite, other metals or metal alloys and ceramics or glass-ceramics may be used to form the CRMC 100 of the present invention. Suitable metals in addition to or in combination with platinum (Pt), include, but are not limited to, gold (Au), palladium (Pd), silver (Ag), iridium (Ir), rhenium (Re), ruthenium (Rh), titanium (Ti), tantalum (Ta), tungsten (W), niobium (Nb), zirconium (Zr), vanadium (V), and alloys or combinations thereof. Steels and stainless steels may also be used, such as ferritic steels, austenitic steels, martensitic steels and duplex (mixture of ferrite and austenite), each of which are dictated by the chemical composition and thermal and mechanical treatments. For medical applications, ISO 7153-1/1991, the content of which is fully incorporated herein by this reference, specifies stainless steel categories are also suitable for making the CRMC of the present application.

Non-limiting examples of suitable alloys include: cobalt chromium molybdenum alloy, cobalt chromium nickel iron molybdenum manganese alloy, cobalt chromium tungsten nickel iron manganese alloy, cobalt nickel chromium iron molybdenum titanium alloy, cobalt nickel chromium iron molybdenum tungsten titanium alloy, cobalt nickel chromium molybdenum alloy, copper aluminum nickel alloy, copper zinc alloy, copper zinc aluminum nickel alloy, copper zinc silver alloy, gold platinum palladium silver indium alloy, iron chromium alloy, iron chromium nickel alloy, iron chromium nickel aluminum alloy, iron chromium nickel copper alloy, iron chromium nickel copper molybdenum niobium alloy, iron chromium nickel copper niobium alloy, iron chromium nickel copper titanium niobium alloy, iron chromium nickel manganese molybdenum alloy, iron chromium nickel molybdenum alloy, iron chromium nickel molybdenum aluminum alloy, iron chromium nickel titanium molybdenum alloy, iron manganese chromium molybdenum nitrogen alloy, nickel platinum alloy, nitinol, nickel titanium alloy, nickel titanium aluminum alloy, niobium-titanium alloy, platinum iridium alloy, platinum palladium gold alloy, titanium aluminum vanadium alloy, titanium based aluminum iron alloy, titanium based aluminum molybdenum zirconium alloy, titanium based molybdenum niobium alloy, titanium based molybdenum zirconium iron alloy, titanium based niobium zirconium alloy, titanium based niobium zirconium tantalum alloy, titanium molybdenum alloy, titanium niobium alloy, titanium platinum alloy, titanium-based molybdenum zirconium tin alloy. Suitable ceramics include, but are not limited to, alumina ($Al_2O_3$), silica ($SiO_2$), zirconia ($ZrO_2$), titania ($TiO_2$), fused silica, silicon nitride, aluminum nitride, magnesium oxide, barium oxide, barium titanate, sodium-potassium-niobate, calcium oxide, cerium oxide, apatite-wollastonite (A-W) glass ceramic, boron nitride, alumina silicate, and combinations thereof.

Other suitable ceramics include, but are not limited to, various stabilized or partially stabilized ceramics, various toughened ceramics, various transformation toughened ceramics, and various piezoceramic and oxide piezoceramic materials, including zirconia toughened alumina (ZTA), alumina toughened zirconia (ATZ), yttria-toughened zirconia (YTZ), yttria-stabilized zirconia (YSZ), magnesia stabilized zirconia (MSZ), hafnia stabilized zirconia, calcia stabilized zirconia, ceria stabilized zirconia, alumina stabilized zirconia, yttria stabilized tetragonal zirconia polycrystal, cesium-doped barium oxide, cesium-doped barium titanate, barium zirconate, barium titanium silicate, barium zirconate titanate, barium lanthanum cerium, transformation toughened zirconia-titania-yttria, and combinations thereof. The various stabilized and toughened ceramics may comprise 1 mole % to 9 mole % of the stabilizing element. For example, a yttria-stabilized zirconia may comprise the general formula $(ZrO_2)_{1-x}(Y_2O_3)_x$, where $0.09 \geq x \geq 0.01$. The yttria-stabilized zirconia may further comprise a 3 mole % yttria (3YSZ), a 5 mole % yttria (5YSZ), an 8 mole % yttria, a 9 mole % yttria, a 4.5 mole % yttria or a custom mole % yttria. Suitable glass-ceramics include, but are not limited to, lithium disilicate, alumina lanthanoborate, titania lanthanoborate, ceramic oxide silicates, ceramic oxide borates, ceramic oxide aluminates, ceramic oxide phosphates, and combinations thereof.

Some medical implantable devices have electrical conductors that provide other functions in addition to electrical conductivity, such as light transmission or encouraging tissue ingrowth. Consequently, the density and/or porosity of the electrical conductor may become important. An embodiment of the CRMC 100 electrical conductor of the present invention comprises a density ranging from >50% to 100%. An embodiment of the CRMC 100 electrical conductor of the present invention comprises a porosity ranging from 0% to <75%.

FIGS. 47 through 56 illustrate various via electrical conductor embodiments for use in hermetically sealed ceramic bodies with CRMC 148.

Figures 47, 48, 49, 50:
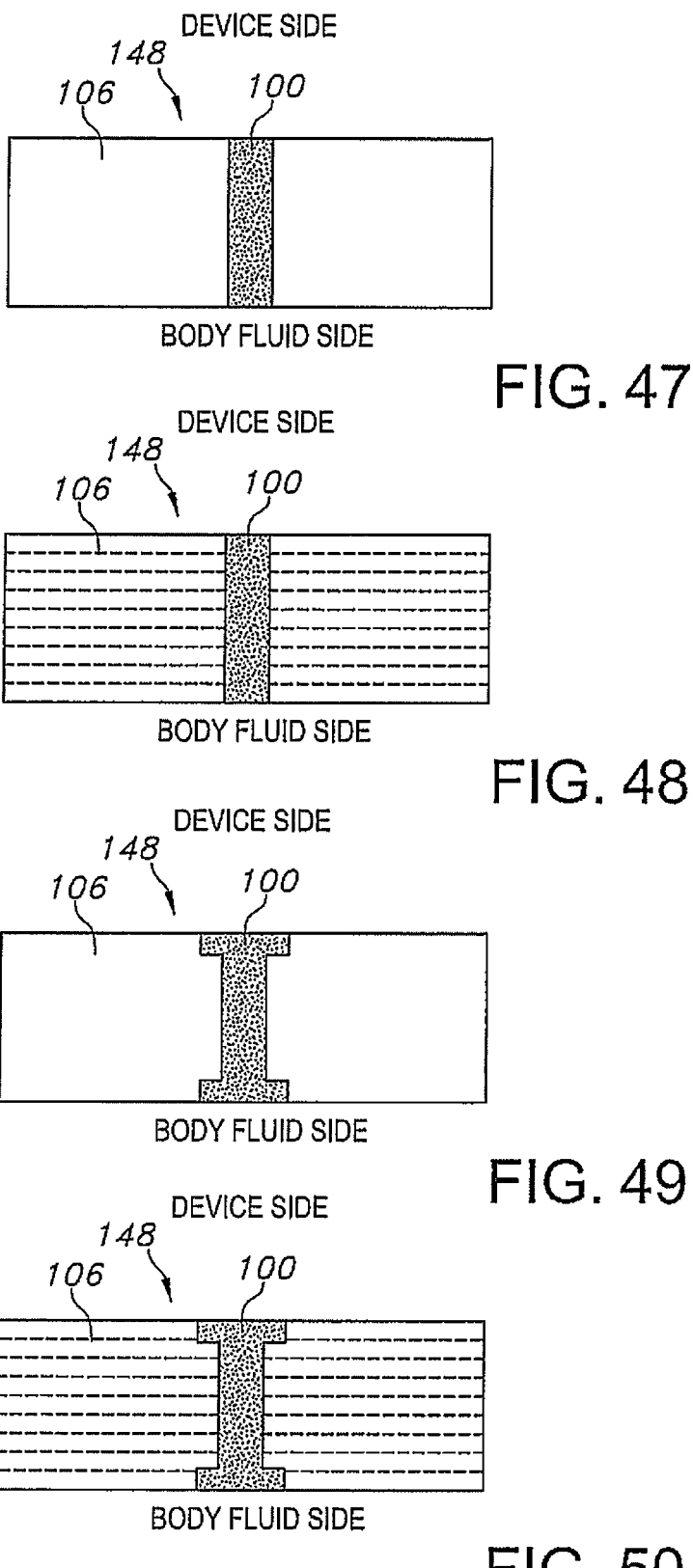
FIG. 47 is a monolithic ceramic body having a CRMC solid via electrical conductor.
FIG. 48 is a laminated multilayer feedthrough insulator having a CRMC solid via electrical conductor.
FIG. 49 is a monolithic feedthrough insulator having a CRMC solid via electrical conductor with both surface counterbore diameters larger than the diameter of the insulator via.
FIG. 50 is a laminated multilayer feedthrough insulator having a CRMC solid via electrical conductor with both surface counterbore diameters larger than the diameter of the insulator via.

FIG. 47 illustrates a hermetically sealed ceramic body with CRMC 148, wherein the CRMC 100 is an electrical conductor extending through the thickness of a monolithic ceramic body 106, to a first side surface and a second side surface of the ceramic body 106. The first side of the ceramic body 106 is a device side, which, when installed in an AIMD, is inside an AIMD housing. The second side of the ceramic body 106 is a body fluid side, which, when installed in an AIMD, is external of the AIMD housing.

FIG. 48 illustrates a hermetically sealed ceramic body with CRMC 148, wherein the CRMC 100 is an electrical conductor extending through the thickness of a laminated multilayer ceramic body 106, to a first side surface (which is a device side surface) and a second side surface (which is a body fluid surface) of the ceramic body 106.

FIG. 49 illustrates a hermetically sealed ceramic body with CRMC 148, wherein the CRMC 100 is a dumbbell-shaped electrical conductor extending through the thickness of a monolithic ceramic body 106, to a first side surface (which is a device side surface) and a second side surface (which is a body fluid surface) of the ceramic body 106. The diameter of the CRMC 100 first and second side surfaces is larger than the inside diameter of the portion of the ceramic via between the first and second ends of the CRMC dumbbell shape.

FIG. 50 illustrates a hermetically sealed ceramic body with CRMC 148, wherein the CRMC 100 is a dumbbell-shaped electrical conductor extending through the thickness of a laminated multilayer ceramic body 106, to a first side surface (which is a device side surface) and a second side surface (which is a body fluid surface) of the ceramic body 106. Like FIG. 49, the diameter of the CRMC 100 first and second side surfaces is larger than the inside diameter of the portion of the ceramic via between the first and second ends of the CRMC dumbbell shape.

Figures 51, 52, 53, 54:
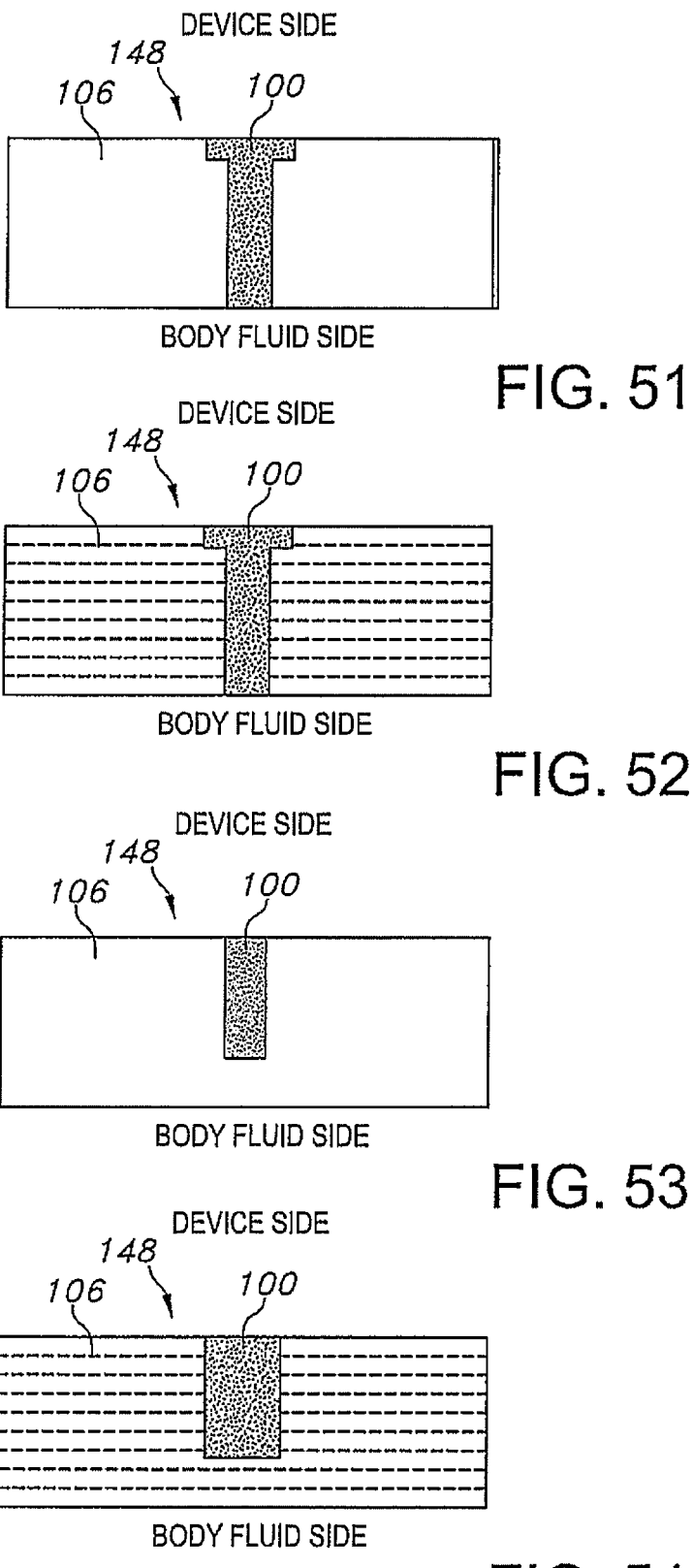
FIG. 51 is a monolithic feedthrough insulator having a CRMC via with a top surface counterbore diameter larger than the diameter of the insulator via.
FIG. 52 is a laminated multilayer feedthrough insulator having a CRMC via with a top surface counterbore diameter larger than the diameter of the insulator via.
FIG. 53 is a monolithic feedthrough insulator having a CRMC blind via electrical conductor.
FIG. 54 is a laminated multilayer feedthrough insulator having a CRMC blind via electrical conductor.

FIG. 51 illustrates a hermetically sealed ceramic body with CRMC 148, wherein the CRMC 100 is a T-shaped electrical conductor extending through the thickness of a monolithic ceramic body 106, to a first side surface (which is a device side surface) and a second side surface (which is a body fluid surface) of the ceramic body 106. The diameter of the CRMC 100 first side surface is larger than the inside diameter of the portion of the ceramic via below the first side surface of the T shape.

FIG. 52 illustrates a hermetically sealed ceramic body with CRMC 148, wherein the CRMC 100 is a T-shaped electrical conductor extending through the thickness of a laminated multilayer ceramic body 106, to a first side surface (which is a device side surface) and a second side surface (which is a body fluid surface) of the ceramic body 106. Like FIG. 51, the diameter of the CRMC 100 first side surface is larger than the inside diameter of the portion of the ceramic via below the first side surface of the T shape.

FIG. 53 illustrates a hermetically sealed ceramic body with CRMC 148, wherein the CRMC 100 is an electrical conductor formed in a blind via hole of a monolithic ceramic body 106. The surface of the CRMC 100 electrical conductor may reside on either the first side surface (which is a device side) or a second side (which is a body fluid) of the ceramic body 106.

FIG. 54 illustrates a hermetically sealed ceramic body with CRMC 148, wherein the CRMC 100 is an electrical conductor formed in a blind via hole of a laminated multilayer ceramic body 106.

Like FIG. 53, the surface of the CRMC 100 electrical conductor may reside on either the first side surface (which is a device side) or a second side (which is a body fluid) of the ceramic body 106.

FIG. 55 illustrates a hermetically sealed ceramic body with CRMC 148, wherein the CRMC 100 is an electrical conductor that has a metal addition 105 co-fired with the CRMC 100 at the same time the CRMC 100 is co-sintered with the monolithic ceramic body 106. The metal addition 105 of the CRMC 100 electrical conductor may reside on either the first side surface (which is a device side) or a second side (which is a body fluid) of the monolithic ceramic body 106.

FIG. 56 illustrates a hermetically sealed ceramic body with CRMC 148, wherein the CRMC 100 is an electrical conductor that has a metal addition 105 co-fired with the CRMC 100 at the same time the CRMC 100 is co-sintered with the laminated multilayer ceramic body 106. The metal addition 105 of the CRMC 100 electrical conductor may reside on either the first side surface (which is a device side) or a second side (which is a body fluid) of the laminated multilayer ceramic body 106.

Further regarding FIGS. 55 and 56, as previously defined, the CRMC 100 with a metal addition 105 is a combination electrical conductor with the metal addition 105 having many possible configurations, including custom metal constructs, which may comprise one or more construct parts. While the metal addition of FIGS. 55 and 56 show a terminal pin metal addition 105, it is understood that any of the configurations in the group disclosed in the definition of a metal construct may be used instead of the terminal pin shown.

FIGS. 57 through 67 illustrate various component embodiments for use in implantable medical devices using hermetically sealed ceramic bodies with CRMC 148.

FIG. 57 illustrates a cross sectional view of a hermetically sealed feedthrough 174 comprising a CRMC 100 electrical conductor. While only one CRMC 100 electrical conductor is shown, it is understood that the hermetically sealed feedthrough 174 may comprise "n" number of CRMC 100 electrical conductors. The ceramic body of the feedthrough comprises a feedthrough insulator 176 and the CRMC 100 electrical conductor 106. The ceramic body 106 is hermetically sealed to the feedthrough ferrule 178 by a braze material 182, which can be gold, gold-containing alloys, a palladium-containing alloys, platinum-containing alloys, or similarly oxide-resistant and biocompatible materials. The feedthrough insulator may optionally have a metallization disposed on its outside diameter or perimeter, which can be applied prior to brazing to encourage wetting of the feedthrough insulator 176 by the braze material. FIG. 57 shows two metallization layers, an adhesion metallization layer 186 applied directly onto the outer surface of the feedthrough insulator 176 and a wetting metallization layer 188 disposed atop the adhesion metallization layer 186. It is understood that only one layer can be used for both adhesion and wetting. Similarly, more than two metallization layers may alternatively be used. The feedthrough ferrule 178 of FIG. 57 is hermetically sealed to a device housing 180 by a laser weld 184. It is anticipated that the hermetically sealed body 106 with one or more CRMC 100 solid vias can be directly hermetically sealed to ferrule 178 without the use of a braze material. Additionally, the hermetically sealed body 106 with one or more CRMC 100 solid vias can alternatively be directly hermetically sealed to an opening in a device housing 180. The device housing 180 may alternatively have a preformed extension having a ferrule-like configuration but is contiguous with the housing 180 within which the hermetically sealed body 106 with one or more CRMC 100 solid vias is disposed and hermetically sealed.

Figure 58:
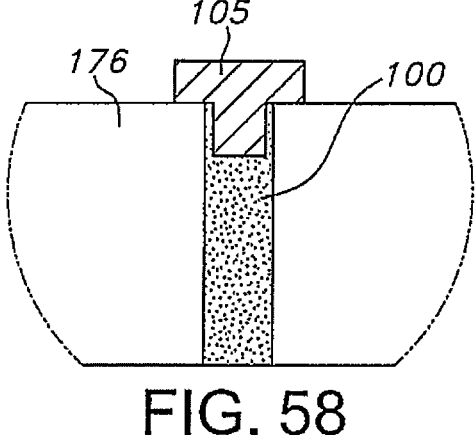
FIG. 58 is taken along 58-58 of FIG. 57 illustrating that the CRMC of the feedthrough insulator includes a metal addition.

FIG. 58 is taken along line 58-58 of FIG. 57 illustrating that the metal addition 105 may be a nail head insert.

Figure 59:
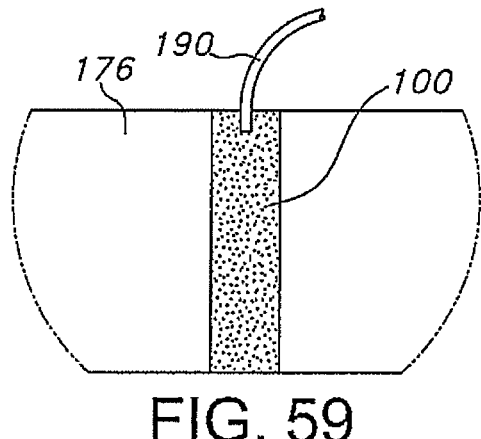
FIG. 59 is taken along 59-59 of FIG. 57 illustrating that the CRMC of the feedthrough insulator includes a leadwire.

FIG. 59 is taken along line 59-59 of FIG. 57 illustrating a CRMC 100 combination electrical conductor comprising a leadwire 190. Leadwire 190 may reside on either a first side surface (which is a device side) or a second side (which is a body fluid) of the hermetically sealed feedthrough ceramic body 106, or on both. A device side CRMC 100 combination electrical conductor may be electrically connected to electrical circuits or components internal of an implantable device, for example to a device circuit board, an EMI filter circuit board or circuit board connectors. A body fluid side CRMC 100 combination electrical conductor may be electrically connected to electrical circuits or components external of an implantable device for example, to device therapy delivery leads, a device header block, or device header block or lead connectors.

Figure 60:
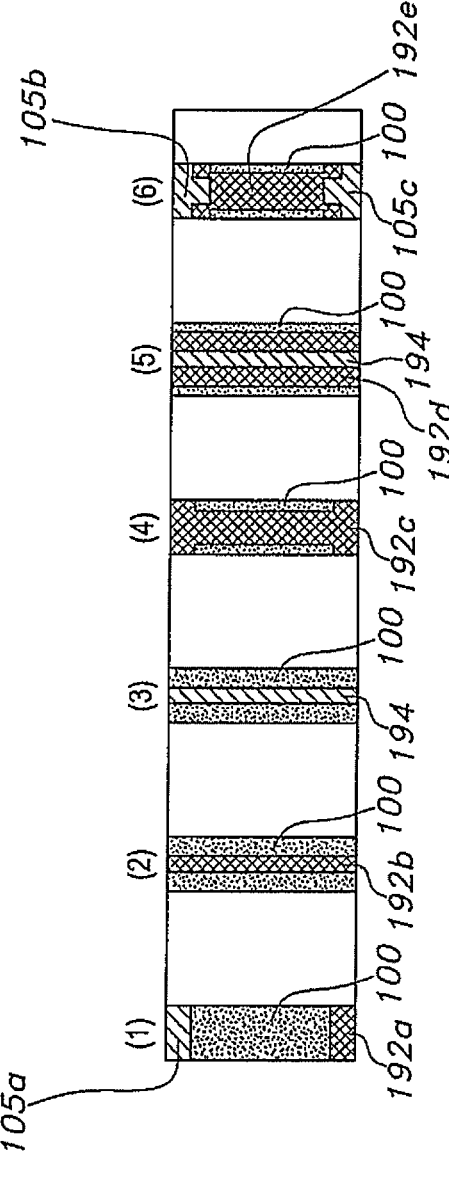
FIG. 60 illustrates a feedthrough insulator with various CRMC combination solid via electrical conductors.

FIG. 60 is a cross-sectional view of a ceramic body 106 illustrating various designs for hermetically sealed CRMC 100 combination electrical conductors (1) through (6). Combination electrical conductor (1) illustrates a CRMC 100 with a top metal insert 105*a* (a metal cap) and a bottom solid conductor 192*a* (solid cap of co-sintered metal paste). Combination electrical conductor (2) illustrates a CRMC 100 surrounding a solid conductor 192*b* (solid body of co-sintered metal paste extending centrally through the length of the CRMC 100 to a ceramic body first surface and a ceramic body second surface). Combination electrical conductor (3) illustrates a CRMC 100 surrounding a wire (or terminal pin) electrical conductor 194 extending centrally through the length of the CRMC 100 to a ceramic body first surface and a ceramic body second surface). Combination electrical conductor (4) illustrates a CRMC 100 surrounding a solid conductor 192*c* having a dumbbell-like shape (dumbbell-shaped solid body of co-sintered metal paste extending through the length of the CRMC 100 to a ceramic body first surface and a ceramic body second surface). The diameter of the first and second side surfaces of the dumbbell-shaped solid conductor 192*c* is larger than the diameter of the solid conductor portion between the first and second ends of the solid conductor dumbbell shape. Additionally, the first end of the dumbbell-shaped solid conductor 192*c* is flush with the first surface of the ceramic body 106 and the second end of the dumbbell-shaped solid conductor 192*c* is proud of the surface of the ceramic body 106.

Combination electrical conductor (5) illustrates a CRMC 100 surrounding solid conductor 192*d*, which surrounds a wire (or terminal pin) electrical conductor 194, the solid conductor 192*d* extending centrally through the length of the CRMC 100 and the wire (or terminal pin) electrical conductor 194 extending centrally through the length of the solid conductor 192*d*. The CRMC 100, the solid conductor 192*d* and the wire (or terminal pin) 194 all extend through the ceramic body 106 to a ceramic body first surface and a ceramic body second surface). Combination electrical conductor (6) illustrates a CRMC 100 surrounding a dumbbell-shaped solid conductor 192*e* having a dumbbell-like shape with a counterbore on each end. Metal additions 105*b* and 105*c* respectively reside in the counterbores at each end of the dumbbell-shaped solid conductor 192*e*. The metal additions 105*b* and 105*c* are both nail head inserts. The surface of metal insert 105(*b*) is proud of the surface of the ceramic body 106 and has a diameter larger than the inside diameter of the ceramic body via. The surface of the metal insert 105*c* is flush with the surface of the ceramic body 106 and thus has an outside diameter that is the same as the inside diameter of the ceramic body via.

The various designs of the CRMC 100 combination electrical conductors (1) through (6) are only examples. The CRMC 100 combination electrical conductors can have other designs, including custom designs, pending the needs of an application. For example, the CRMC 100 combination electrical conductors of the present invention can enable electrical connections. For instance, CRMC 100 combination electrical conductors (4) and (6) each have a proud feature. Proud features enable electrically connecting two electrically conductive pathways or components using an anisotropic conductive paste (ACP), an anisotropic conductive adhesive (ACA) or an anisotropic conductive film (ACF). Additionally, proud features can be used as electrodes or electrical connection pads. Also, the CRMC 100 combination electrical conductors can be custom designed to meet challenging electrical requirements, like high current levels or high voltage electrical pulsing.

Figure 61:
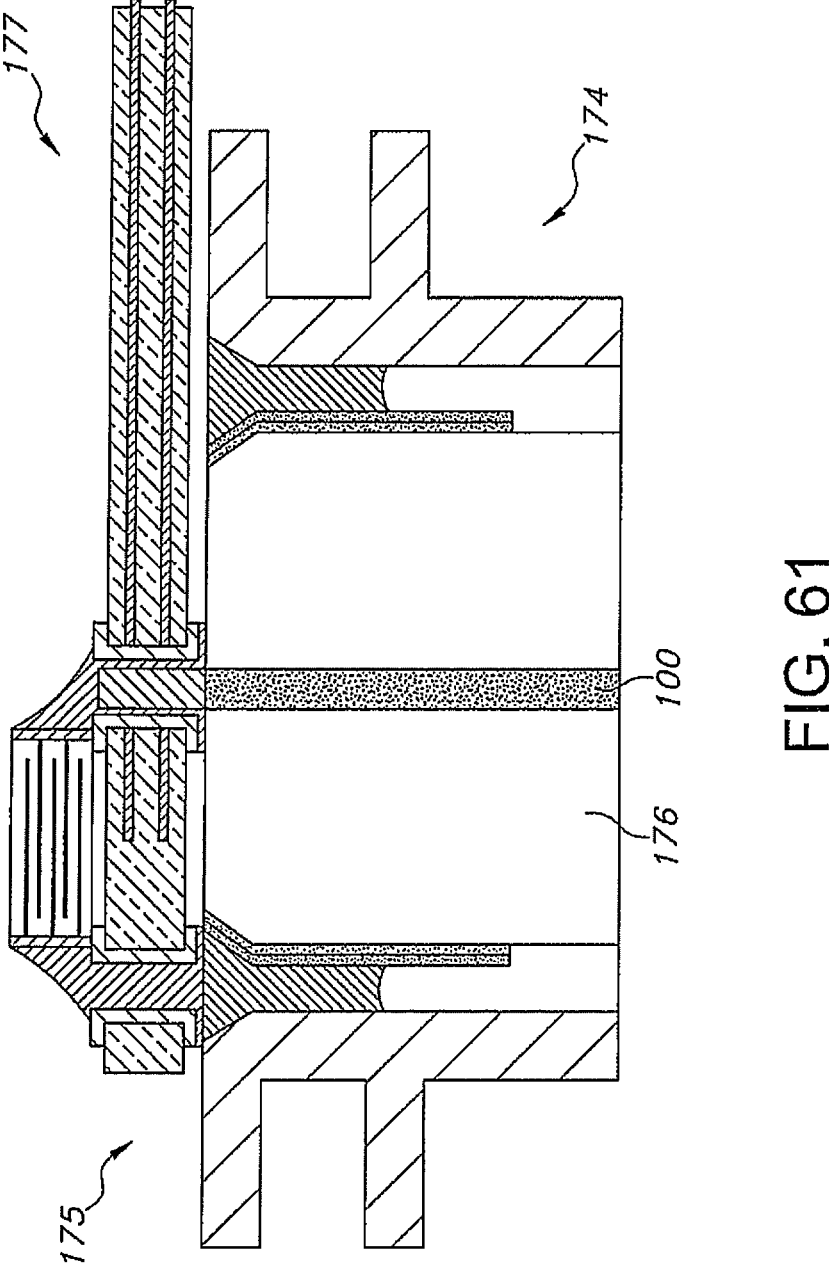
FIG. 61 illustrates a filtered feedthrough comprising a hermetically sealed feedthrough having a CRMC solid via electrical conductor.

FIG. 61 illustrates a filtered feedthrough 175 comprising a hermetically sealed feedthrough 174 having feedthrough insulator 176 with a CRMC 100 solid via electrical conductor. A conductive via 197 of the EMI filter circuit board 177 is electrically connected to the CRMC 100 solid via electrical conductor. It is understood that instead of an EMI filter circuit board 177, an EMI filter capacitor may be electrically connected to the CRMC 100 solid via electrical conductor of the hermetically sealed via 174.

Figure 62:
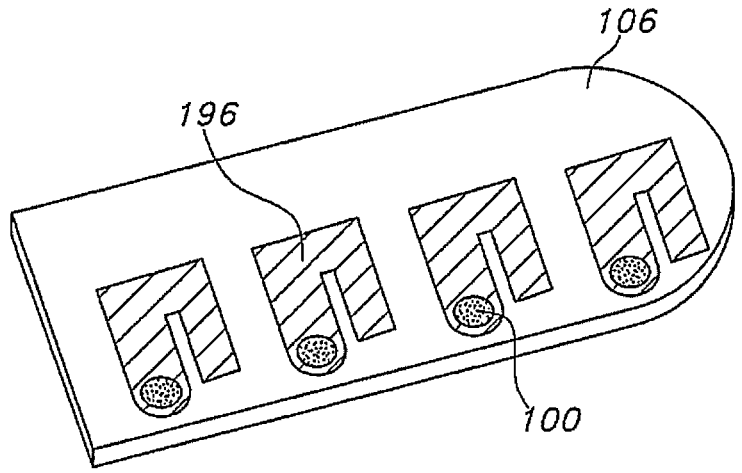
FIG. 62 illustrates a ceramic substrate on which is a conductive pathway comprising a trace and a solid via electrical conductor.

FIG. 62 illustrates a ceramic body 106 having conductive pathways 196 with a CRMC 100 solid via electrical conductors. The ceramic body 106 is a ceramic substrate and the conductive pathway 196 comprises a metal trace electrically connected to the CRMC 100 solid via. The embodiment of FIG. 62 may be used to form electronic components such as feedthrough hermetically sealed insulators, electronic circuit boards, EMI filters, sensors, communication chips, among others.

Figure 63:
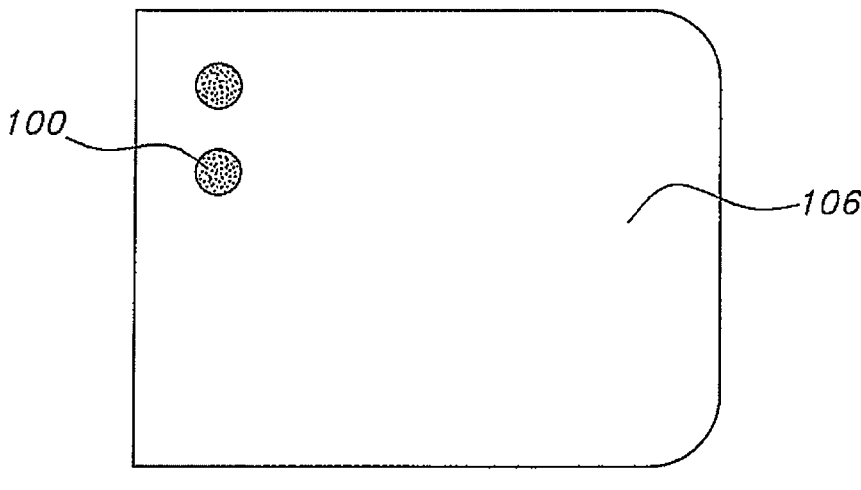
FIG. 63 illustrates a device housing having CRMC electrical conductors.

FIG. 63 illustrates a device housing having hermetically sealed CRMC 100 solid via electrical conductors. The device housing illustrated is a ceramic body 106, however, it is understood that device housing may alternatively be a biocompatible metal, for example, titanium, titanium alloys, stainless steel, nitinol, cobalt-chromium alloys and other such metal biocompatible metals and metal alloys. While two CRMC 100 solid via electrical conductors are shown, it is understood that a device housing may have one, more than two or "n" number of CRMC 100 solid via electrical conductors.

Figure 64:
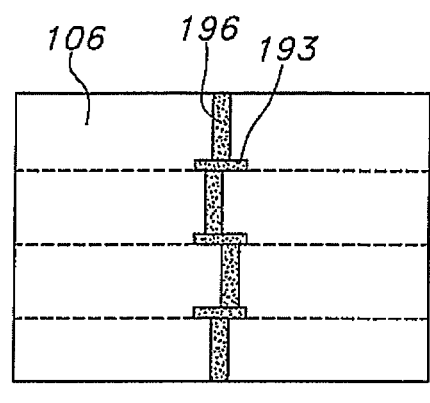
FIG. 64 illustrates a CRMC conductive pathway with catch pads.

FIG. 64 illustrates a CRMC 100 conductive pathway 196 extending through the thickness of a multilayer ceramic body 106 to a ceramic body first surface and a ceramic body second surface. The conductive pathway 196 includes catch pads that facilitate electrical continuity. Multilayer ceramic bodies may have "n" number of layers, each having a catch pad 193 to which the CRMC 100 solid via electrical conductors of each layer is electrically connected. While only one CRMC 100 conductive pathway 196 is shown, it is understood that the multilayer ceramic body 196 may have "n" number of CRMC 100 conductive pathways 196.

Figure 65:
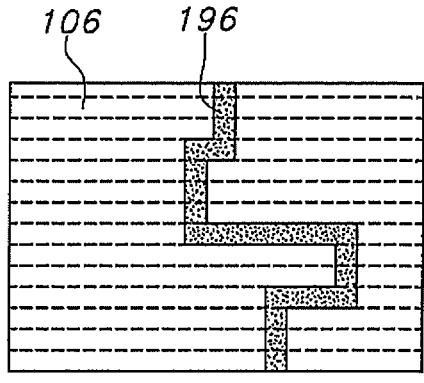
FIG. 65 illustrates a vertical multi-directional CRMC conductive pathway.

FIG. 65 illustrates a multi-directional CRMC 100 conductive pathway 196 extending through the thickness of a multilayer ceramic body 106 to a ceramic body first surface and a ceramic body second surface. While only vertical and horizontal directions are illustrated, it is understood that, depending on the via position in each ceramic body layer design and the order of layer stacking, the conductive pathway 196 can have oblique, canted and/or spiraling directions within the CRMC 100 conductive pathway 196. For example, ceramic body vias can uniquely be positioned in each layer and the plurality of layers can be stacked according to a defined order so that, when the stacked layers are laminated, a multilayer ceramic body 106 having a unique multi-directional CRMC 100 conductive pathway 196 is formed. Although FIG. 65 shows only one CRMC 100 conductive pathway 196 within ceramic body 106, it is understood that "n" number of CRMC 100 conductive pathways 196 may be made. Accordingly, a laminated multilayer ceramic body 106 may be formed where each ceramic body layer has a plurality of ceramic body vias with a disposed flowable medium therein. Additionally, the position of each ceramic body via in each ceramic body layer has a defined via position so that, when the ceramic body layers are stacked in a particular order, a group of conductive pathways 196 is formed. The conductive pathway group extends through the ceramic body 106 to first and second ceramic body surfaces. The configuration of the resultant conductive pathway group resembles a Litz wire. A Litz wire is composed of a number of insulated wire strands that are twisted or woven.

Figure 66:
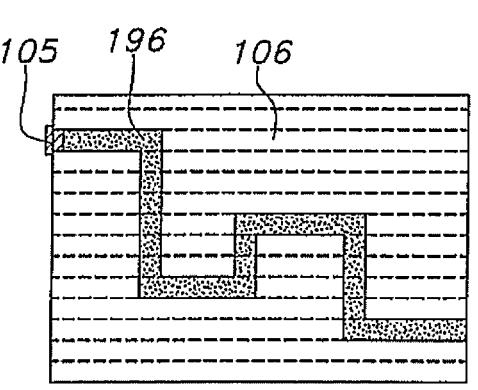
FIG. 66 illustrates a horizontal multi-directional CRMC conductive pathway.

FIG. 66 is similar to FIG. 65, except that now the multi-directional CRMC 100 conductive pathway 196 extending through the length of a multilayer ceramic body 106 to the surface of a ceramic body first edge (left side edge) and the surface of a ceramic body second edge (right side edge). A metal addition 105 is electrically connected to the left side edge of the CRMC 100 conductive pathway 196. Similar to FIG. 65, the embodiment of FIG. 66 may have "n" number of CRMC 100 conductive pathways 196 extending from edge-to-edge.

Further regarding the embodiments of FIGS. 65 and 66, the conductive pathway 196 may be one of a combination conductive pathway having: an electrically conductive portion being other than CRMC 100, an electronic component electrically connected somewhere within the conductive pathway, or both. Additionally, for embodiments having a plurality of conductive pathways 196, each conductive pathway may have the same configuration or at least one conductive pathway 196 may have a different conductive pathway configuration.

Figure 67:
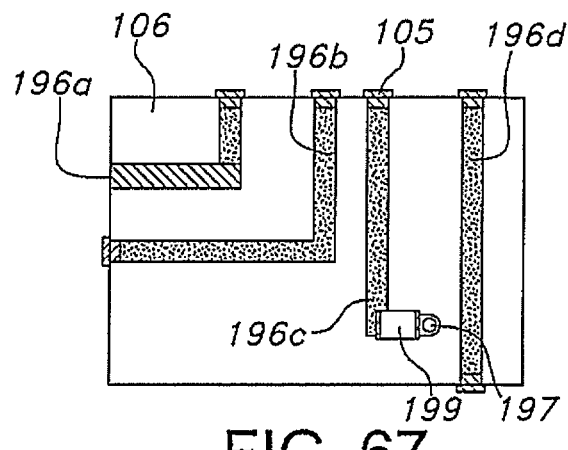
FIG. 67 illustrates a ceramic substrate on which various CRMC-containing conductive pathways are disposed.

FIG. 67 illustrates a top view of a ceramic body 106, which is a ceramic substrate, having a plurality of conductive pathways 196. Conductive pathway 196a is a two-directional combination conductive pathway comprising CRMC 100 and another conductive material. The CRMC 100 has an electrically connected metal addition 105 proud of the ceramic substrate edge. Conductive pathway 196b is two-directional CRMC 100 combination conductive pathway, with a metal addition 105 at the vertical and the horizontal edges. The metal addition 105 at the vertical edge is proud of the ceramic substrate edge, while the metal addition 105 at the horizontal edge is flush with the ceramic substrate edge. Conductive pathway 196c is a combination conductive pathway comprising a metal addition 105, a vertical CRMC 100, an MLCC chip capacitor 199 and a conductive via 197. The metal addition 105 is electrically connected to the surface of the ceramic body 106. On the opposite end of the CRMC 100, the left metallization edge of an MLCC chip capacitor 199 is electrically connected to the CRMC 100. The right metallization edge of the MLCC chip capacitor 199 is electrically connected to the conductive via 197 of the ceramic substrate. Conductive pathway 196d is a combination conductive pathway comprising a unidirectional CRMC 100 having a metal addition 105 electrically connected at the top and bottom ceramic substrate edges. The metal addition 105 at the top end of the vertical portion is proud of the ceramic body surface, while the metal addition 105 at the bottom end of the horizontal portion is flush with the ceramic body surface.

Figure 68:
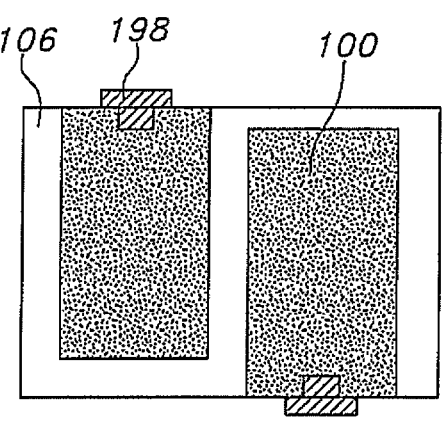
FIG. 68 illustrates a ceramic substrate on which CRMC electrodes are disposed.

FIG. 68 illustrates a ceramic body 106, which is a substrate, on which CRMC 100 electrodes are disposed. Each electrode has a metal addition 105. The CRMC 100 electrode on the right has a metal addition 105 at the ceramic substrate bottom edge. The CRMC 100 electrode on the left has a metal addition on the ceramic substrate top edge. The metal additions 105 can be used to make electrical connections.

Figure 69:
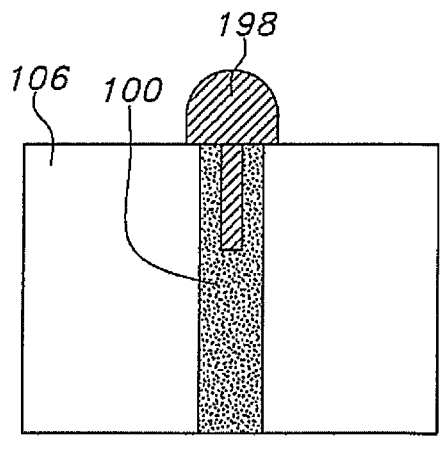
FIG. 69 illustrates a ceramic body having a CRMC electrical conductor and an electrically connected electrode.

FIG. 69 illustrates a ceramic body 106 having a CRMC 100 electrical conductor and an electrode 198. The electrode 198 is electrically connected to and stands proud of the CRMC 100 electrical conductor. The electrode 198 may either be high density CRMC 100 or a CRMC 100 having defined porosity. A CRMC 100 electrode 198 may be coated with titanium nitride, iridium oxide or a non-toxic, biocompatible metal. The electrode 198 may comprise CRMC 100 and another electrically conductive material. The electrode 198 may comprise a metal or a metal alloy, which may optionally be coated with titanium nitride or iridium oxide. The electrode may have a porous metal optionally coated with titanium nitride or iridium oxide. The electrode may comprise a metal core surrounded by CRMC 100. The electrode may be configured to meet application requirements.

It is appreciated that various modifications to the inventive concepts described herein may be apparent to those skilled in the art without departing from the spirit and scope of the present invention as defined by the hereinafter appended claims.

What is claimed is:

1. A composite particle powder, consisting of:
   a) platinum particles that are mechanically connected and chemically bonded to alumina particles without the alumina particles having been sintered to each other or having undergone a phase change, wherein the mechanically connected and chemically bonded platinum-alumina composite particles are a powder ranging in size from about 1 µm to about 50 µm, and
   b) wherein:
      i) as exhibited by transmission electron microscopy, an interface between the mechanically connected and chemically bonded platinum-alumina composite particles comprises visible intermingled platinum and alumina atoms that have disorder and dislocation; and
      ii) as exhibited by transmission electron microscopy selected area electron diffraction, the crystallographic structure at the interface between mechanically connected and chemically bonded platinum-alumina composite particles comprises a lattice point row that defines a zone axis intersected by platinum and alumina lattice planes that are parallel; and
      iii) as defined by a redistribution of valence charge determined by transmission electron microscopy-electron energy-loss spectroscopy, the mechanically connected and chemically bonded platinum-alumina composite particles have atomic bonding.

2. The composite particle powder of claim 1, wherein the platinum and alumina particles are characterized as having been heated to a temperature that ranges from about 350° C. to about 900° C. to mechanically connect and chemically bond the platinum particles to the alumina particles without the alumina particles having been sintered to each other or having undergone a phase change.

* * * * *